(12) United States Patent
Friedlander et al.

(10) Patent No.: US 7,528,106 B2
(45) Date of Patent: May 5, 2009

(54) COMPOSITIONS AND METHODS FOR TREATMENT OF NEOVASCULAR DISEASES

(75) Inventors: Martin Friedlander, Del Mar, CA (US); Hilda Edith Aguilar, San Diego, CA (US); Michael I. Dorrell, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 183 days.

(21) Appl. No.: 11/145,587

(22) Filed: Jun. 6, 2005

(65) Prior Publication Data

US 2006/0003933 A1    Jan. 5, 2006

Related U.S. Application Data

(60) Provisional application No. 60/577,156, filed on Jun. 4, 2004, provisional application No. 60/585,273, filed on Jul. 1, 2004, provisional application No. 60/655,801, filed on Feb. 24, 2005.

(51) Int. Cl.
*A61K 38/00* (2006.01)
*A61K 31/7088* (2006.01)
*C07K 14/00* (2006.01)
*C07H 21/00* (2006.01)
*A61K 31/535* (2006.01)

(52) U.S. Cl. ............... 514/2; 514/44; 514/230.5; 530/350; 536/22.1

(58) Field of Classification Search .......... None
See application file for complete search history.

(56) References Cited

U.S. PATENT DOCUMENTS

2003/0105000 A1* 6/2003 Pero et al. ............. 514/12

2004/0029788 A1* 2/2004 Bender et al. ........... 514/9

OTHER PUBLICATIONS

Wang et al. (Current Medicinal Chem. 2000 7:437-453).*
Wakasugi et al. (Proc Natl. Acad. Sci., Jan. 8, 2002, 99:173-177).*
Otani et al. (Proc Natl. Acad. Sci., Jan. 8, 2002, 99:178-83).*
Eyetech Study Group (Retina, 2002, 22:143-152).*
Ruckman et al. J. Biol. Chem. 1998,273: 20556- 30 20567.*
Gura (Science, 1997, 278:1041-1042).*
Kaiser (Science, 2006, 313, 1370).*
Clamp and Jayson (British Journal of Cancer, 2005 93:967-972).*
Yang et al. (Trends in Biochemical Sciences May 2004, 29: 250-256).*
Burgess et al (J of Cell Bio. 111:2129-2138, 1990).*
Lazar et al (Molecular and Cellular Biology, 1988, 8;1247-1252).*
Scott et al (Nature Genetics, 1999, 21:440-443).*

* cited by examiner

*Primary Examiner*—Karen A Canella
*Assistant Examiner*—Peter J Reddig
(74) *Attorney, Agent, or Firm*—Olson & Cepuritis, Ltd.

(57) ABSTRACT

The present invention provides compositions and methods of treating neovascular diseases, such as a retinal neovascular diseases and tumors, by administering to a patient suffering from a neovascular disease or tumor a vascular development inhibiting amount of a combination of the angiogenesis suppressing drugs comprising an angiostatic fragment of tryptophanyl-tRNA synthetase (TrpRS) and at least one compound selected from the group consisting of a vascular endothelial growth factor (VEGF) signaling inhibitor and an integrin signaling inhibitor. Compositions for use in the methods include an admixture of an angiostatic fragment of tryptophanyl-tRNA synthetase (TrpRS) and at least one of a vascular endothelial growth factor (VEGF) signaling inhibitor and an integrin signaling inhibitor, together with a pharmaceutically acceptable excipient.

1 Claim, 60 Drawing Sheets

T2-TrpRS (SEQ ID NO: 1)

MSAKGIDYDKLIVRFGSSKIDKELINRIERATGQRPHHFLRRGIFFSFFSHRDMNQVLDAYENKKPFYLYTGRGPSSEAM
HVGHLIPFIFTKWLQDVFNVPLVIQMTDDEKYLWKDLTLDQAYSYAVENAKDIIACGFDINKTFIFSDLDYMGMSSG
FYKNVVKIQKHVTFNQVKGIFGFTDSDCIGKISFPAIQAAPSFSNSFPQIFRDRTDIQCLIPCAIDQDPYFRMTRDV
APRIGYPKPALLHSTFFPALQGAQTKMSASDPNSSIFLTDTAKQIKTKVNKHAFSGGRDTIEEHRQFGGNCDVDVSF
MYLTFFLEDDDKLEQIRKDYTSGAMLTGELKKALIEVLQPLIAEHQARRKEVTDEIVKEFMTPRKLSFDFQ

T2-TrpRS-GD (SEQ ID NO: 2)

MSAKGIDYDKLIVRFGSSKIDKELINRIERATGQRPHHFLRRGIFFSFFSHRDMNQVLDAYENKKPFYLYTGRGPSSEAM
HVGHLIPFIFTKWLQDVFNVPLVIQMTDDEKYLWKDLTLDQAYGDAVENAKDIIACGFDINKTFIFSDLDYMGMSSG
FYKNVVKIQKHVTFNQVKGIFGFTDSDCIGKISFPAIQAAPSFSNSFPQIFRDRTDIQCLIPCAIDQDPYFRMTRDV
APRIGYPKPALLHSTFFPALQGAQTKMSASDPNSSIFLTDTAKQIKTKVNKHAFSGGRDTIEEHRQFGGNCDVDVSF
MYLTFFLEDDDKLEQIRKDYTSGAMLTGELKKALIEVLQPLIAEHQARRKEVTDEIVKEFMTPRKLSFDFQ

FIG. 1

Mini TrpRS (SEQ ID NO: 3)

MSYKAAAGEDYKADCPPGNPAPTSNHGPDATEAEEDFVDPWTVQTSSAKGIDYDKLIVRFGSSKIDKELINRIERAT
GQRPHHFLRRGIFFSHRDMNQVLDAYENKKPFYLYTGRGPSSEAMHVGHLIPFIFTKWLQDVFNVPLVIQMTDDEKY
LWKDLTLDQAYSYAVENAKDIIACGFDINKTFIFSDLDYMGMSSGFYKNVKIQKHVTFNQVKGIFGFTDSDCIGKI
SFPAIQAAPSFSNSFPQIFRDRTDIQCLIPCAIDQDPYFRMTRDVAPRIGYPKPALLHSTFFPALQGAQTKMSASDP
NSSIFLTDTAKQIKTKVNKHAFSGGRDTIEEHRQFGGNCDVDVSFMYLTFFLEDDDKLEQIRKDYTSGAMLTGELKK
ALIEVLQPLIAEHQARRKEVTDEIVKEFMTPRKLSFDFQ

T1-TrpRS (SEQ ID NO: 4)

SNHGPDATEAEEDFVDPWTVQTSSAKGIDYDKLIVRFGSSKIDKELINRIERATGQRPHHFLRRGIFFSHRDMNQVL
DAYENKKPFYLYTGRGPSSEAMHVGHLIPFIFTKWLQDVFNVPLVIQMTDDEKYLWKDLTLDQAYSYAVENAKDIIA
CGFDINKTFIFSDLDYMGMSSGFYKNVKIQKHVTFNQVKGIFGFTDSDCIGKISFPAIQAAPSFSNSFPQIFRDRT
DIQCLIPCAIDQDPYFRMTRDVAPRIGYPKPALLHSTFFPALQGAQTKMSASDPNSSIFLTDTAKQIKTKVNKHAFS
GGRDTIEEHRQFGGNCDVDVSFMYLTFFLEDDDKLEQIRKDYTSGAMLTGELKKALIEVLQPLIAEHQARRKEVTDE
IVKEFMTPRKLSFDFQ

FIG. 2

| | Size | pI | Charging | Angiogenic | Angiostatic |
|---|---|---|---|---|---|
| Full-Length TrpRS | 53Kd | 5.7 | + | - | - |
| Mini TrpRS (splice variant) | 48Kd | 5.8 | + | - | + |
| T1 (cleavage product) | 46Kd | 5.9 | + | - | + |
| T2 (cleavage product) | 43Kd | 6.8 | - | - | + |

*Note: A mutant of each of the four proteins has been made in which DLT(205-207) is replaced with ELR

```
  1 MPNSEPASLL ELFNSIATQG ELVRSLKAGN ASKDEIDSAV KMLVSLKMSY KAAAGEDYKA DCPPGNPAPT SNHGPDATEA
                                                              →miniTrpRS                →T1
 81 EEDFVDPWTV QTSSAKGIDY DKLIVRFGSS KIDKELINRI ERATGQRPHH FLRRGIFFSH RDMNQVLDAY ENKKPFYLYT
161 GRGPSSEAMH VGHLIPFIFT KWLQDVFNVP LVIQMTDDEK YLWKDLTLDQ AYGDAVENAK DIIACGFDIN KTFIFSDLDY
              →T2
241 MGMSSGFYKN VVKIQKHVTF NQVKGIFGFT DSDCIGKISF PAIQAAPSFS NSFPQIFRDR TDIQCLIPCA IDQDPYFRMT
321 RDVAPRIGYP KPALLHSTFF PALQGAQTKM SASDPNSSIF LTDTAKQIKT KVNKHAFSGG RDTIEHRQF GGNCDVDVSF
401 MYLTFFLEDD DKLEQIRKDY TSGAMLTGEL KKALIEVLQP LIAEHQARRK EVTDEIVKEF MTPRKLSFDF Q
```

FIG. 3

FIG. 11
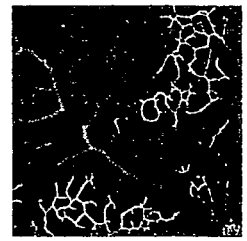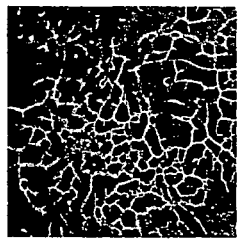
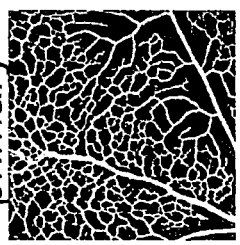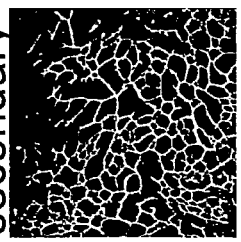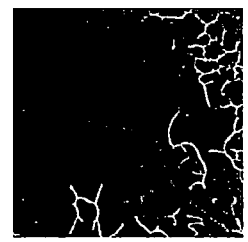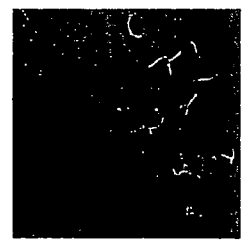
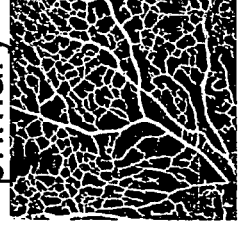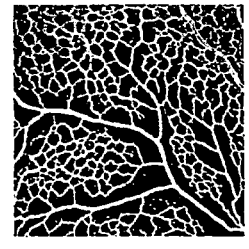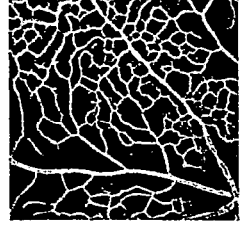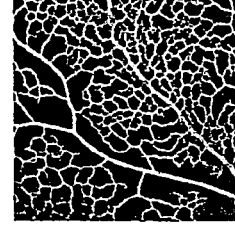

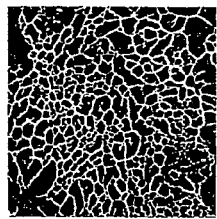
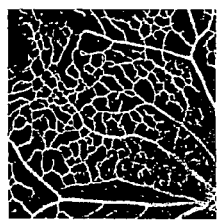
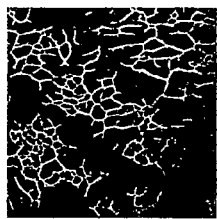
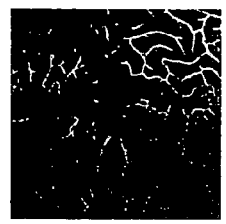
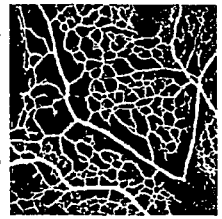
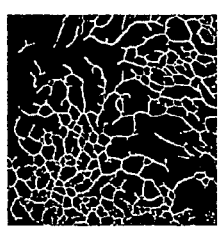
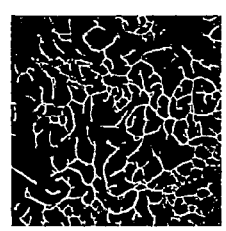
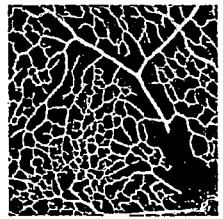
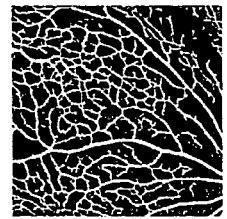
FIG. 15

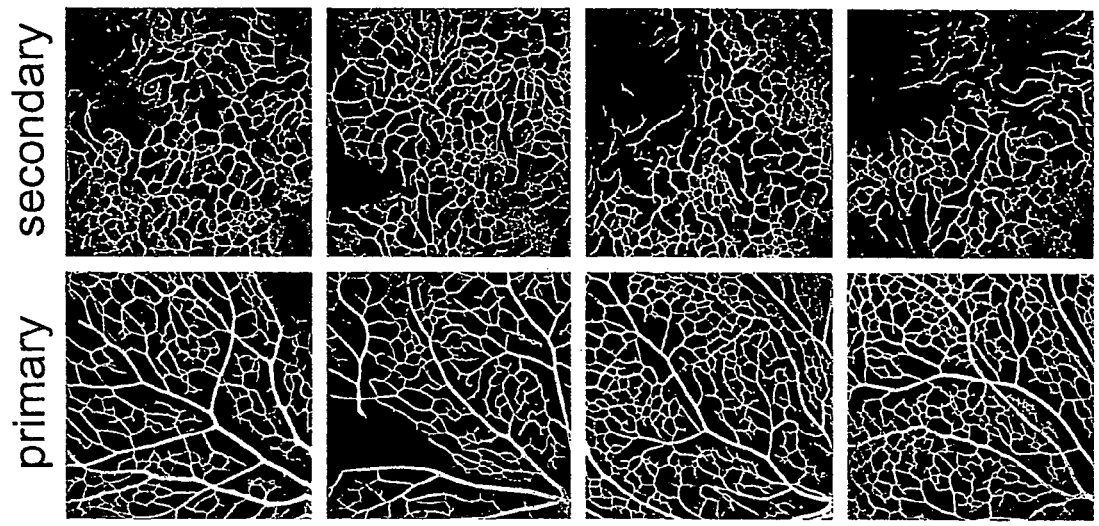
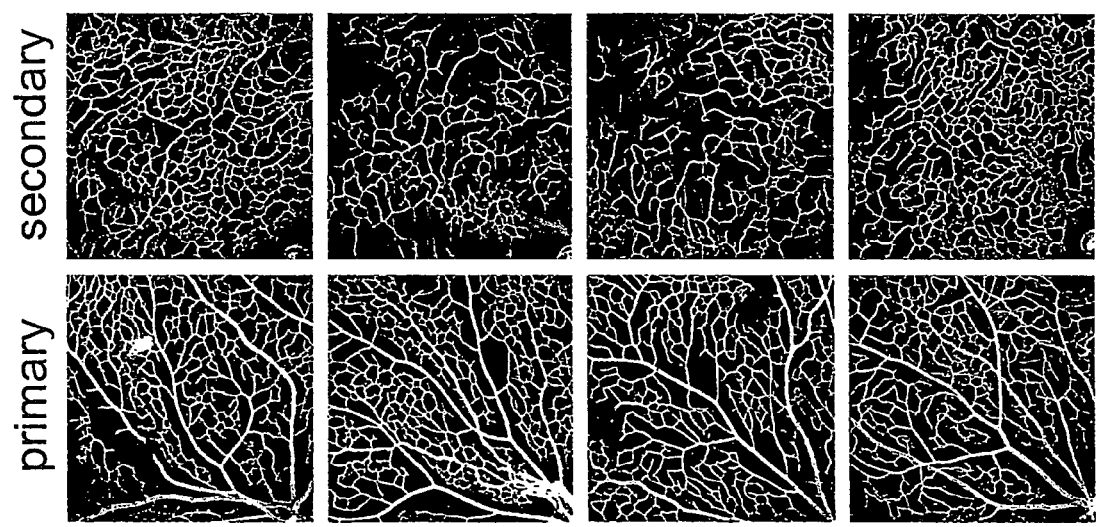
FIG. 22

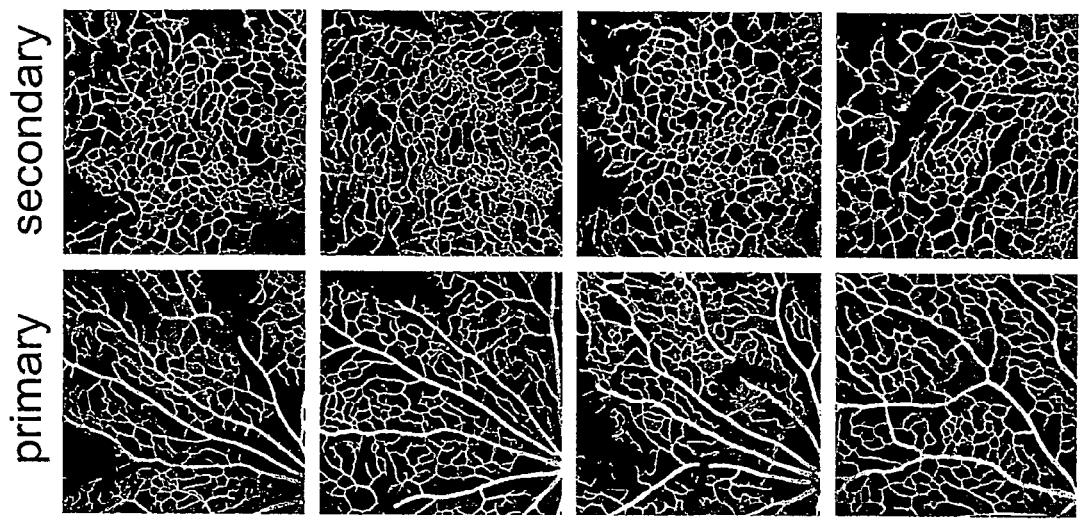
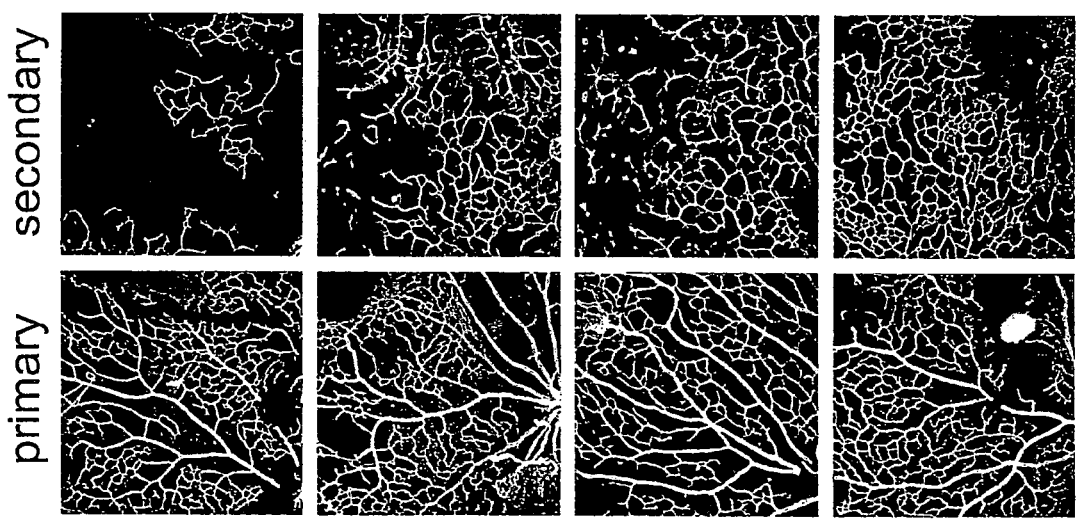
FIG. 23

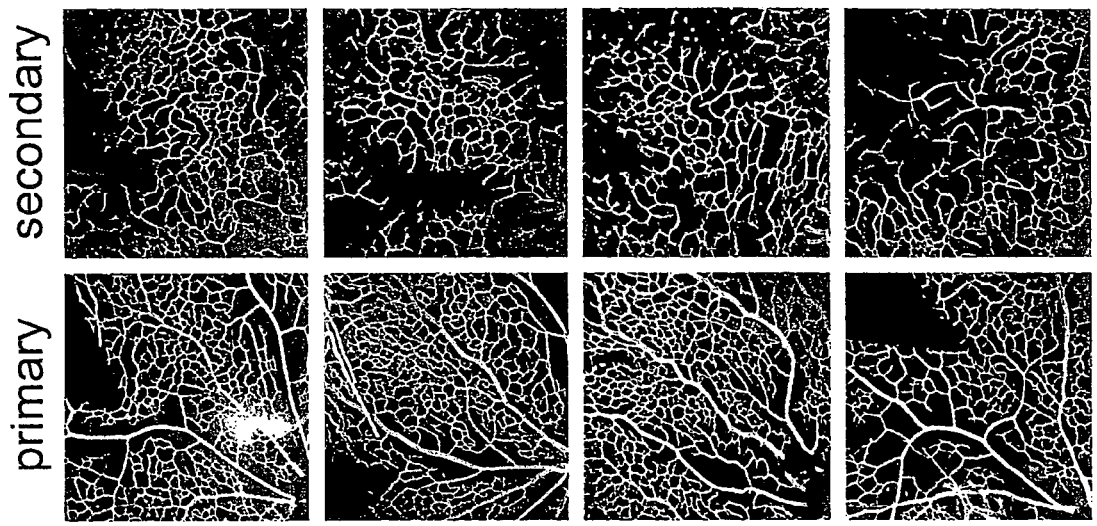
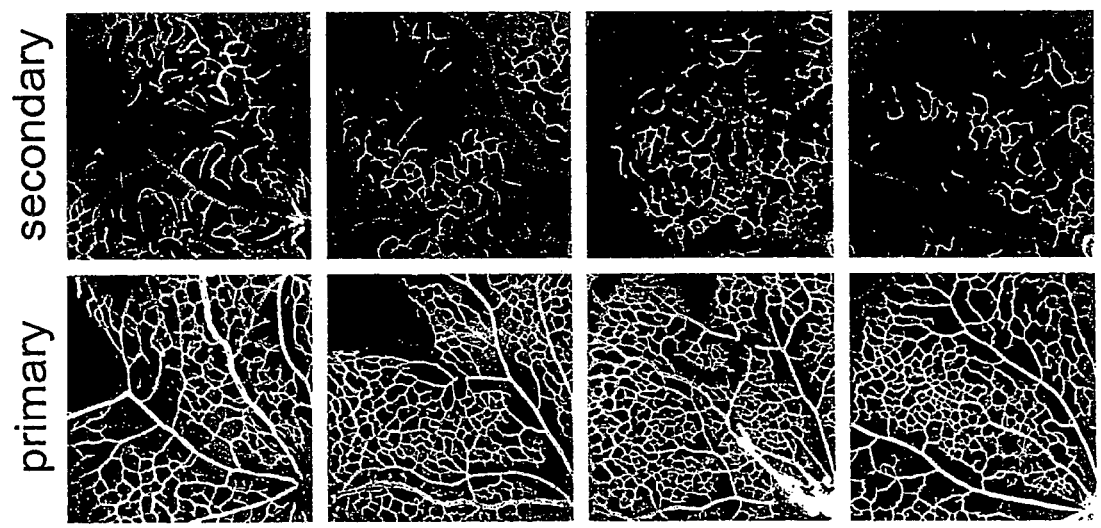
FIG. 24

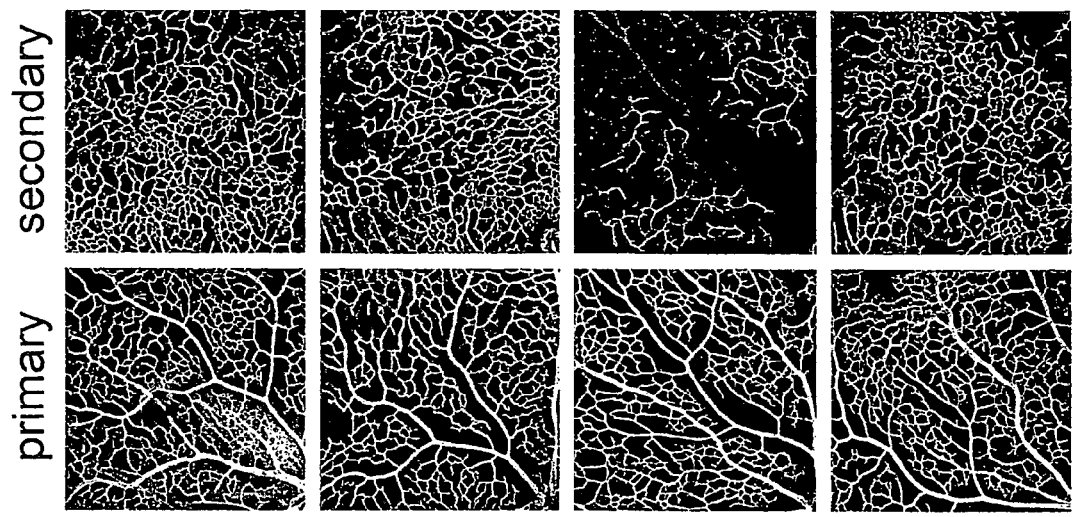
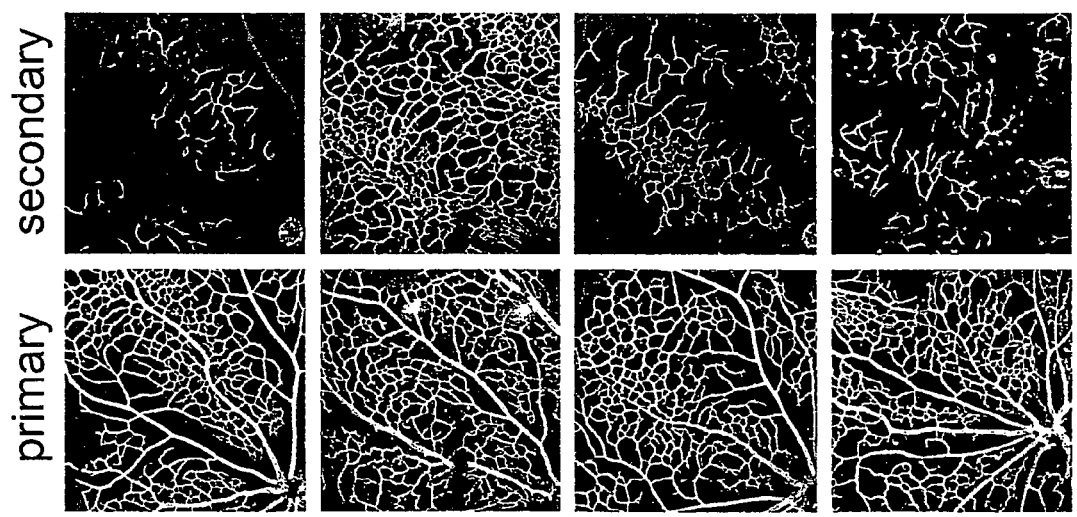
FIG. 25

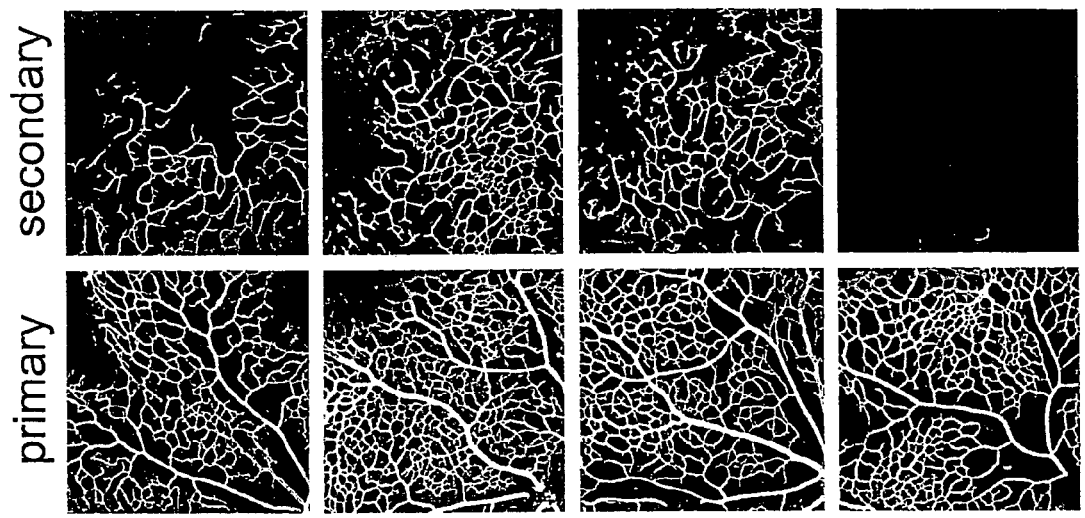
FIG. 26
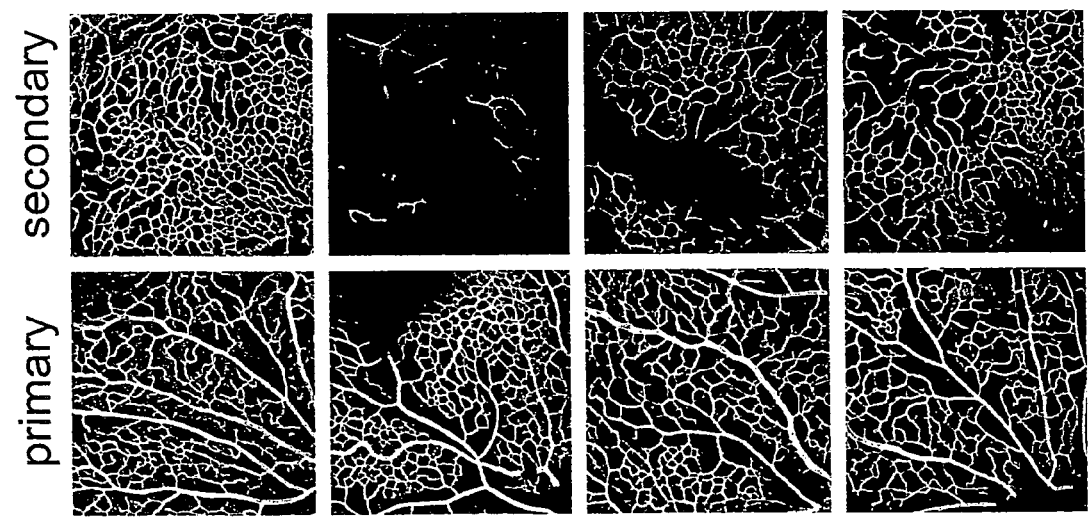

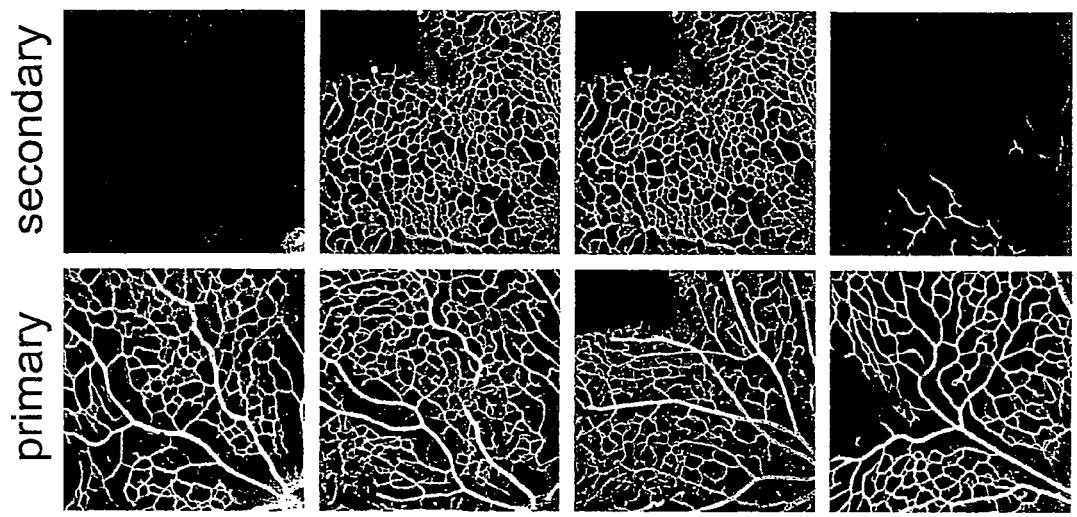
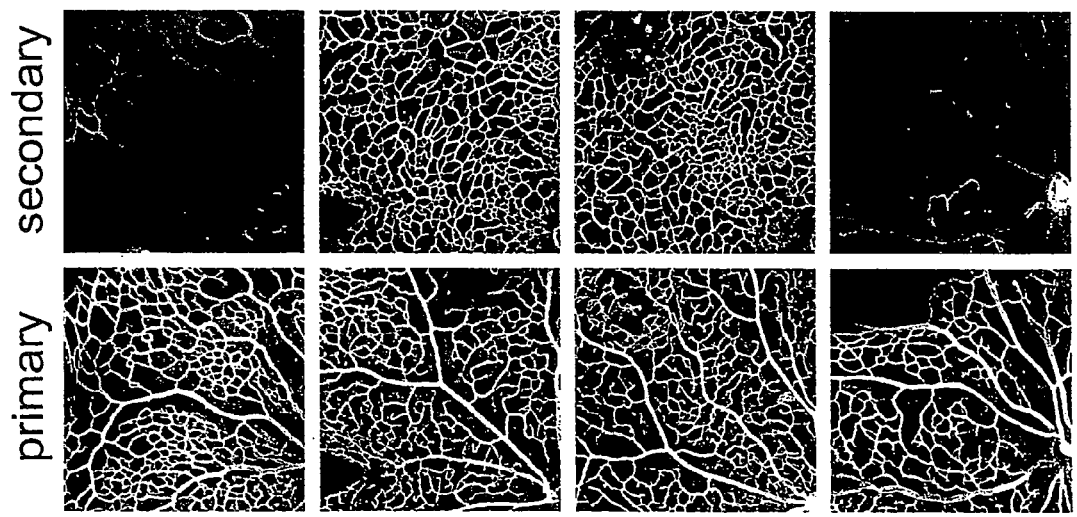
FIG. 27

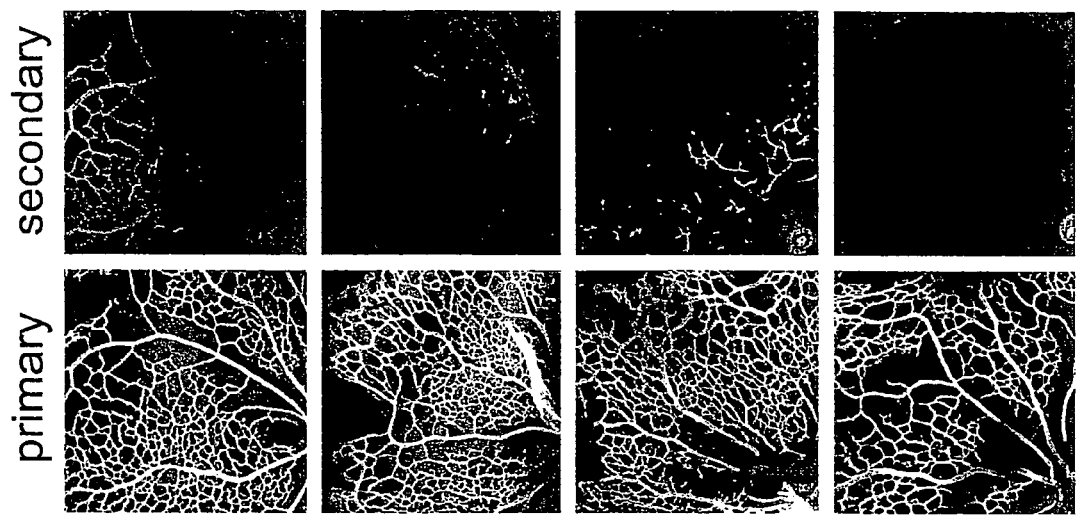
FIG. 28
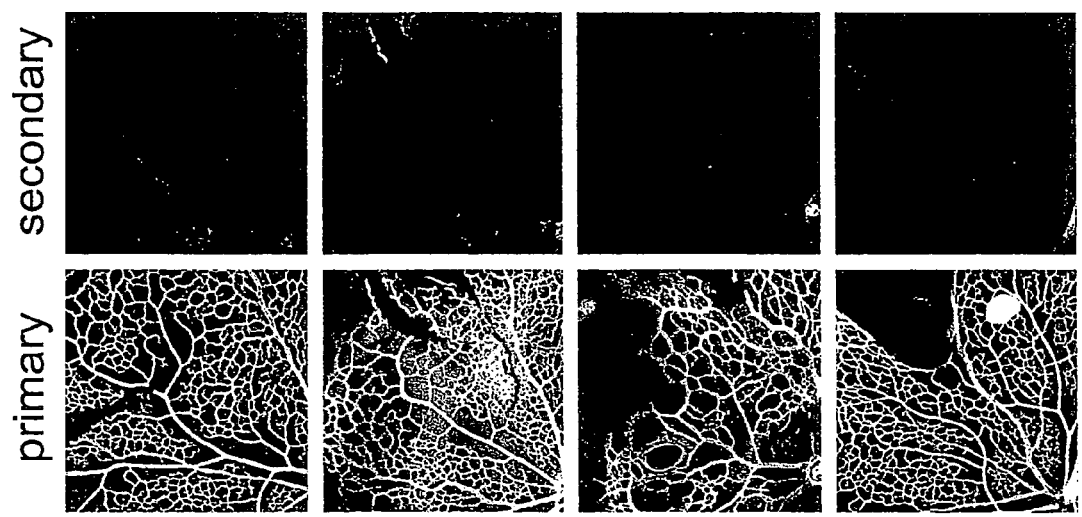

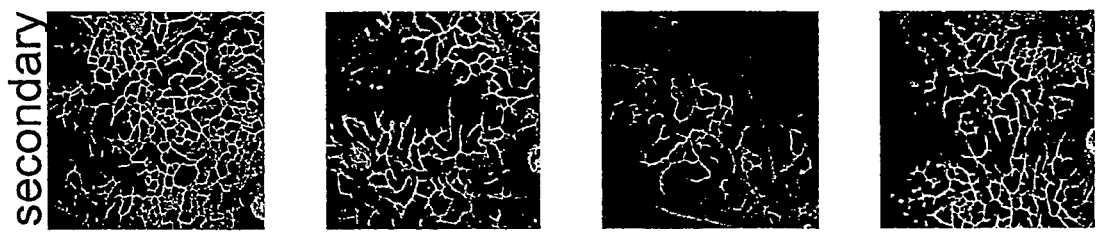
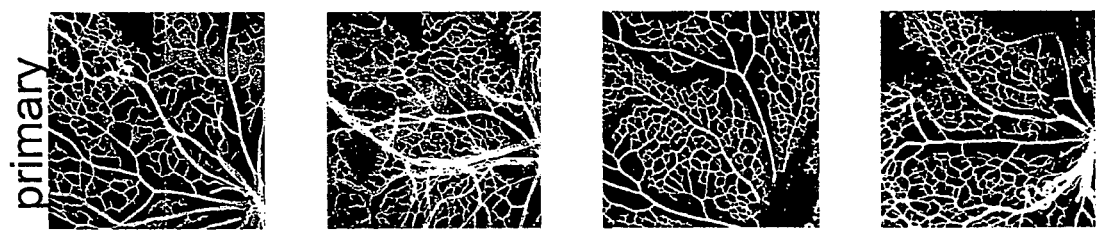
FIG. 31
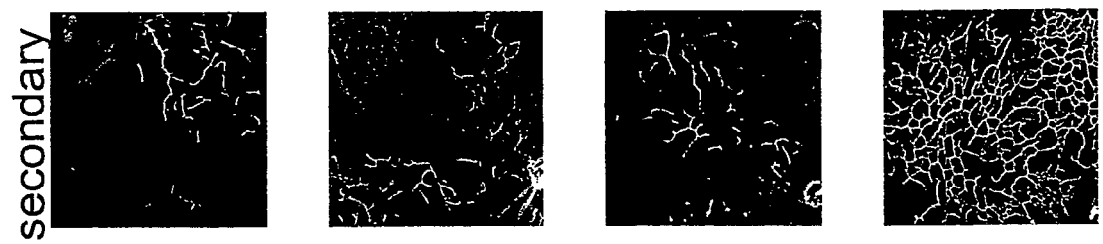
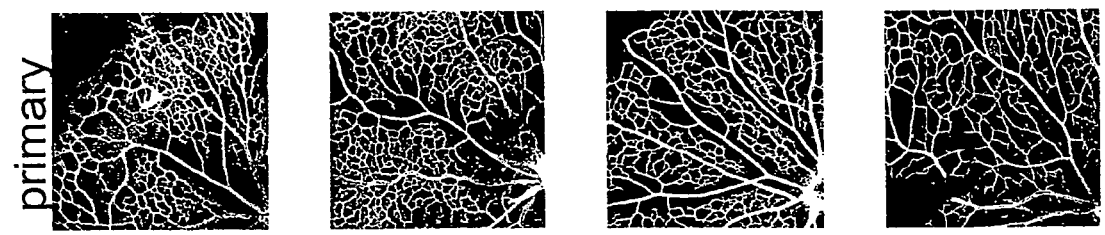

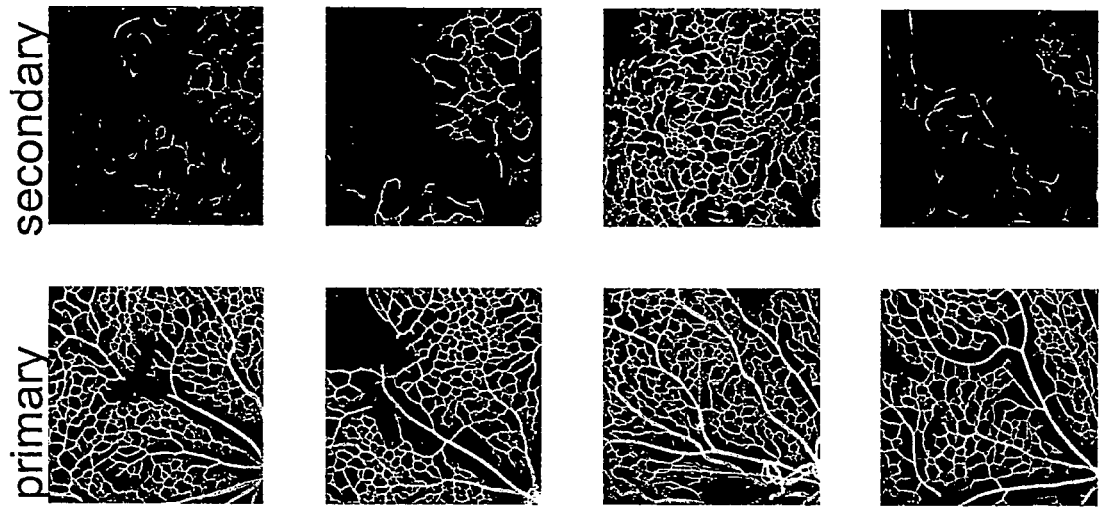
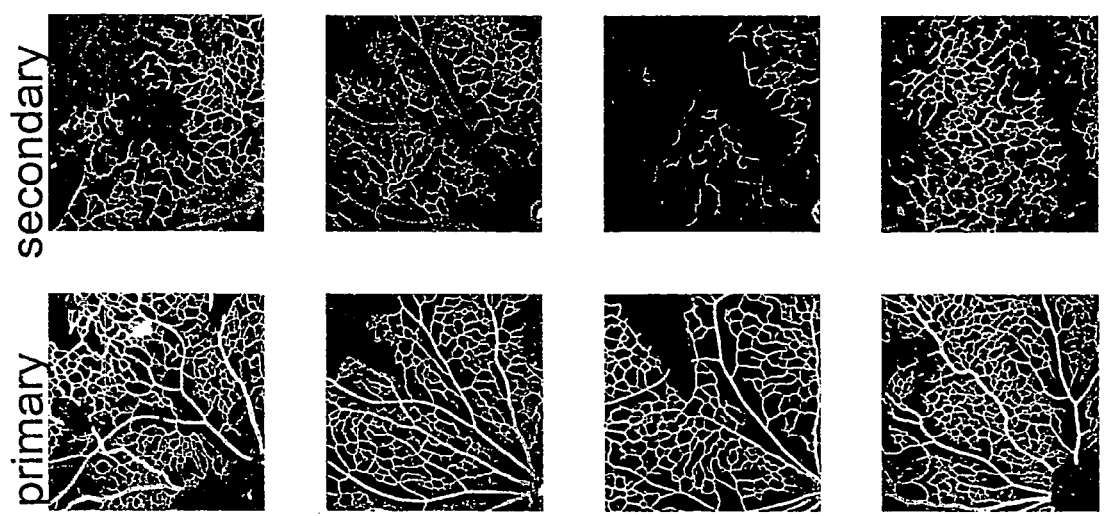
FIG. 32

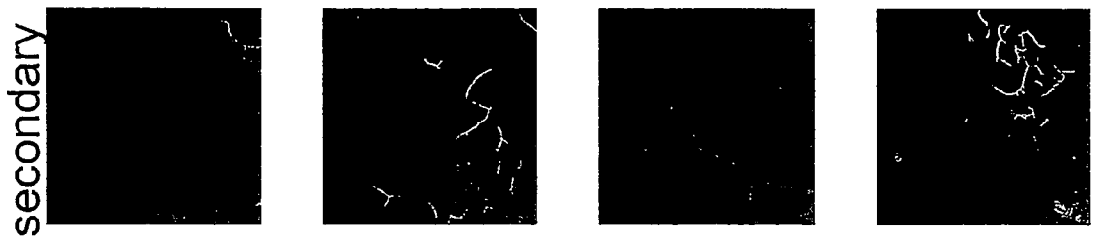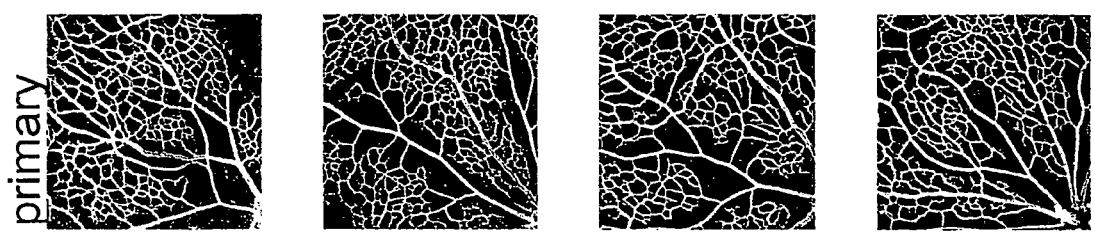
FIG. 34
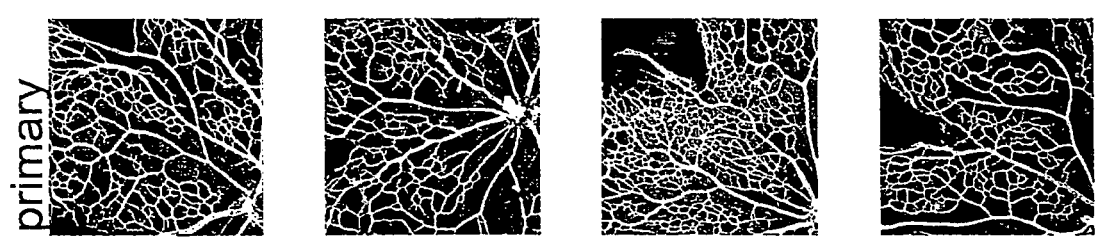

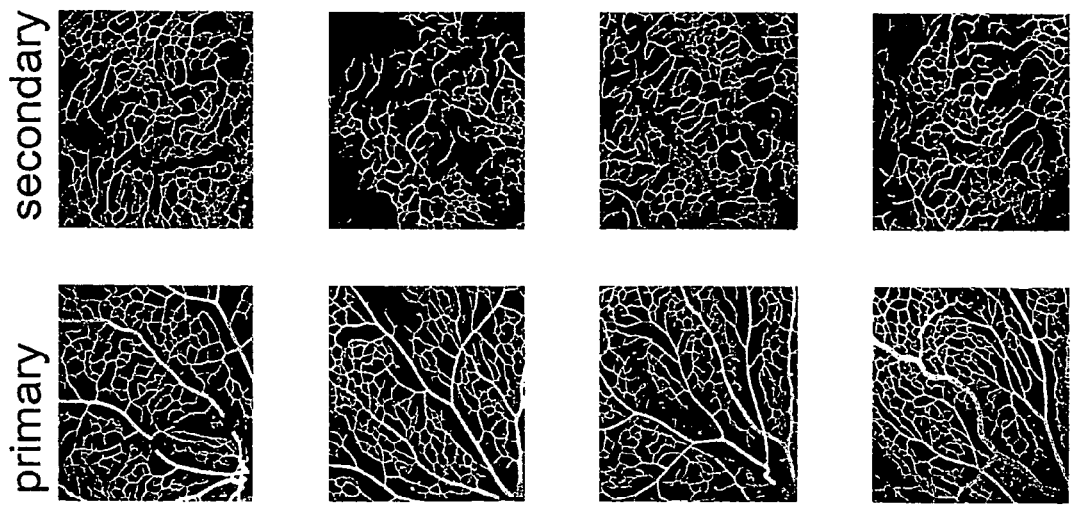
FIG. 35
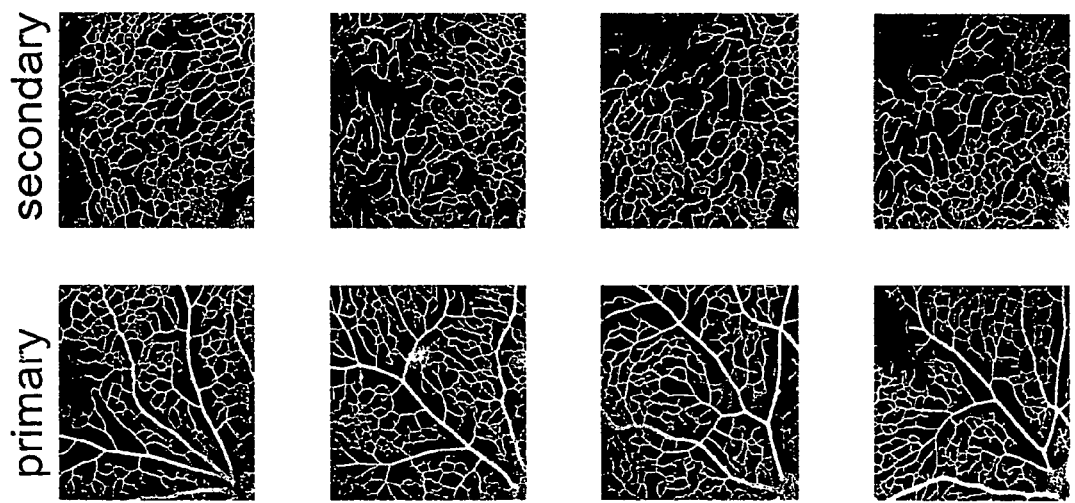

COMPOSITIONS AND METHODS FOR TREATMENT OF NEOVASCULAR DISEASES

CROSS-REFERENCE TO RELATED APPLICATIONS

This application claims the benefit of United States Provisional Application for Patent Ser. No. 60/577,156 filed on Jun. 4, 2004, and claims the benefit of United States Provisional Application for Patent Ser. No. 60/585,273 filed on Jul. 1, 2004, and claims the benefit of United States Provisional Application for Patent Ser. No. 60/655,801 filed on Feb. 24, 2005, each of which is incorporated herein by reference.

STATEMENT OF GOVERNMENT INTEREST

A portion of the work described herein was supported by grant number EY11254 and grant number EY14174 from the National Institutes of Health. The United States Government has certain rights in this invention.

FIELD OF THE INVENTION

This invention relates to treatment of neovascular diseases, such as retinal neovascular diseases. More particularly this invention relates to methods of treating neovascular disease by administering a combination of angiostatic and antiangiogenic drugs to a patient, and to compositions for use in said methods.

BACKGROUND OF THE INVENTION

The vast majority of diseases that cause catastrophic loss of vision do so as a result of ocular neovascularization. For example, age related macular degeneration (ARMD) affects 12-15 million American over the age of 65 and causes visual loss in 10-15% of them as a direct effect of choroidal (subretinal) neovascularization. The leading cause of visual loss for Americans under the age of 65 is diabetes; 16 million individuals in the United States are diabetic and 40,000 per year suffer from ocular complications of the disease, often a result of retinal neovascularization. While laser photocoagulation has been effective in preventing severe visual loss in subgroups of high risk diabetic patients, the overall 10-year incidence of retinopathy remains substantially unchanged. For patients with choroidal neovascularization due to ARMD or inflammatory eye disease such as ocular histoplasmosis, photocoagulation, with few exceptions, is ineffective in preventing visual loss. While recently developed, non-destructive photodynamic therapies hold promise for temporarily reducing individual loss in patients with previously untreatable choroidal neovascularization, only 61.4% of patients treated every 3-4 months had improved or stabilized vision compared to 45.9% of the placebo-treated group.

ARMD and diabetic retinopathy are the leading causes of visual loss in industrialized nations and do so as a result of abnormal retinal neovascularization. Since the retina consists of well-defined layers of neuronal, glial, and vascular elements, relatively small disturbances such as those seen in vascular proliferation or edema can lead to significant loss of visual function. Inherited retinal degenerations, such as retinitis pigmentosa (RP), are also associated with vascular abnormalities, such as arteriolar narrowing and vascular atrophy. While significant progress has been made in identifying factors that promote and inhibit angiogenesis, no treatment is currently available to specifically treat ocular vascular disease.

Inherited degenerations of the retina affect as many as 1 in 3500 individuals and are characterized by progressive night blindness, visual field loss, optic nerve atrophy, arteriolar attenuation, altered vascular permeability and central loss of vision often progressing to complete blindness (Heckenlively, J. R., editor, 1988; *Retinitis Pigmentosa*, Philadelphia: JB Lippincott Co.). Molecular genetic analysis of these diseases has identified mutations in over 110 different genes accounting for only a relatively small percentage of the known affected individuals (Humphries et al., 1992, *Science* 256:804-808; Farrar et al. 2002, *EMBO J.* 21:857-864.). Many of these mutations are associated with enzymatic and structural components of the phototransduction machinery including rhodopsin, cGMP phosphodiesterase, rds peripherin, and RPE65. Despite these observations, there are still no effective treatments to slow or reverse the progression of these retinal degenerative diseases. Recent advances in gene therapy have led to successful reversal of the rds (Ali et al. 2000, *Nat. Genet.* 25:306-310) and rd (Takahashi et al. 1999, *J. Virol.* 73:7812-7816) phenotypes in mice and the RPE65 phenotype in dogs (Acland et al. 2001, *Nat. Genet.* 28:92-95) when the wild type transgene is delivered to photoreceptors or the retinal pigmented epithelium (RPE) in animals with a specific mutation.

Angiogenesis is the process by which new blood vessels form. In response to specific chemical signals, capillaries sprout from existing vessels, eventually growing in size as needed by the organism. Initially, endothelial cells, which line the blood vessels, divide in a direction orthogonal to the existing vessel, forming a solid sprout. Adjacent endothelial cells then form large vacuoles and the cells rearrange so that the vacuoles orient themselves end to end and eventually merge to form the lumen of a new capillary (tube formation).

Angiogenesis is stimulated by a number of conditions, such as in response to a wound, and accompanies virtually all tissue growth in vertebrate organisms such as mammals. Angiogenesis also plays a role in certain disease states such as certain cancers. The growth of tumors, for example, requires blood vessel growth to provide oxygen and nutrients to the growing tumor tissue. In addition, ocular neovascularization is associated with the vast majority of eye diseases that lead to catastrophic loss of vision.

Angiogenesis may be arrested or inhibited by interfering with the chemical signals that stimulate the angiogenic process. For example, angiogenic endothelial cells produce proteases to digest the basal lamina that surround the blood vessels, thus clearing a path for the new capillary. Inhibition of these proteases, or their formation, can prevent new vessels from forming. Likewise, the endothelial cells proliferate in response to chemical signals. Particularly important proliferation signals include the vascular endothelial growth factor (VEGF), and the fibroblast growth factor (FGF) families of proteins. VEGF has been shown to be involved in vascularization of certain tumors. Interference with these proliferation signaling processes can also inhibit angiogenesis.

Several factors are involved in angiogenesis. Both acidic and basic fibroblast growth factor molecules are mitogens for endothelial cells and other cell types. A highly selective mitogen for vascular endothelial cells is VEGF.

In the normal adult, angiogenesis is tightly regulated, and is limited to wound healing, pregnancy and uterine cycling. Angiogenesis is turned on by specific angiogenic molecules such as basic and acidic fibroblast growth factor (FGF), VEGF, angiogenin, transforming growth factor (TGF), tumor necrosis factor-α (TNF-α) and platelet derived growth factor (PDGF). Angiogenesis can be suppressed by inhibitory molecules such as interferon-α, thrombospondin-1, angiostatin and endostatin. It is the balance of these naturally occurring stimulators and inhibitors that controls the normally quiescent capillary vasculature. When this balance is upset, as in certain disease states, capillary endothelial cells are induced to proliferate, migrate and ultimately differentiate.

Angiogenesis plays a central role in a variety of disease including cancer and ocular neovascularization. Sustained growth and metastasis of a variety of tumors has also been shown to be dependent on the growth of new host blood vessels into the tumor in response to tumor derived angiogenic factors. Proliferation of new blood vessels in response to a variety of stimuli occurs as the dominant finding in the majority of eye disease and that blind including proliferative diabetic retinopathy, ARMD, rubeotic glaucoma, interstitial keratitis and retinopathy of prematurity. In these diseases, tissue damage can stimulate release of angiogenic factors resulting in capillary proliferation. VEGF plays a dominant role in iris neovascularization and neovascular retinopathies. While reports clearly show a correlation between intraocular VEGF levels and ischemic retinopathic ocular neovascularization, FGF likely plays a role as well. Basic and acidic FGF are known to be present in the normal adult retina, even though detectable levels are not consistently correlated with neovascularization. This may be largely due to the fact that FGF binds very tightly to charged components of the extracellular matrix and may not be readily available in a freely diffusible form that would be detected by standard assays of intraocular fluids.

A final common pathway in the angiogenic response involves integrin-mediated information exchange between a proliferating vascular endothelial cell and the extracellular matrix. This class of adhesion receptors, called integrins, are expressed as heterodimers having an α and β subunit on all cells. One such integrin, $\alpha_v\beta_3$, is the most promiscuous member of this family and allows endothelial cells to interact with a wide variety of extracellular matrix components. Peptide and antibody antagonists of this integrin inhibit angiogenesis by selectively inducing apoptosis of the proliferating vascular endothelial cells. Two cytokine-dependent pathways of angiogenesis exist and may be defined by their dependency on distinct vascular cell integrins, $\alpha_v\beta_3$ and $\alpha_v\beta_5$. Specifically, basic FGF- and VEGF-induced angiogenesis depend on integrin $\alpha_v\beta_3$ and $\alpha_v\beta_5$, respectively, since antibody antagonists of each integrin selectively block one of these angiogenic pathways in the rabbit corneal and chick chorioallantoic membrane (CAM) models. Peptide antagonists that block all $\alpha_v$ integrins inhibit FGF- and VEGF-stimulated angiogenesis. While normal human ocular blood vessels do not display either integrin, $\alpha_v\beta_3$ and $\alpha_v\beta_5$ integrins are selectively displayed on blood vessels in tissues from patients with active neovascular eye disease. While only $\alpha_v\beta_3$ was consistently observed in tissue from patients with ARMD, $\beta_v\beta_3$ and $\alpha_v\beta_5$ both were present in tissues from patients with proliferative diabetic retinopathy. Systemically administered peptide antagonists of integrins blocked new blood vessel formation in a mouse model of retinal vasculogenesis.

Hence, anti-angiogenic agents have a role in treating retinal degeneration to prevent the damaging effects of these trophic and growth factors. Angiogenic agents, also have role in promoting desirable vascularization to retard retinal degeneration by enhancing blood flow to cells.

Immense research efforts have contributed to our understanding of the mechanisms of angiogenesis during disease progression, and as a result of these studies, a large number of angiostatic molecules have been, or are currently being, tested in clinical trials. However, to date, the results from these clinical trials have been disappointing, and the benefits from these antiangiogenic treatments in patients have been minimal at best.

Many factors may require consideration before angiostatic therapies ultimately become successful. Naturally occurring compensatory mechanisms may ultimately render angiogenic monotherapies obsolete. Angiostatic drugs generally target a single cytokine or intracellular angiogenic pathway. In vivo, angiogenesis is likely to be initiated by the combined signaling of multiple pathways. Thus, blocking a single pathway may be insufficient to prevent angiogenesis during the treatment of neovascular diseases. Further complicating matters, it is also likely that blocking a single pathway induces compensation and increased roles of other angiogenic pathways.

It has now been discovered that a concurrent administration of a combination of angiostatic compounds that target different pathways enhances angiostatic potency and also interferes with natural compensatory mechanisms.

SUMMARY OF THE INVENTION

The present invention provides compositions and a method of treating a neovascular disease, such as a retinal neovascular disease, by administering to a mammal suffering from a neovascular disease an amount of a combination of angiogenesis suppressing drugs sufficient to inhibit new blood vessel formation. These drugs can be a combination of an angiostatic fragment of tryptophanyl-tRNA synthetase (TrpRS) and a therapeutic agent. Preferably, the therapeutic agent is a VEGF signaling inhibitor, an integrin signaling inhibitor, or a combination thereof. Additionally, the therapeutic agent can comprise an angiostatic steroid, an anti-neoplastic agent, an anti-bacterial agent, an anti-viral agent, and an anti-inflammatory agent, and the like. Preferably the mammal is a human.

A particularly preferred method embodiment comprises administering to a mammal suffering from a neovascular disease a vascular development inhibiting amount of an admixture of drugs comprising an angiostatic fragment of TrpRS (e.g., the T1 fragment, the T2 fragment, or the mini TrpRS fragment described herein) and at least one compound selected from a VEGF signaling inhibitor and an integrin signaling inhibitor. Another preferred embodiment for this purpose is the triple combination of T2-TrpRS angiostatic fragment, aVEGF signaling inhibitor such as a VEGF aptamer, and an integrin signaling inhibitor such as an $\alpha_v\beta_3$ and $\alpha_v\beta_5$ integrin signaling inhibitor. A particularly preferred triple combination comprises the T2 fragment of human TrpRS, a VEGF aptamer specific for VEGF-165 (e.g., pegaptanib sodium), and a peptidomimetic $\alpha_v\beta_3$ and $\alpha_v\beta_5$ integrin signaling inhibitor (e.g., Compound (1) described herein). This particular triple combination exhibits a strong synergistic effect on the inhibition of neovascularization in the mammalian eye.

Neovascular diseases treatable by the methods of the present invention include, without limitation, ocular diseases such as retinal degenerative diseases, retinal vascular degenerative diseases, ischemic retinopathies, vascular hemorrhages, vascular leakage, and choroidopathies in neonatal, juvenile, or fully mature mammals. The methods of the present invention can also be utilized to treat neovascular diseases such as solid tumor cancers (e.g., lung cancer, breast cancer, and prostate cancer) and rheumatoid arthritis, for example.

A therapeutic composition useful for inhibition of angiogenesis, and thus for the treatment of neovascular diseases, comprises an admixture of an angiostatic fragment of tryptophanyl-tRNA synthetase (TrpRS), a VEGF signaling inhibitor, and an integrin signaling inhibitor, together with a pharmaceutically acceptable excipient and a carrier therefor. Optionally the present therapeutic compositions can also include one or more of an angiostatic steroid, an anti-neoplastic agent, an anti-bacterial agent, an anti-viral agent, an anti-inflammatory agent, and the like therapeutic agents.

BRIEF DESCRIPTION OF THE DRAWINGS

FIG. 1 depicts the amino acid sequences of an angiostatic fragments of tryptophanyl-tRNA synthetase designated as T2-TrpRS, SEQ ID NO: 1 and T2-TrpRS-GD, SEQ ID NO: 2 (a mutant thereof).

FIG. 2 depicts the amino acid sequence of an angiostatic fragments of tryptophanyl-tRNA synthetase designated as mini-TrpRS, SEQ ID NO: 3 and T1-TrpRS, SEQ ID NO: 4.

FIG. 3 depicts the amino acid sequence of full length TrpRS (SEQ ID NO: 5) and indicates the position of the T1, T2 and Mini fragments thereof.

FIG. 11 depicts photomicrographs of primary and secondary vascular layers of retinas of mice from Example 3 intravitreally injected with a 1× concentration of T2-TrpRS.

FIG. 15 depicts photomicrographs of primary and secondary vascular layers of retinas of mice from Example 4 intravitreally injected with a 1× concentration of T2-TrpRS.

FIG. 22 depicts photomicrographs of primary and secondary vascular layers of retinas of control mice from Example 6 intravitreally injected with PBS.

FIG. 23 depicts photomicrographs of primary and secondary vascular layers of retinas of mice from Example 6 intravitreally injected with a 1× concentration of T2-TrpRS.

FIG. 24 depicts photomicrographs of primary and secondary vascular layers of retinas of mice from Example 6 intravitreally injected with a 1× concentration of VEGF aptamer Compound (2).

FIG. 25 depicts photomicrographs of primary and secondary vascular layers of retinas of mice from Example 6 intravitreally injected with a 0.5× concentration of peptidomimetic integrin signaling inhibitor Compound (1).

FIG. 26 depicts photomicrographs of primary and secondary vascular layers of retinas of mice from Example 6 intravitreally injected with a combination of a 1× concentration of T2-TrpRS and a 1× concentration of VEGF aptamer Compound (2).

FIG. 27 depicts photomicrographs of primary and secondary vascular layers of retinas of mice from Example 6 intravitreally injected with a combination of a 1× concentration of T2-TrpRS and a 0.5× concentration of peptidomimetic integrin signaling inhibitor Compound (1).

FIG. 28 depicts photomicrographs of primary and secondary vascular layers of retinas of mice from Example 6 intravitreally injected with a combination of a 1× concentration of T2-TrpRS, a 0.5× concentration of peptidomimetic integrin signaling inhibitor Compound (1), and a normal concentration of VEGF aptamer Compound (2).

FIG. 31 depicts photomicrographs of primary and secondary vascular layers of retinas of mice from Example 7 intravitreally injected with a 1× concentration of VEGF aptamer Compound (2).

FIG. 32 depicts photomicrographs of primary and secondary vascular layers of retinas of mice from Example 7 intravitreally injected with a 0.5× concentration of peptidomimetic integrin signaling inhibitor Compound (1).

FIG. 34 depicts photomicrographs of primary and secondary vascular layers of retinas of mice from Example 7 intravitreally injected with a combination of a 1× concentration of T2-TrpRS, a 0.5× concentration of peptidomimetic integrin signaling inhibitor Compound (1), and a 1× concentration of VEGF aptamer Compound (2).

FIG. 35 depicts photomicrographs of primary and secondary vascular layers of retinas of control mice from Example 9 intravitreally injected with PBS.

DETAILED DESCRIPTION OF PREFERRED EMBODIMENTS

A composition suitable for treating a neovascular disease comprises an angiostatic fragment of tryptophanyl-tRNA synthetase (TrpRS) and a therapeutic agent. Preferably the therapeutic agent comprises at least one anti-angiogenic agent selected from the group consisting of a VEGF signaling inhibitor (E.g, a VEGF aptamer) and an integrin signaling inhibitor (e.g., angiostatic integrin antagonist).

Preferred angiostatic fragments of TrpRS include a 43 kDa fragment (e.g., the T2 fragment, "T2-TrpRS", SEQ ID NO: 1; a mutant of T2-TrpRS, "T2-TrpRS-GD", SEQ ID NO: 2; both of which are shown in FIG. 1), a 48 kDa fragment such as the truncated TrpRS known as mini-TrpRS (SEQ ID NO: 3, shown in FIG. 2), and a 46 kDa fragment such as the truncated TrpRS known as T1-TrpRS (SEQ ID NO: 4, shown in FIG. 2). The amino acid residue sequence of T2-TrpRS-GD (SEQ ID NO: 2), differs from SEQ ID NO: 1 by two amino acid residue substitutions (i.e., S121G and Y122D). The amino acid residue sequence of full length human TrpRS (SEQ ID NO: 5) is shown in FIG. 3, along with an indication of the position of the T1, T2 and mini fragments thereof. Without being bound by theory, it is believed that the angistatic fragments of TrpRS can form non-covalent dimers (see e.g., Yu et al. *J. Biol. Chem.* 2004, 279: 8378-8388), which may contribute to the biological activity of the fragments. Accordingly, any reference herein an in the appended claims to an angiostatic fragment of TrpRS (e.g., T1-TRpRS, T2-TrpRS, mini-TrpRS) is to be construed as a reference to the monomer form, the dimer form, or a mixture thereof.

Preferred integrin signaling inhibitors are $\alpha_v\beta_3$ and $\alpha_v\beta_5$ antagonists, including RGD peptides, such as those described in U.S. Pat. Nos. 5,693,612 5,766,591, 5,767,071, 5,780,426, and 6,610,826, the relevant disclosures of which are incorporated herein by reference, and peptidomimetic integrin antagonists such as those described in U.S. Pat. Nos. 5,614,531, 5,614,535, 6,326,403, 6,455,529, 6,521,646, 6,559,144, 6,576,637, 6,602,876, 6,645,991, and 6,649,613, the relevant disclosures of which are incorporated herein by reference. A particularly preferred peptidomimetic integrin signaling inhibitor is a compound having the formula of Compound (1), available from Merck KGaA (Darmstadt, Germany) as EMD 472523.

Compound (1)

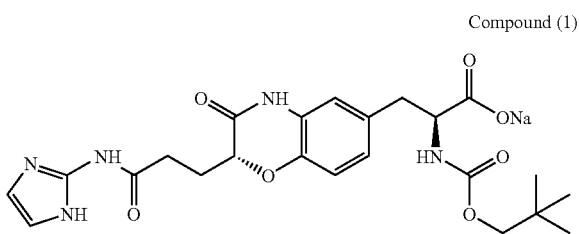

Figure 59:
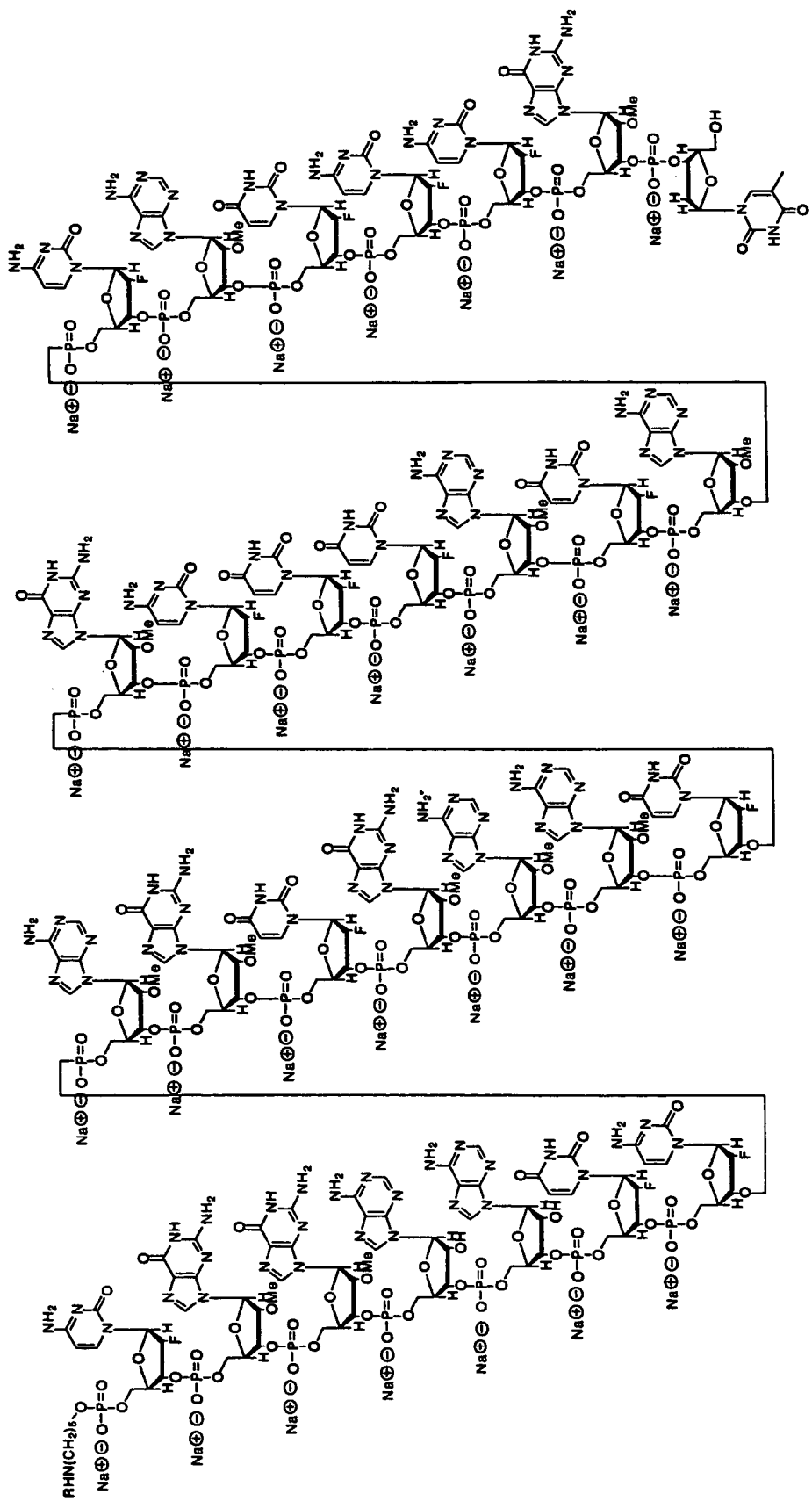
FIG. 59 shows the structure of VEGF aptamer Compound (2) (SEQ ID NO: 6), pegaptanib sodium.

Preferred VEGF signaling inhibitors include VEGF-selective aptamers (protein binding oligonucleotides), preferably nuclease resistant aptamers that bind to VEGF-165, such as the 2'-fluoropyrimidine RNA-based aptamers that bind to VEGF-165 described by Ruckman et al. *J. Biol. Chem.* 1998, 273: 20556-20567 (the relevant disclosure of which is incorporated herein by reference), and the like; anti-VEGF antibodies and fragments thereof that bind to VEGF, such as the Rhu antibody available from Genentech (San Francisco, Calif.) and an Fab fragment thereof (RhuFab V2); soluble VEGF receptors such as soluble VEGFR1; and small interfering RNAs (siRNA) that target VEGF or its receptors, such as the siRNA described by Reich et al. *Mol. Vis.* 2003; 9:210-216 (the relevant disclosure of which is incorporated herein by reference). Preferred VEGF signaling inhibitors are nuclease resistant VEGF aptamers, more preferably 2'-fluoropyrimidine RNA-based aptamers specific for VEGF-165, such as pegaptanib sodium (Compound (2)), which is a polyethoxylated oligonucleotide having the following formula (SEQ ID NO: 6; FIG. 59, R in FIG. 59 is a 40 kiloDalton polyethylene glycol (PEG) chain):

5'-40K PEG-C5 aminolinker-CfGmGmArArUfCfAmG-mUfGmAmUfGmCfUf UfAmUfAmCfAmUfCfCfGm3'-3'dT wherein

| | |
|---|---|
| Cf = 2'fluoro C | Ar = 2' OH (ribo) A |
| Uf = 2'fluoro U | 3'-3'dT = inverted deoxyT |
| Am = 2'OMe A | C5 aminolinker = pentyl amino linker |
| Gm = 2'OMe G | 40K PEG = 40K polyethelene glycol amide. |

A polyethoxylated oligonucleotide of SEQ ID NO: 6 is sold commercially under the trademark MACUGEN® by from Eyetech Pharmaceuticals, Inc., and is also known as NX1838 or pegaptanib sodium.

In one embodiment the combination of drugs also includes at least one additional therapeutic agent such as an angiostatic steroid, an anti-neoplastic agent, an anti-bacterial agent, an anti-viral agent, an anti-inflammatory agent, and the like.

Examples of suitable angiostatic steroids include anecortave acetate and triamcinolone acetonide.

Examples of suitable anti-neoplastic agents include Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Imofosine; Interferon Alfa-2a; Interferon Alfa-2b; Interferon Alfa-nl; Interferon Alfa-n3; Interferon Beta-Ia; Interferon Gamma-Ib; Iproplatin; Irinotecan Hydrochloride; Lanreotide Acetate; Letrozole; Leuprolide Acetate Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; and Zinostatin; Zorubicin Hydrochloride.

Examples of suitable anti-bacterial agents include, but are not limited to, penicillins, aminoglycosides, macrolides, monobactams, rifamycins, tetracyclines, chloramphenicol, clindamycin, lincomycin, imipenem, fusidic acid, novobiocin, fosfomycin, fusidate sodium, neomycin, polymyxin, capreomycin, colistimethate, colistin, gramicidin, minocycline, doxycycline, vanomycin, bacitracin, kanamycin, gentamycin, erythromicin and cephalosporins.

Examples of suitable anti-inflammatory agents include, but are not limited to, aspirin (acetylsalicylic acid), indomethacin, sodium indomethacin trihydrate, salicylamide, naproxen, colchicine, fenoprofen, sulindac, diflunisal, diclofenac, indoprofen and sodium salicylamide.

Examples of suitable anti-viral agents include, but are not limited to, alpha-methyl-P-adamantane methylamine, 1-D-ribofuranosyl-1,2,4-triazole-3 carboxamide, 9-(2-hydroxyethoxy)methylguanine, adamantanamine, 5-iodo-2'-deoxyuridine, trifluorothymidine, interferon, adenine arabinoside, CD4, 3'-azido-3'-deoxythymidine (AZT), 9-(2-hydroxyethoxymethyl)-guanine (acyclovir), phosphonoformic acid, 1-adamantanamine, peptide T, and 2',3'dideoxycytidine.

A particularly preferred method of treating neovascular diseases comprises administering to a mammal suffering from a neovascular disease a vascular development inhibiting amount of a combination of drugs comprising T2-TrpRS, at least one VEGF-165 signaling inhibitor, and optionally, at least one $\alpha_v\beta_3$ and $\alpha_v\beta_5$ integrin signaling inhibitor.

Neovascular diseases treatable by the methods of the present invention include, without limitation, neovascular diseases of the eye (e.g., retinal and choroidal neovascular diseases), rubeotic glaucoma, pterygia, solid tumor cancers (e.g., lung cancer, breast cancer, and prostate cancer), osteoarthritis, rheumatoid arthritis, vascular anomalies and malformations (e.g., hemangiomas, lymphangiomas, and the like), and psoriasis.

The present method of treating retinal neovascular diseases in a mammal preferably comprises intravitreally injecting into the eye of a mammal suffering from a neovascular disease a vascular development inhibiting amount of a combination of antiangiogenic and angiostatic compositions that provide an angiostatic fragment of TrpRS, a VEGF signaling inhibitor, and an integrin signaling inhibitor.

This method can be utilized to treat ocular diseases such as vascular degenerative diseases, ischemic retinopathies, vascular hemorrhages, vascular leakage, and choroidopathies in neonatal, juvenile or fully mature mammals. Examples of such diseases include age related macular degeneration, diabetic retinopathy, presumed ocular histoplasmosis, retinopathy of prematurity, sickle cell anemia, hemangioma, pterygia, ischemic central retinal vein occlusion, blanch retinal vein occlusion, ocular melanoma, retinal blastoma, and retinitis pigmentosa, as well as retinal injuries.

Another aspect of the present invention is a therapeutic composition useful for the treatment of neovascular diseases, which comprises an angiostatic fragment of TrpRS, a VEGF signaling inhibitor, and an integrin signaling inhibitor, together with one or more pharmaceutically acceptable excipient.

In a preferred embodiment, the composition further comprises at least one additional therapeutic agent such as an angiostatic steroid, an anti-neoplastic agent, an anti-bacterial agent, an anti-viral agent, an anti-inflammatory agent, and the like.

A method of treating a neovascular disease comprises administering to a mammal suffering from a neovascular disease a vascular development inhibiting amount of a combination of drugs comprising an angiostatic fragment of tryptophanyl-tRNA synthetase (TrpRS) and at least one compound selected from the group consisting of a vascular endothelial growth factor (VEGF) signaling inhibitor and an integrin signaling inhibitor.

Generally, a vascular development inhibiting amount of a composition of the present invention is at least about 10 μg/kg body weight and, in most cases, not in excess of about 8 mg/kg body weight per day for systemic treatments. Preferably the dosage is in the range of about 10 μg/kg body weight to about 1 mg/kg body weight daily. For ocular, intravitreal treatment of human patients, the preferred dosage is in the range of about 0.1 to about 5 milligrams per eye for a given treatment. The compositions may be administered in a single dose or in multiple doses over time. One of ordinary skill in the medical arts would be capable of determining the optimum effective therapeutic dosage of a composition of the present invention, taking into account the particular patient, the drugs present in the composition, the disease state, and other factors that are well known in the medical arts.

The therapeutic compositions of this invention can be embodied in a variety of physical forms. These forms include, for example, solid, semi-solid, and liquid dosage forms, such as tablets, pills, powders, liquid solutions or suspensions, aerosols, liposomes, suppositories, injectable and infusible solutions and sustained release forms. One of ordinary skill in the medical arts will choose a suitable dosage form depending on the intended mode of administration and on the disease to be treated, using pharmacological principles well known in the art.

A therapeutic composition according to this invention can be administered by conventional routes of administration, such as parenteral, subcutaneous, intravenous, intramuscular, intralesional, intrasternal, intravitreal, intracranial, or aerosol routes. Topical routes of administration can also be used, with application of the compositions locally to a particular part of the body (e.g., eye, skin, lower intestinal tract, vagina, rectum) where appropriate. The therapeutic compositions also include conventional pharmaceutically acceptable carriers and excipients that are known to those of skill in the art.

Generally, the therapeutic compositions of the present invention can be formulated and administered using methods and compositions similar to those used for the individual classes of active ingredients present in the compositions. It will be understood by those of skill in the art that conventional doses will vary depending upon the particular active ingredients in the composition, as well as the patient's health, weight, age, sex, the condition or disease, and the desired mode of administration.

The therapeutic compositions of this invention include pharmacologically appropriate, pharmaceutically acceptable carriers, excipients and vehicles. In general, these carriers include aqueous or alcoholic/aqueous solutions, emulsions or suspensions, including saline and buffered media such as phosphate buffered saline (PBS). Parenteral vehicles can include sodium chloride solution, Ringer's dextrose, dextrose and sodium chloride, lactated Ringer's or fixed oils. In addition, intravenous vehicles can include fluid and nutrient replenishers, and electrolyte replenishers, such as those based on Ringer's dextrose. Excipients such as preservatives and other additives can also be present, such as, for example, antimicrobials, antioxidants, chelating agents, and inert gases. Suitable formulation aids, carriers, other excipients, and methods of formulating pharmaceutical compositions are disclosed in *Remington's Pharmaceutical Sciences,* 14th Ed., Mack Publishing Co., 1970, particularly Part VIII, "Pharmaceutical Preparations and Their Manufacture", pages 1461-1762, the relevant disclosures of which are incorporated herein by reference.

The therapeutic compositions of the present invention can be packaged in suitably sterilized bottles or vials, either in multi-dose or in unit dose forms. The containers are preferably hermetically sealed after being filled with a composition of the invention. Preferably, the compositions are packaged in a container having a label affixed thereto, which label identifies the drugs present in the composition, and bears a notice in a form prescribed by a government agency such as the United States Food and Drug Administration, reflecting approval of the composition under appropriate laws, dosage information, and the like. The label preferably contains information about the composition that is useful to a health care professional administering the composition to a patient. The package also preferably contains printed informational materials relating to the administration of the composition, instructions, indications, and any necessary required warnings.

Methods

Neonatal Mouse Retinal Angiogenesis Model

Description of the Model. Immediately after birth (postnatal day zero; "P0"), retinal vasculature is virtually absent in the mouse. By four weeks after birth (P28) the retina has attained an adult pattern of retinal vessels coincident with the onset of vision. Physiological neovascularization of the retina occurs during this period via a stereotypical, biphasic developmental pattern of angiogenesis. During the primary phase of retinal vascular development, spoke-like peripapillary vessels grow radially from the central retinal artery and vein, becoming progressively interconnected by a capillary plexus that forms between them. This "inner retinal plexus" grows in area, volume and complexity, centrifugally, as a monolayer within the nerve fiber layer during the first seven to ten days following birth.

The second phase of retinal vessel formation begins between postnatal days 7 (P7) and 10 (P10) when collateral branches sprout from capillaries of the superficial plexus and penetrate into the retina where their tips branch and anastamose laterally to form a planar "deep vascular plexus". While the deep vascular plexus is in place by P14, it undergoes extensive remodeling from P14 to P21. It is of interest to note that the formation of these vascular networks in the neonatal mouse are strikingly similar to the events occurring in the third trimester human fetus.

Advantages and Quantification of the Model. The reproducibility of the murine retinal development process and its easy accessibility in neonatal animals provide an opportunity to assess the efficacy of antiangiogenic compounds in a physiologically relevant model of angiogenesis. Additional advantages of the neonatal mouse model are the ability to qualitatively and quantitatively evaluate the angiostatic effect of putative antagonists of angiogenesis. Angiostatic activity was evaluated based upon the degree of angiogenesis in the deep, outer retinal vascular layer (secondary layer) that develops between P8 and P12. The appearance of the inner blood vessel network (primary layer) was evaluated for normal development and signs of toxicity. No abnormalities in the inner vascular layer were observed in any of the assays performed and described herein. Qualitative evaluation of the secondary layer vascularization can be performed by microscopically photographing appropriately stained superficial and deep layers of excised retinas and determining the percentage of eyes in which formation of the deep vascular layer is completely or partially inhibited. All data presented herein are based on qualitative analysis of the percentage of eyes that demonstrated a 75 to 100% inhibition of deep retinal vascular network formation after treatment. In most cases, the percentage of mice that exhibited >95% and 100% inhibition of deep retinal vascular network formation are also provided.

Preparation of Compositions. Peptidomimetic integrin signaling inhibitor Compound (1) is solubilized in PBS at a concentration of about 20 mg/ml in PBS (1× concentration). T2-TrpRS is solubilized in PBS at a concentration of about 0.5 mg/ml (1× concentration). VEGF aptamer (pegaptanib sodium; Compound (2)) is solubilized in PBS at a concentration of about 2 mg/ml (1× concentration) to achieve an injection of approximately 1 μg/eye at 1× concentration. For all combination assays the compounds were prepared at 2 or 3 times the 1× concentration of each material and then combined to produce a final solution containing each individual compound at the same concentration as was used alone (e.g., 1×, 0.5×, 0.25× or 0.1×, as the case may be). For all assays, a single injection of 0.5 μl of PBS solutions of the drugs was administered intravitreally regardless of the number of compounds being injected. As used herein, the term "0.1×" refers to one tenth of the 1× concentration of a given material, "0.25×" refers to one quarter of the 1× concentration of a given material, "0.5×" refers to one half of the 1× concentration of a given material, and so forth for similar designations.

Mouse model of Oxygen Induced Retinopathy (OIR). This model is described by Smith, L., *Invest. Ophthalmol. Vis. Sci.* 35, 101-111 (1994). Mice are placed in hyperoxia (75% $O_2$) from P7-P 12, followed by return to normoxia. While under hyperoxia, the central retinal vessels obliterate, and deep vasculature fails to form. Upon return to normoxia, the retina becomes hypoxic and pathological neovascularization results.

Quantification of neovascularization in the OIR model involved quantification of enovascular tuft formation, as well as quantification of obliteration. Retinal whole mounts are prepared and blood vessels thereof are stained with isolectin $GS-IB_4$. Confocal imaging, focusing just above the superficial vascular plexus, is carried out and a montage of four quadrants is made. Neovascular tufts are identified (Adobe PHOTOSHOP®) and the area of pixelation is quantified. In addition, areas of obliteration are traced (Adobe PHOTOSHOP®), and the area of pixelation is quantified. Conversion factor based on image acquisition (resolution, size etc.) is then applied to obtain a value in $\mu m^2$.

General Angiogenesis Assay Procedure.

An in vivo angiogenesis assay in the neonatal mouse (Balb/C, The Jackson Laboratory, Bar Harbor, Me.) was used to evaluate the angiostatic activity of integrin signaling inhibitor Compound (1), T2-TrpRS, and VEGF aptamer Compound (2). Intravitreous injection and retina isolation was performed with a dissecting microscope (SMZ 645, Nikon, Japan). An eyelid fissure was created at postnatal day 7 (P7) with a fine blade to expose the globe for injection. The samples (0.5 μl) were injected with a Hamilton syringe fitted with a 32-gauge needle (Hamilton Company, Reno, Nev.). The injection was made between the equator and the corneal limbus. During injection, the location of the needle tip was monitored by direct visualization to determine that it was in the vitreal cavity. Eyes with needle-induced lens or retinal damage were excluded from the study. After the injection, the eyelids were repositioned to close the fissure.

On postnatal day 12 (P12), animals were euthanized and the eyes were enucleated. After about 10 minutes in 4% paraformaldehyde (PFA) the cornea, lens, sclera, and vitreous were excised through a limbal incision. The isolated retina was prepared for staining by soaking in methanol for about 10 minutes on ice, followed by blocking in 50% fetal bovine serum (Gibco, Grand Island, N.Y.) with 20% normal goat serum (The Jackson Laboratory, Bar Harbor, Me.) in PBS for about one hour on ice. The blood vessels were specifically visualized by staining the retina for about 18 hours at about 4° C. with a rabbit anti-mouse collagen IV antibody (Chemicon, Temecula, Calif.) diluted 1:200 in blocking buffer or with a fluorescent conjugated isolectin (*Griffonia simplicifolia*, Molecular Probes). An ALEXA FLUOR® (Alexa) 594-conjugated goat anti-rabbit IgG antibody (Molecular probes, Eugene, Oreg.) (1:200 dilution in blocking buffer) was incubated with the retina for about 2 hours at about 4° C. The retinas were then mounted for microscopic evaluation with slow-fade mounting media (Molecular Probes, Eugene, Oreg.).

EXAMPLE 1

Figure 4:
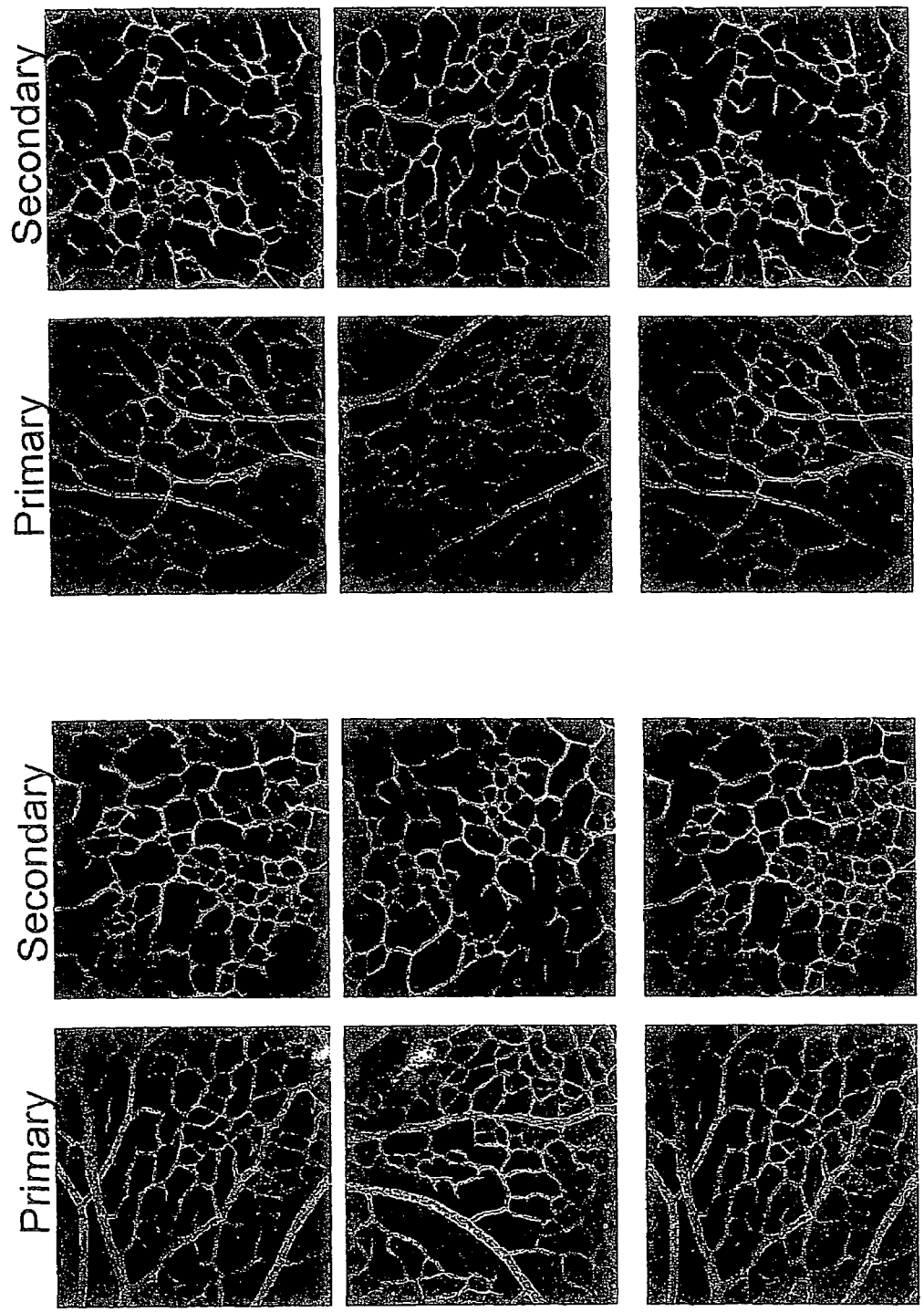
FIG. 4 depicts photomicrographs of primary and secondary vascular layers of retinas of control mice from Example 1 intravitreally injected with PBS.
Figure 5:
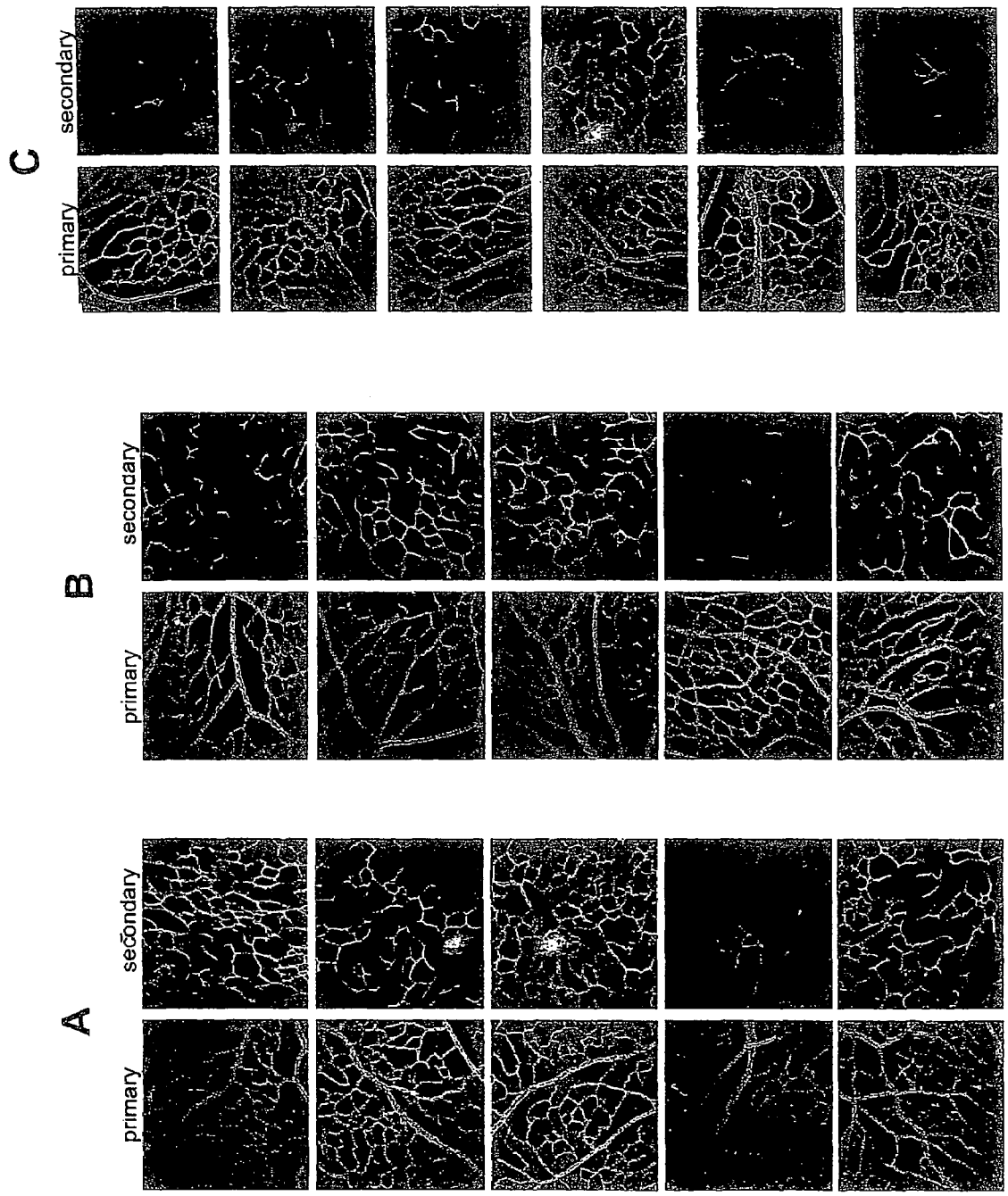
FIG. 5 depicts photomicrographs of primary and secondary vascular layers of retinas of mice from Example 1 intravitreally injected with (A) 0.5× concentration (10 mg/ml) of peptidomimetic integrin signaling inhibitor Compound (1); (B) a 1× concentration (2 mg/ml) of VEGF aptamer Compound (2); and (C) a combination of integrin signaling inhibitor Compound (1) and VEGF aptamer Compound (2).
Figure 6:
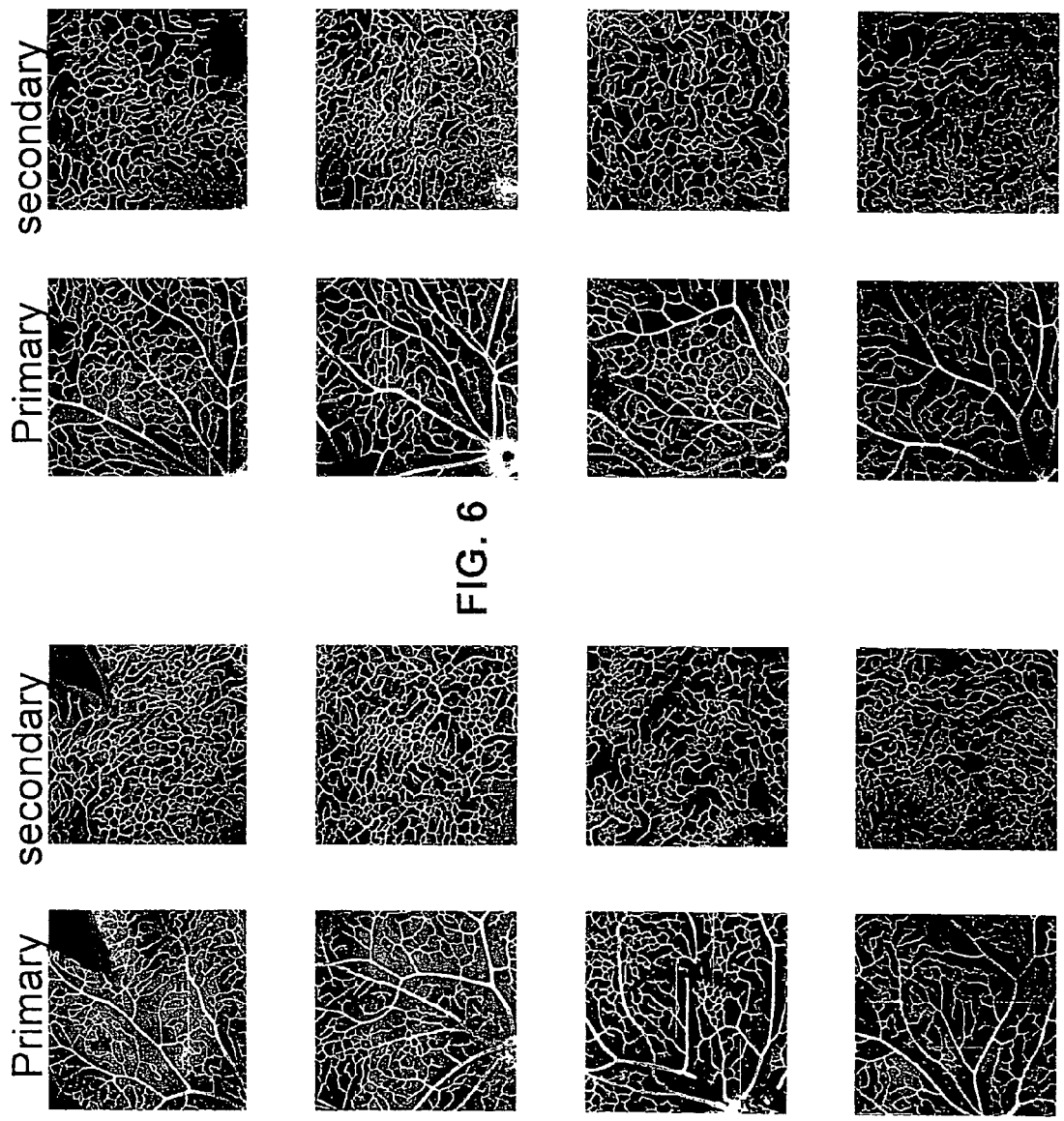
FIG. 6 depicts photomicrographs of primary and secondary vascular layers of retinas of control mice from Example 2 intravitreally injected with phosphate buffered saline (PBS).
Figure 7:
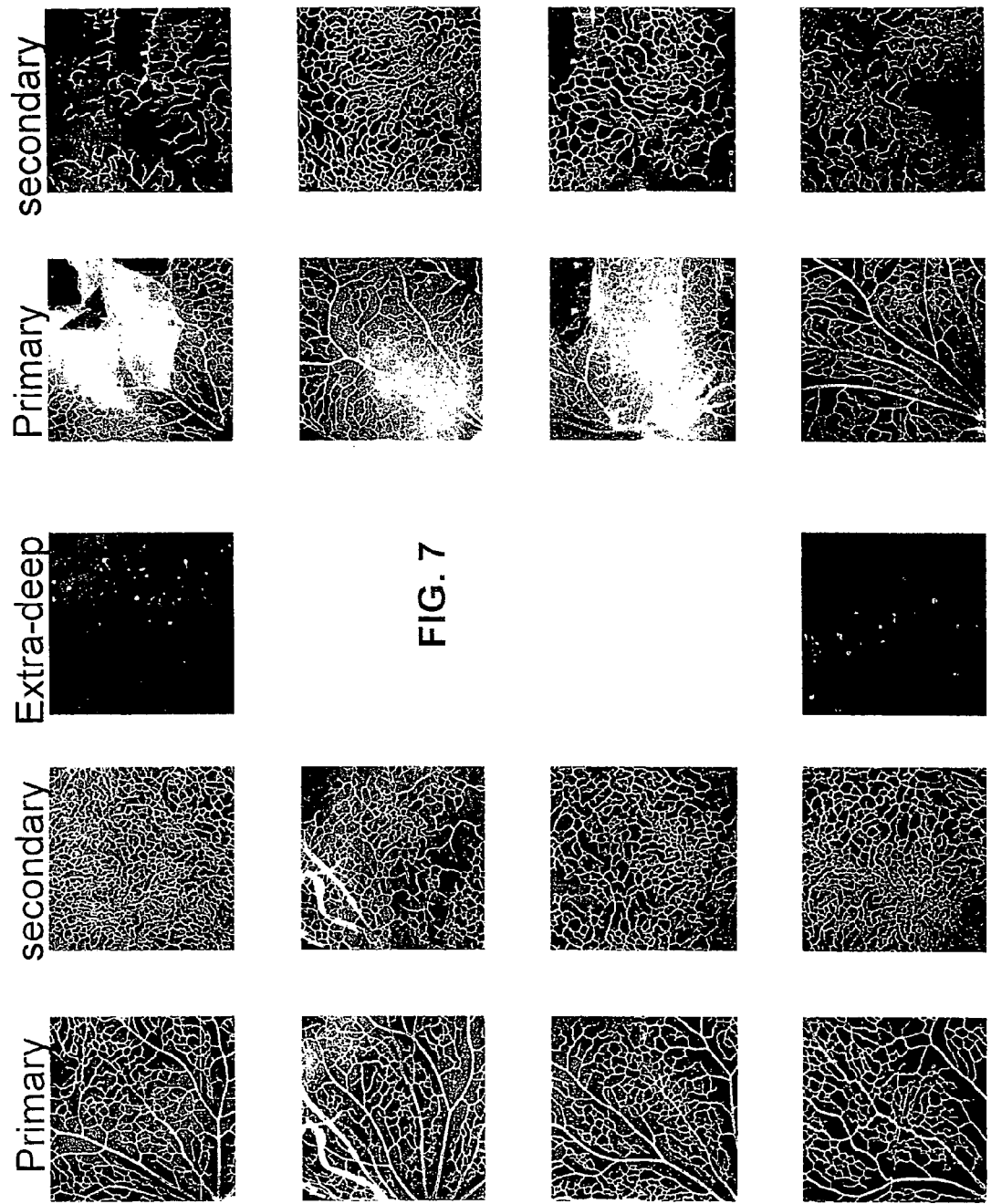
FIG. 7 depicts photomicrographs of primary and secondary vascular layers of retinas of mice from Example 2 intravitreally injected with 0.1× concentration (0.05 mg/ml) of T2-TrpRS.
Figure 8:
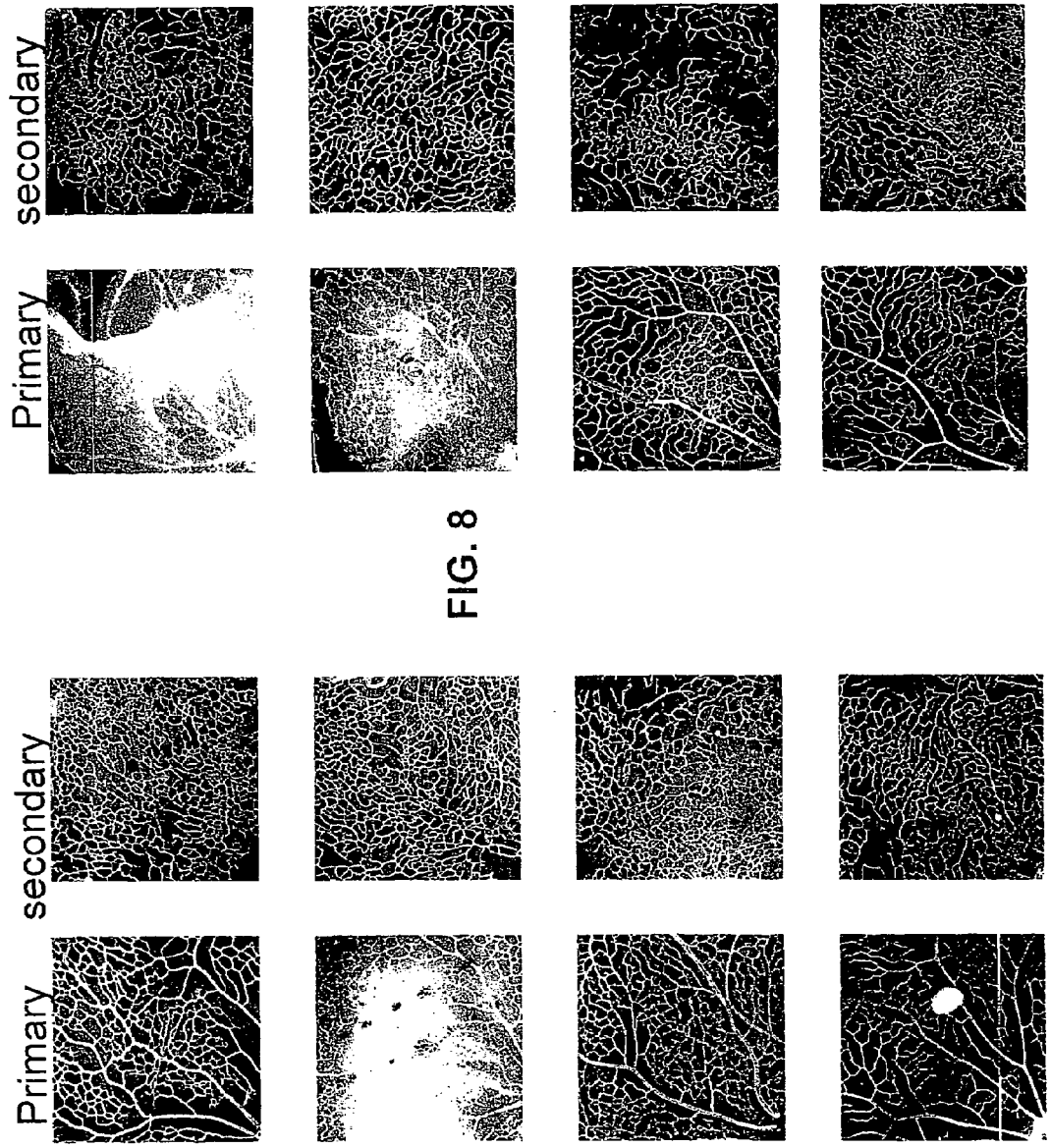
FIG. 8 depicts photomicrographs of primary and secondary vascular layers of retinas of mice from Example 2 intravitreally injected with 0.1× concentration of VEGF aptamer Compound (2).
Figure 9:
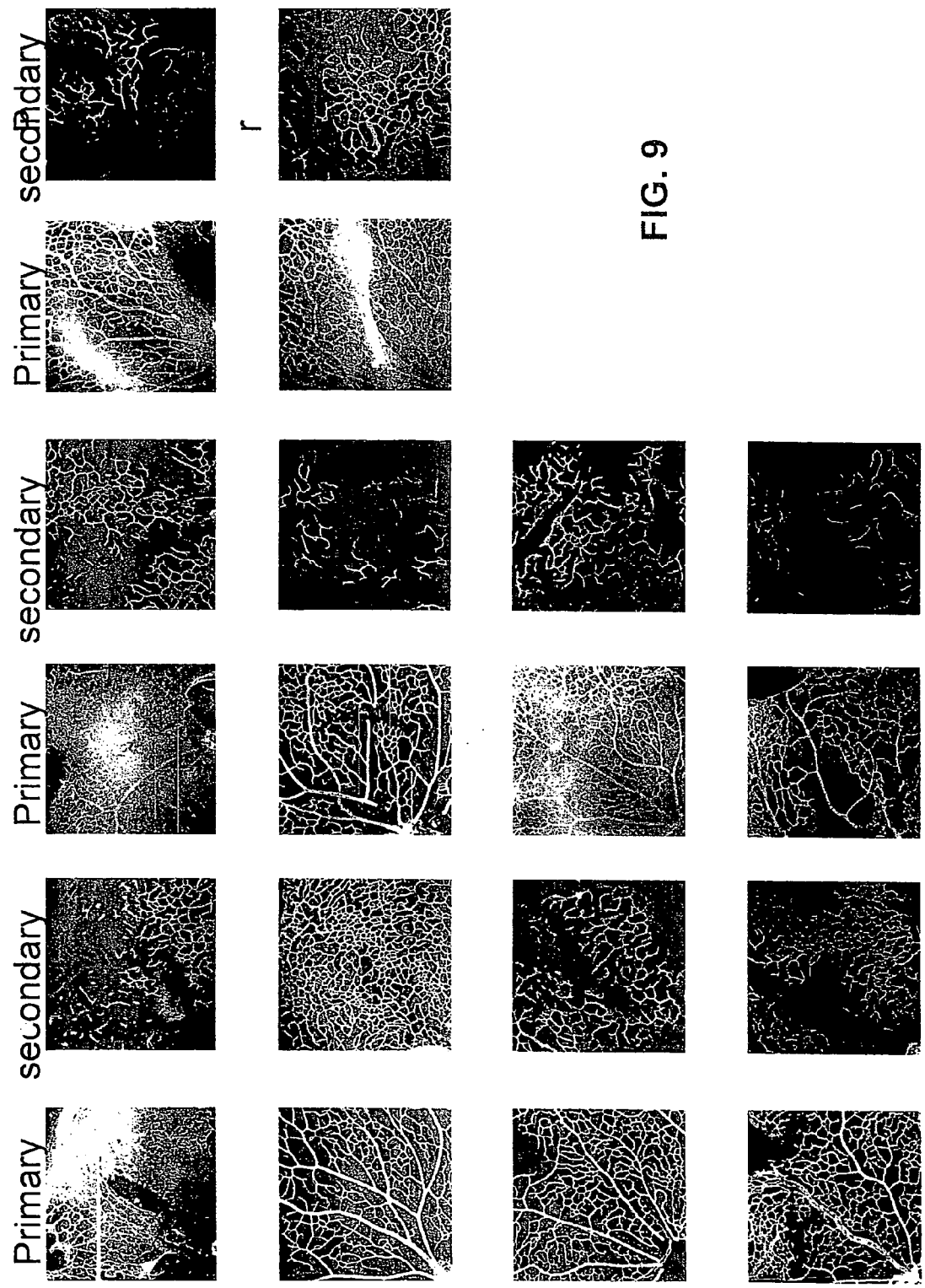
FIG. 9 depicts photomicrographs of primary and secondary vascular layers of retinas of mice from Example 2 intravitreally injected with a combination of 0.1× concentration of T2-TrpRS and 0.1× concentration of VEGF aptamer Compound (2).
Figure 10:
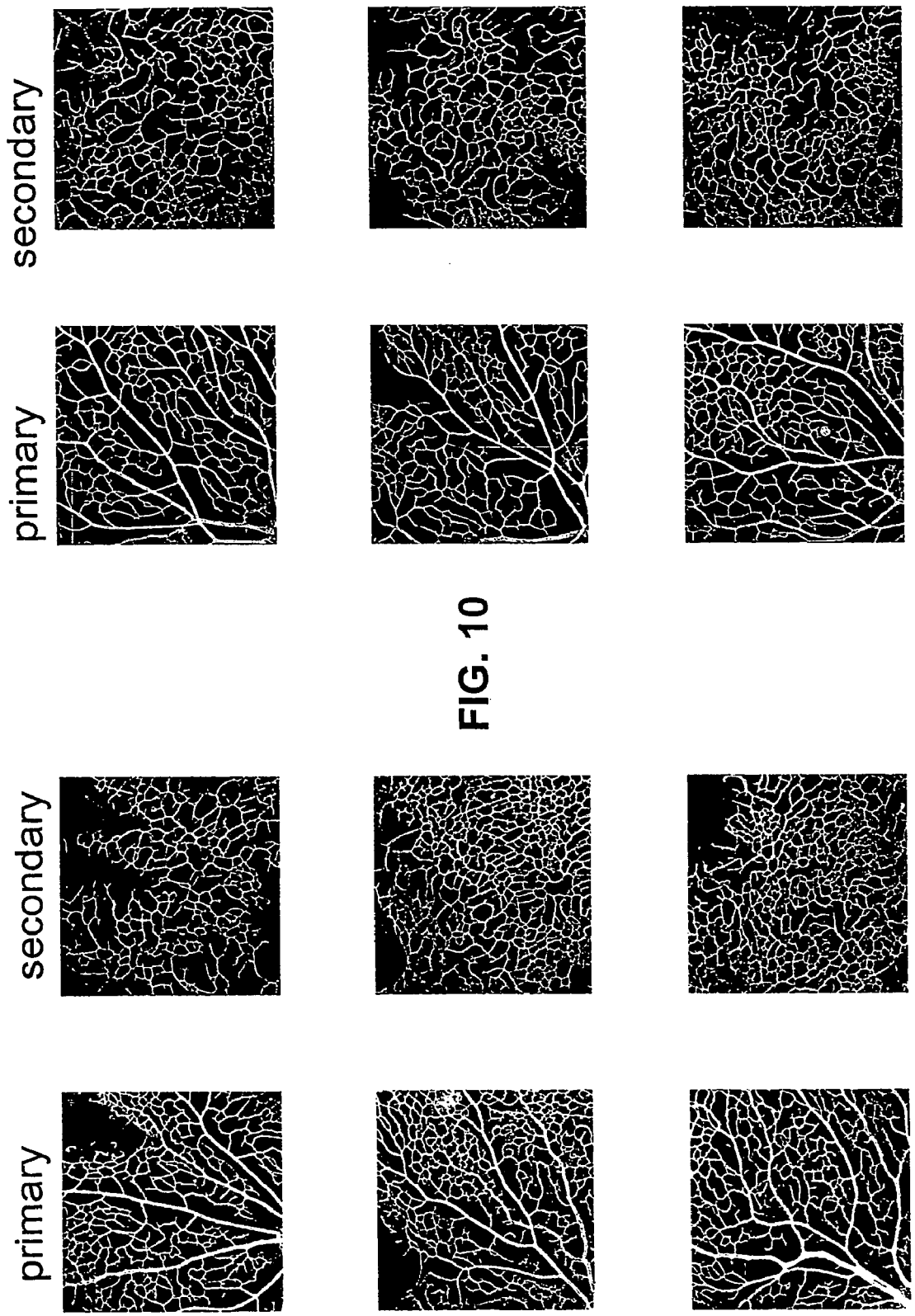
FIG. 10 depicts photomicrographs of primary and secondary vascular layers of retinas of control mice from Example 3 intravitreally injected with PBS.
Figure 12:
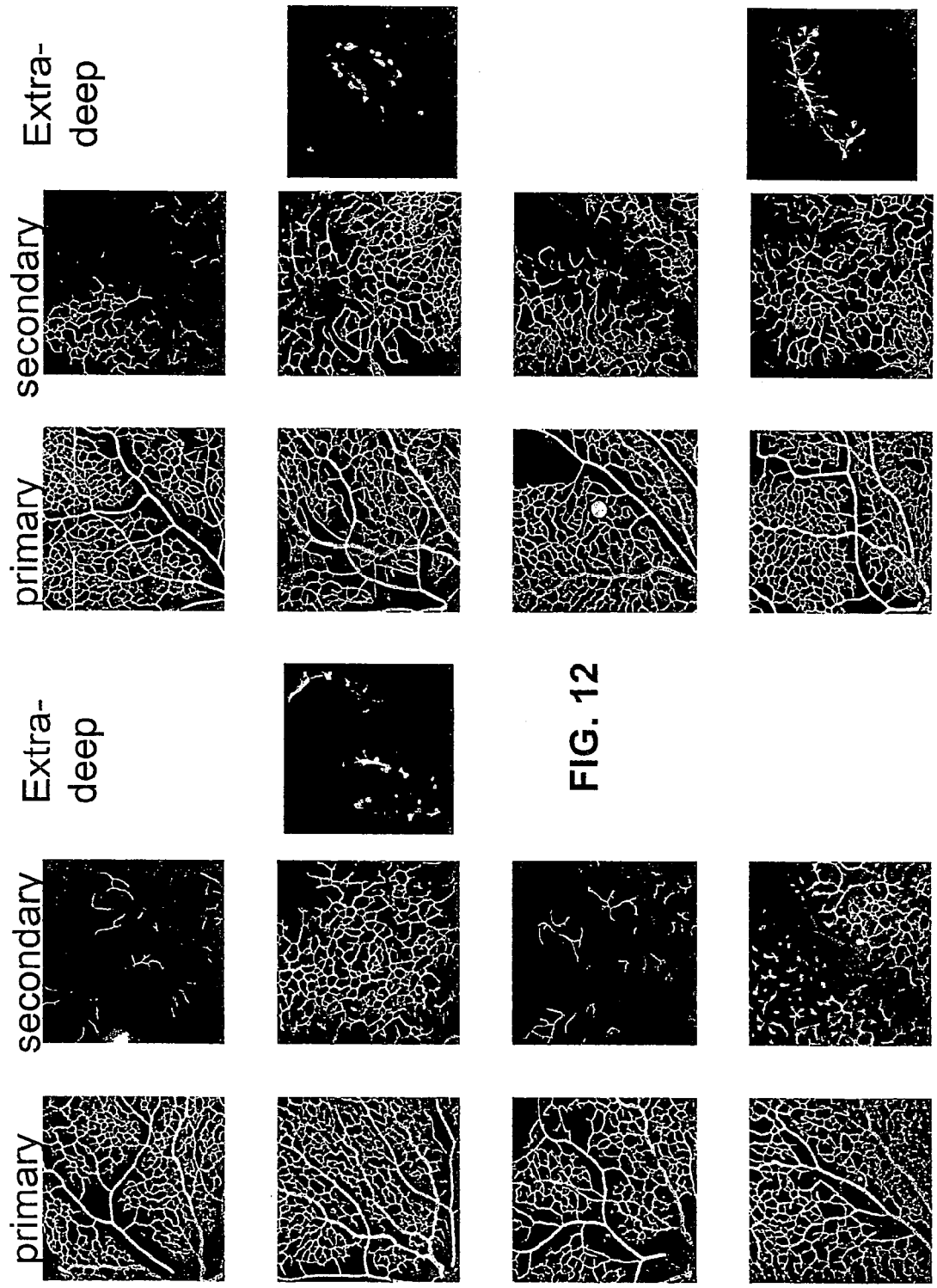
FIG. 12 depicts photomicrographs of primary and secondary vascular layers of retinas of mice from Example 3 intravitreally injected with a 1× concentration of VEGF aptamer Compound (2).
Figure 13:
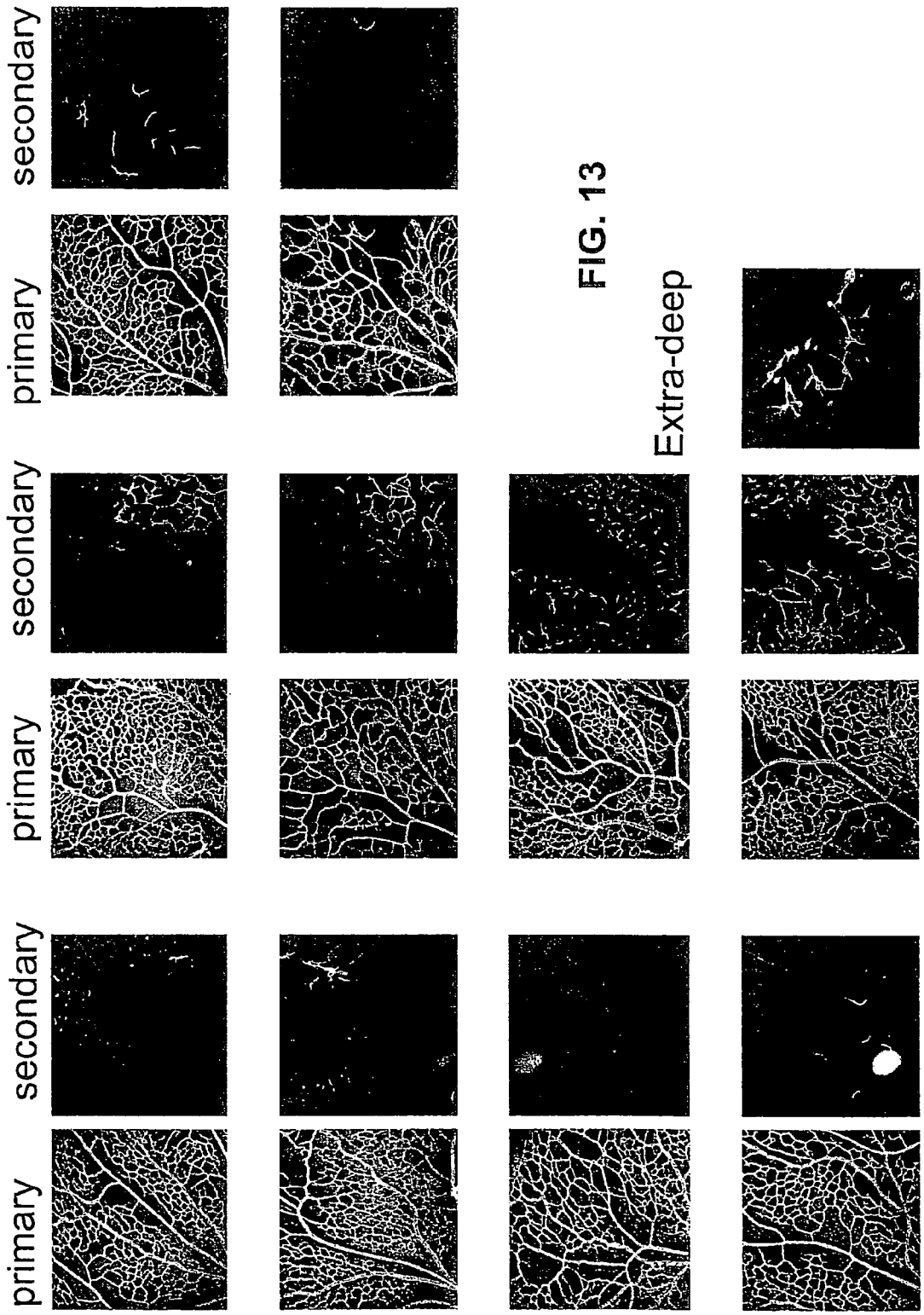
FIG. 13 depicts photomicrographs of primary and secondary vascular layers of retinas of mice from Example 3 intravitreally injected with a 1× concentration of T2-TrpRS and a 1× concentration of VEGF aptamer Compound (2).
Figure 14:
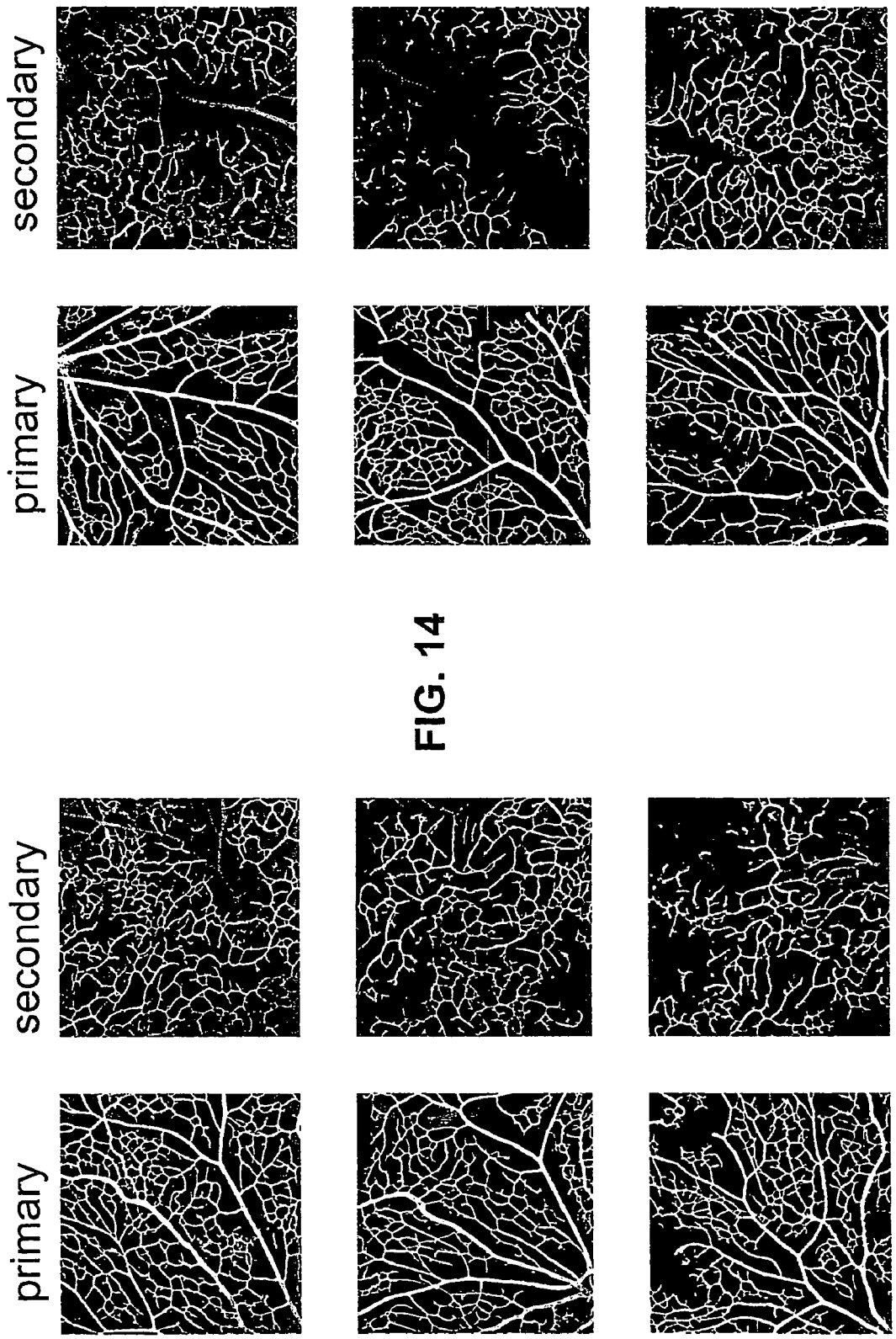
FIG. 14 depicts photomicrographs of primary and secondary vascular layers of retinas of control mice from Example 4 intravitreally injected with phosphate buffered saline (PBS).
Figure 16:
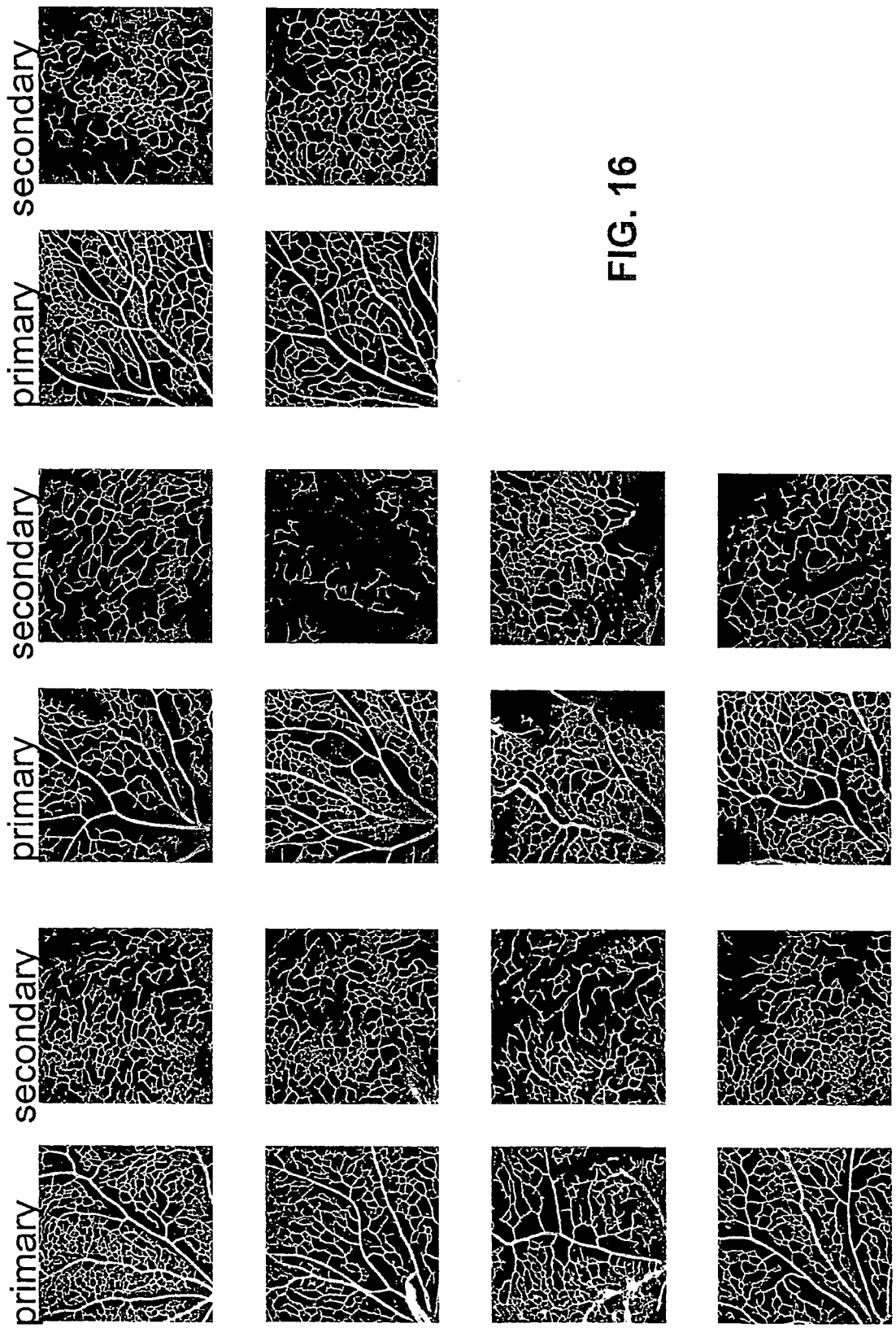
FIG. 16 depicts photomicrographs of primary and secondary vascular layers of retinas of mice from Example 4 intravitreally injected with a 0.5× concentration of VEGF aptamer Compound (2).
Figure 17:
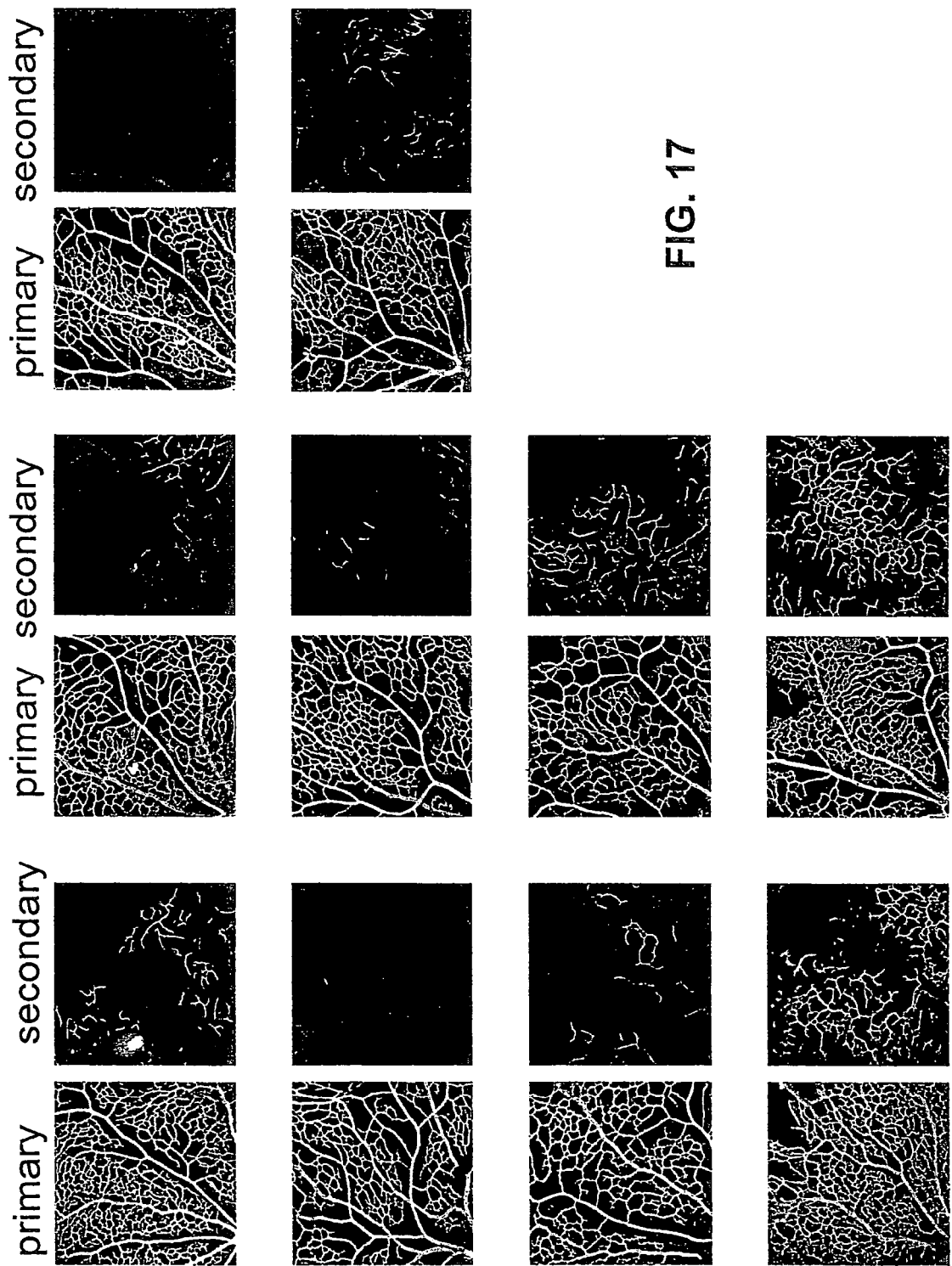
FIG. 17 depicts photomicrographs of primary and secondary vascular layers of retinas of mice from Example 4 intravitreally injected with a combination of a 1× concentration of T2-TrpRS and 0.5× concentration of VEGF aptamer Compound (2).
Figure 18:
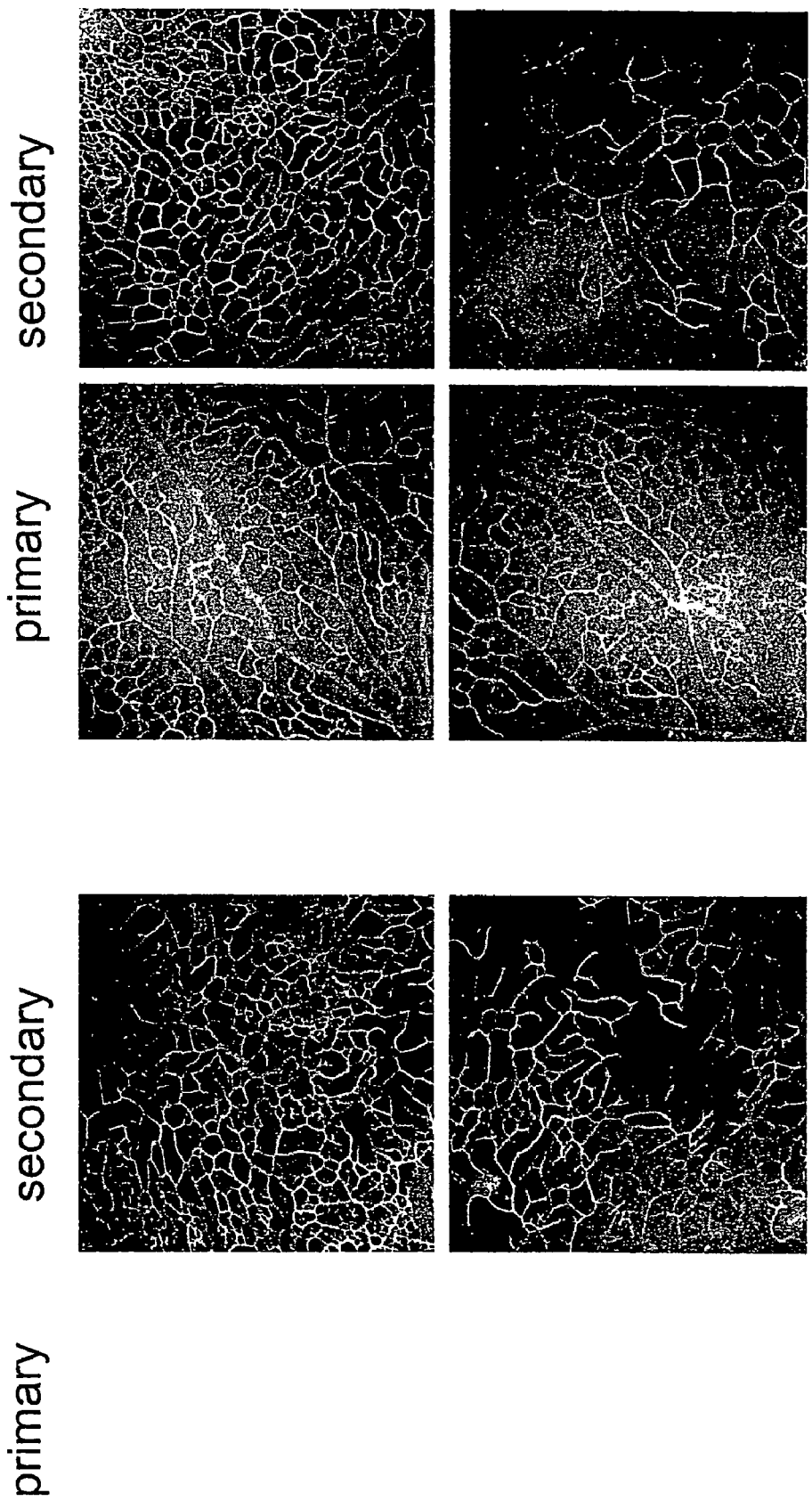
FIG. 18 depicts photomicrographs of primary and secondary vascular layers of retinas of control mice from Example 5 intravitreally injected with PBS.
Figure 19:
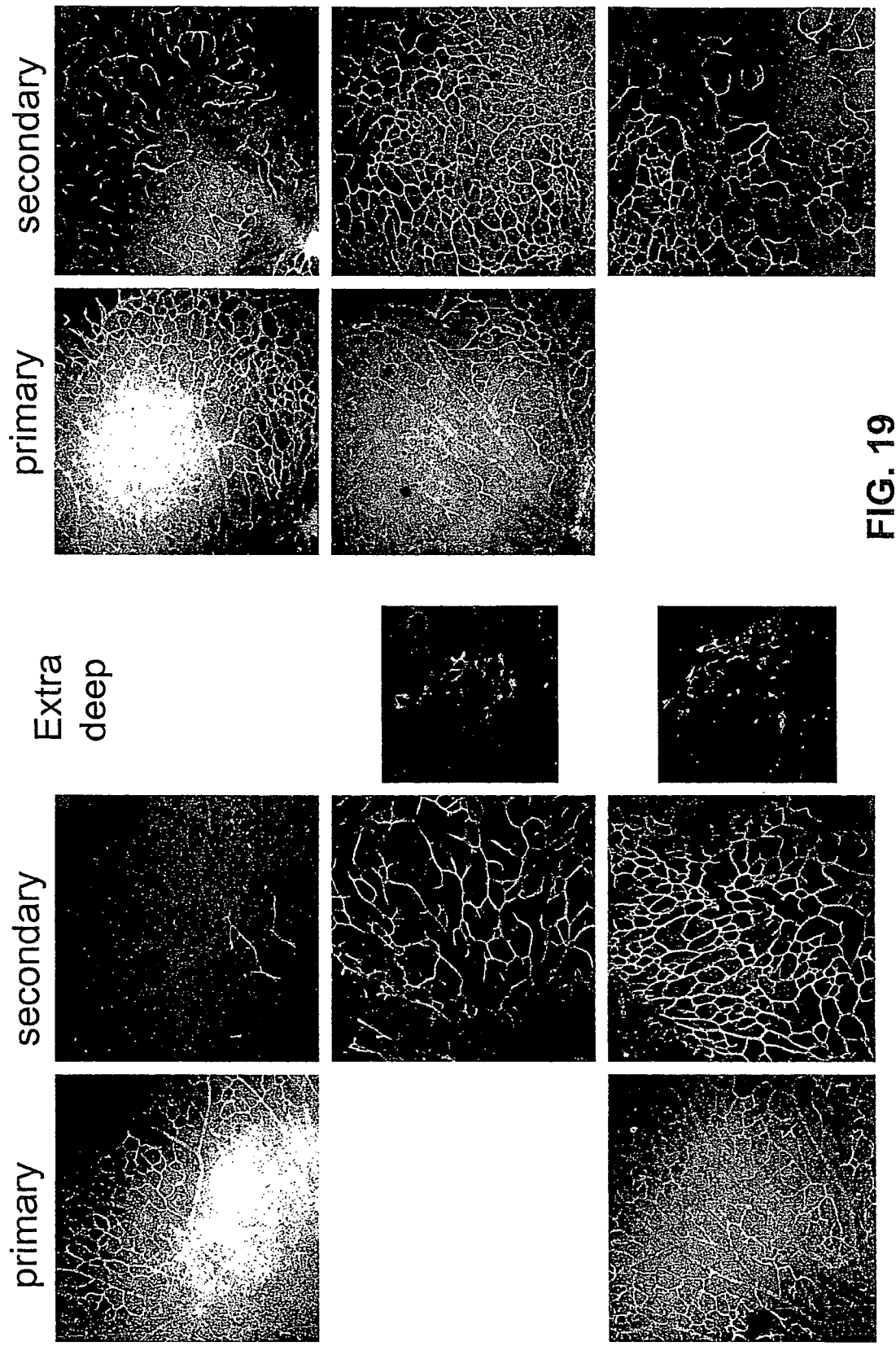
FIG. 19 depicts photomicrographs of primary and secondary vascular layers of retinas of mice from Example 5 intravitreally injected with a 1× concentration of T2-TrpRS.
Figure 20:
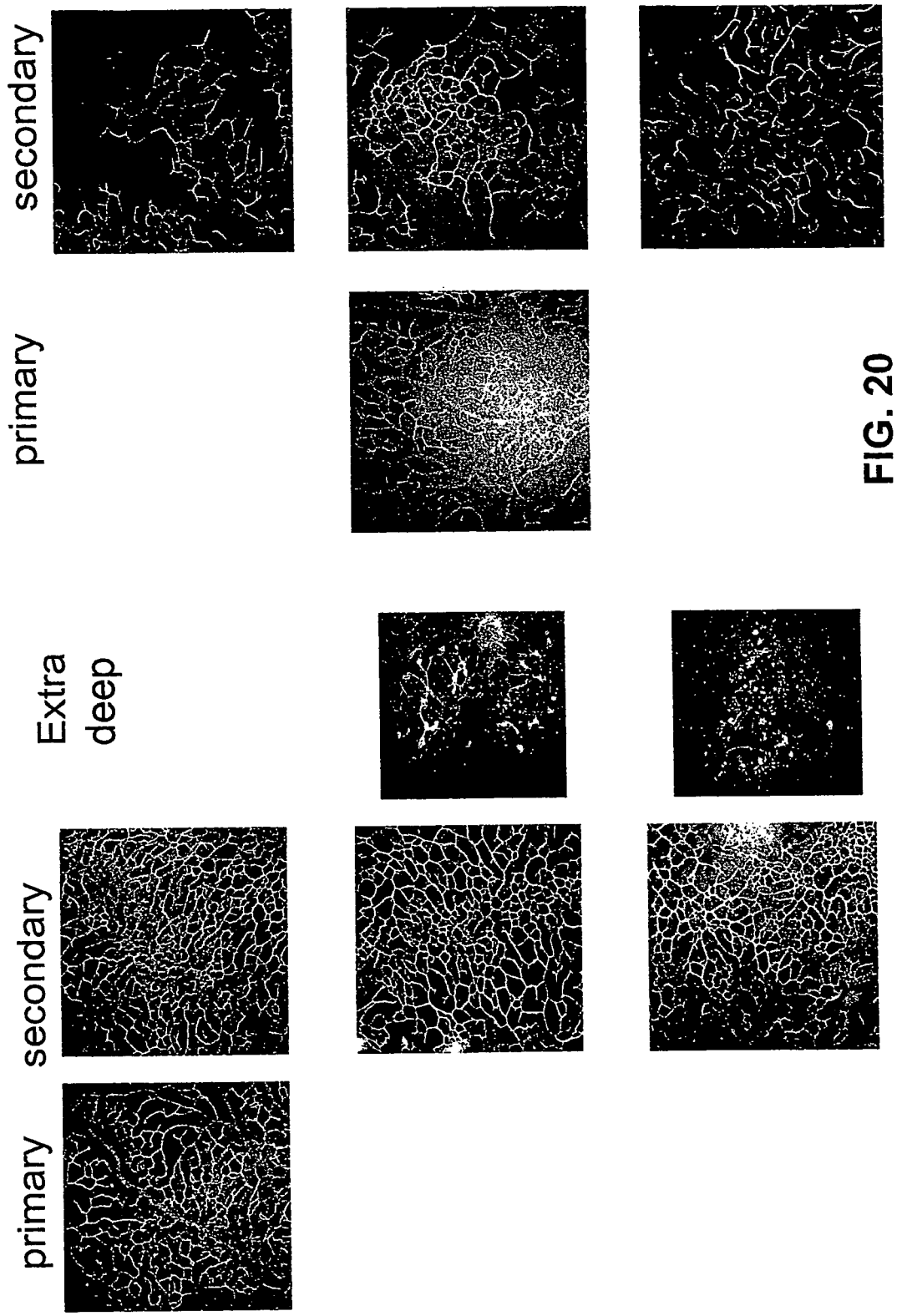
FIG. 20 depicts photomicrographs of primary and secondary vascular layers of retinas of mice from Example 5 intravitreally injected with a 0.5× concentration of peptidomimetic integrin signaling inhibitor Compound (1).
Figure 21:
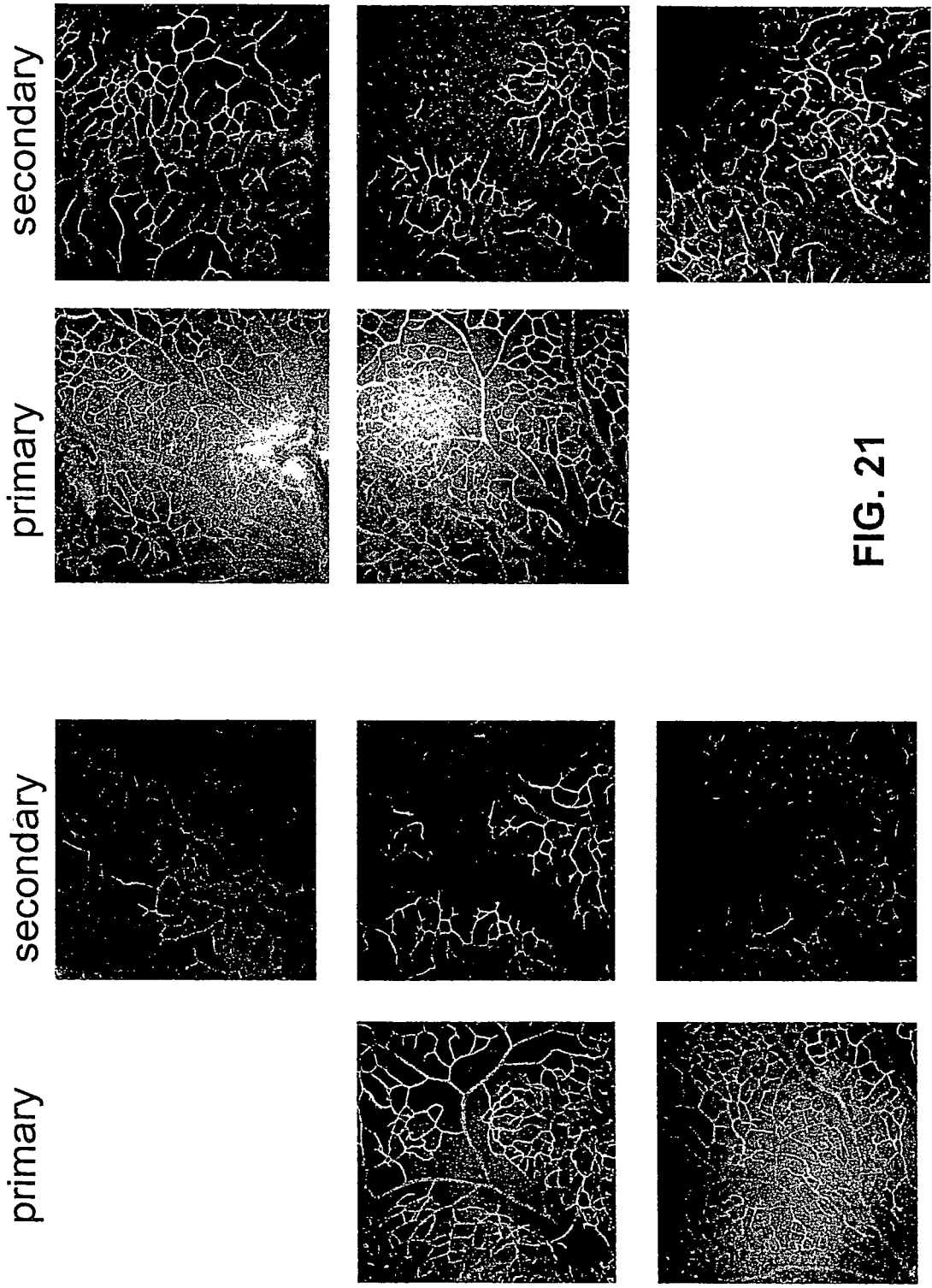
FIG. 21 depicts photomicrographs of primary and secondary vascular layers of retinas of mice from Example 5 intravitreally injected with a combination of a 1× concentration of T2-TrpRS and a 0.5× concentration of peptidomimetic integrin signaling inhibitor Compound (1).
Figure 29:
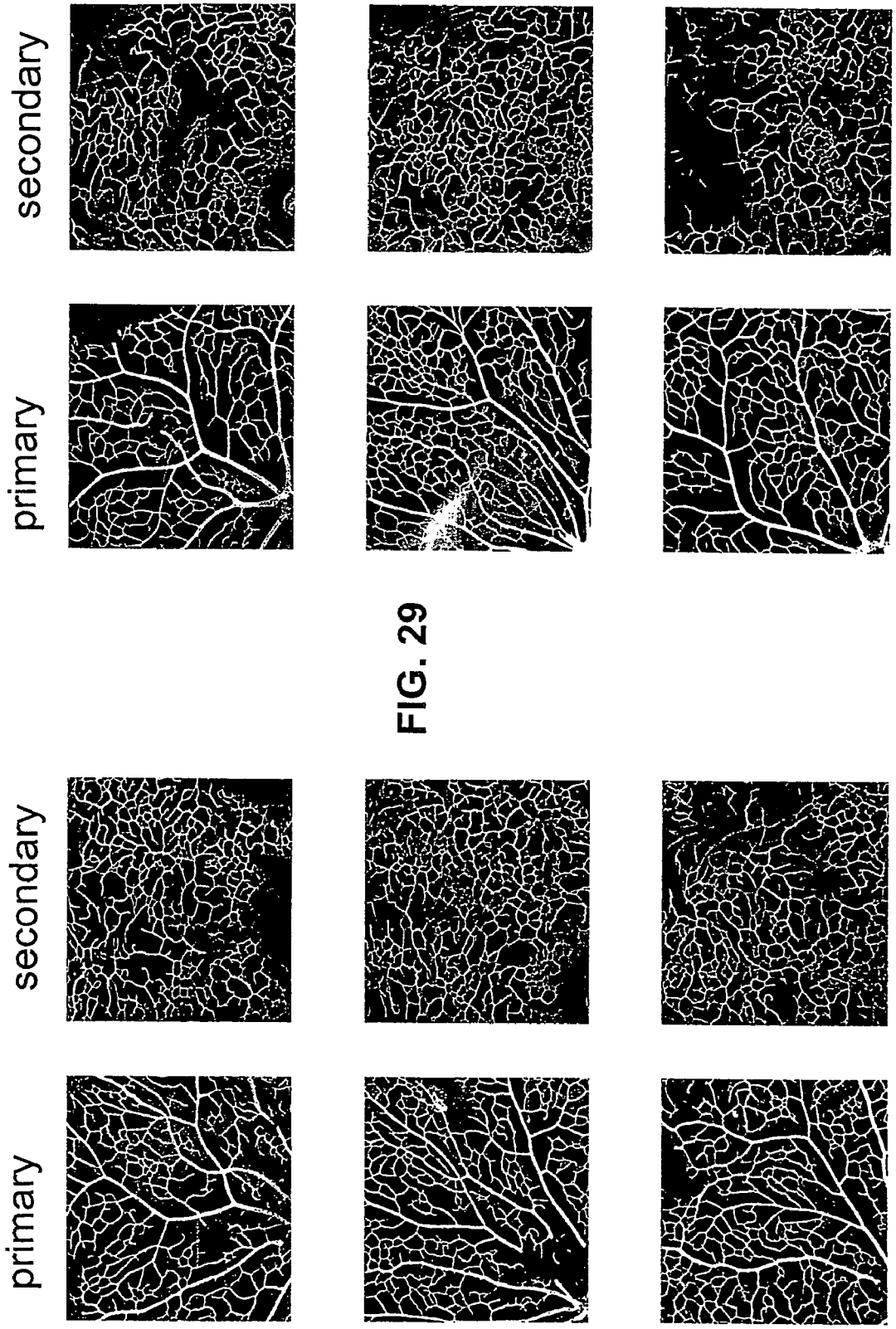
FIG. 29 depicts photomicrographs of primary and secondary vascular layers of retinas of control mice from Example 7 intravitreally injected with PBS.
Figure 30:
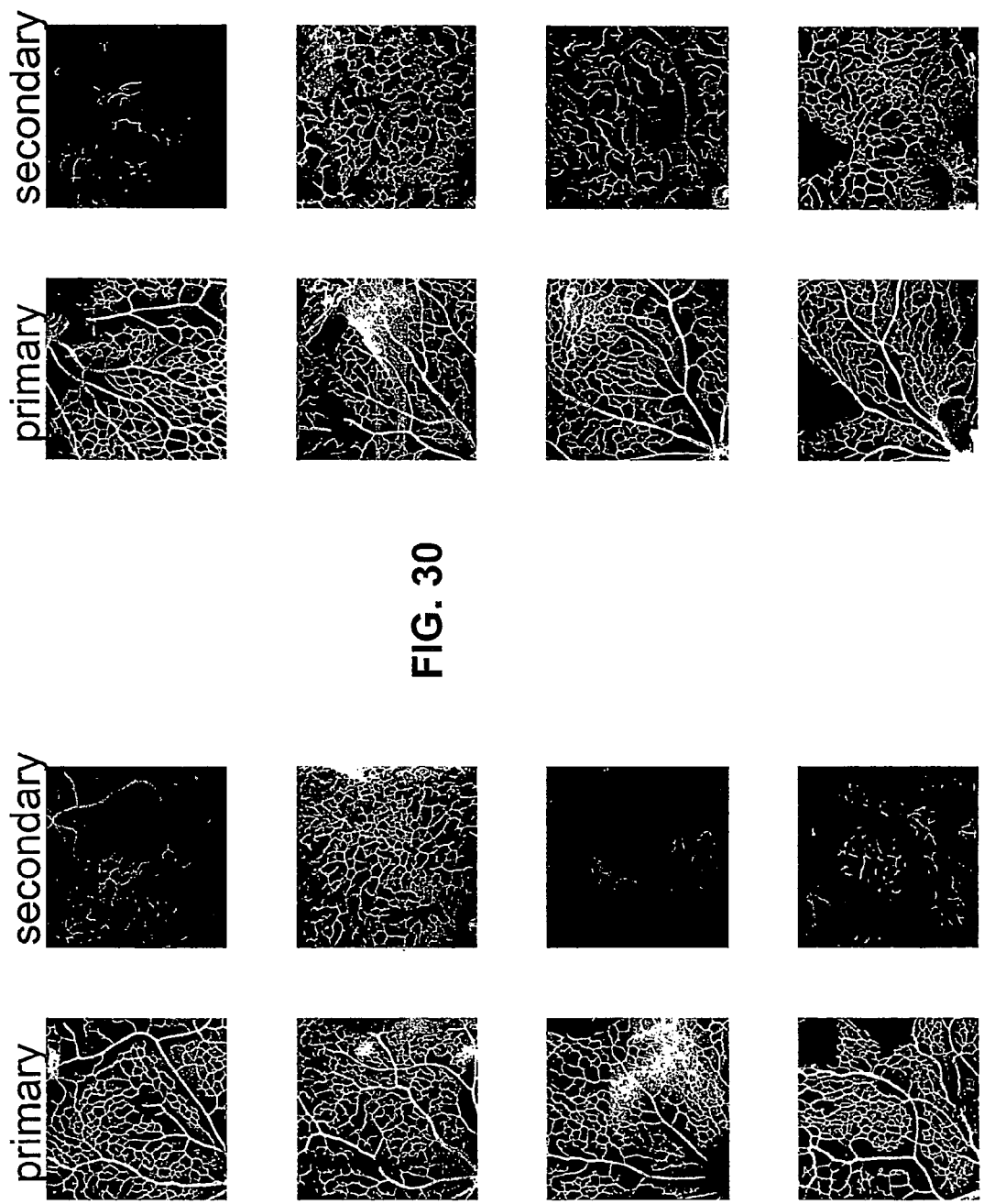
FIG. 30 depicts photomicrographs of primary and secondary vascular layers of retinas of mice from Example 7 intravitreally injected with a 1× concentration of T2-TrpRS.
Figure 33:
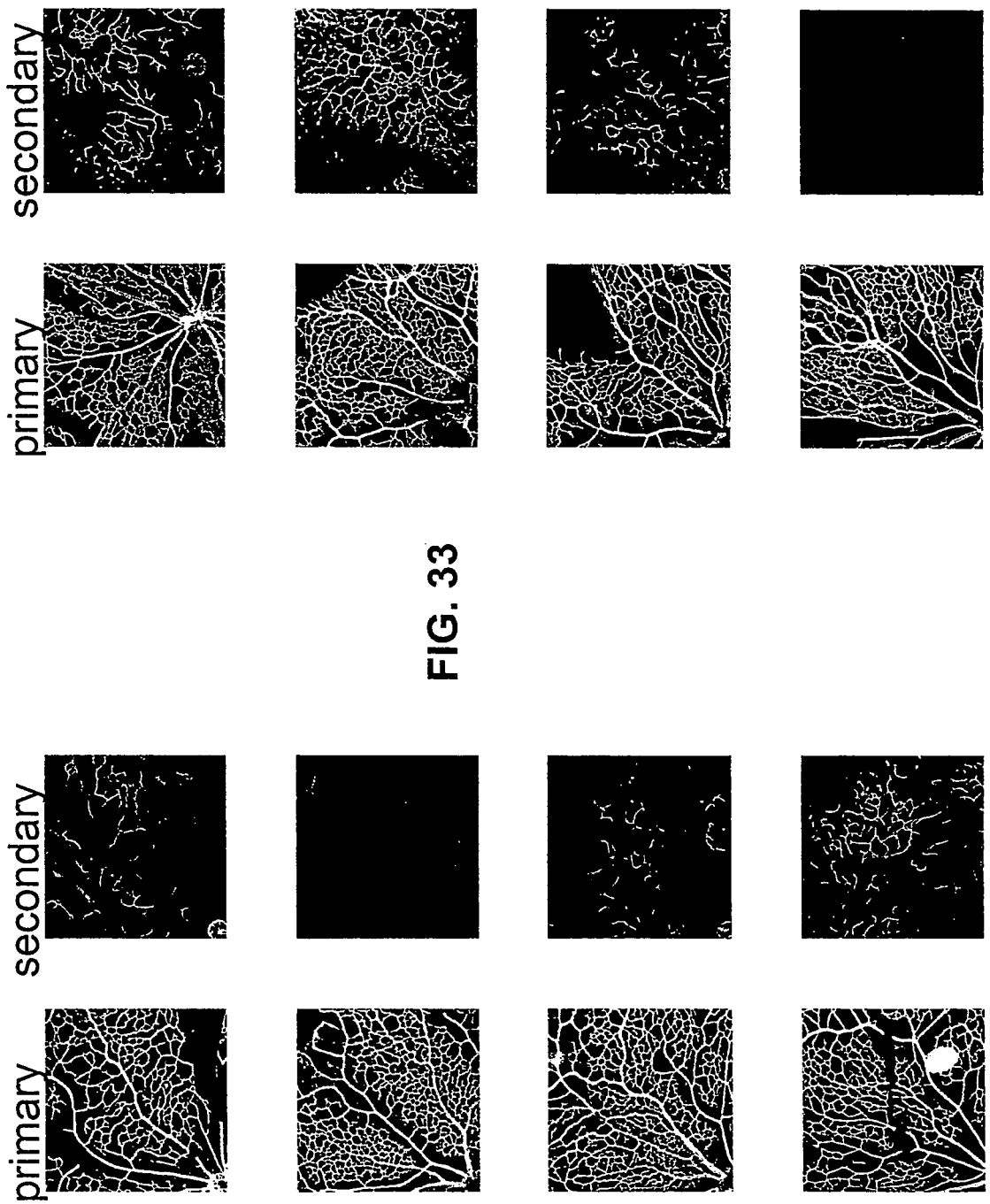
FIG. 33 depicts photomicrographs of primary and secondary vascular layers of retinas of mice from Example 7 intravitreally injected with a combination of a 0.5× concentration of peptidomimetic integrin signaling inhibitor Compound (1) and a 1× concentration of VEGF aptamer Compound (2).
Figure 36:
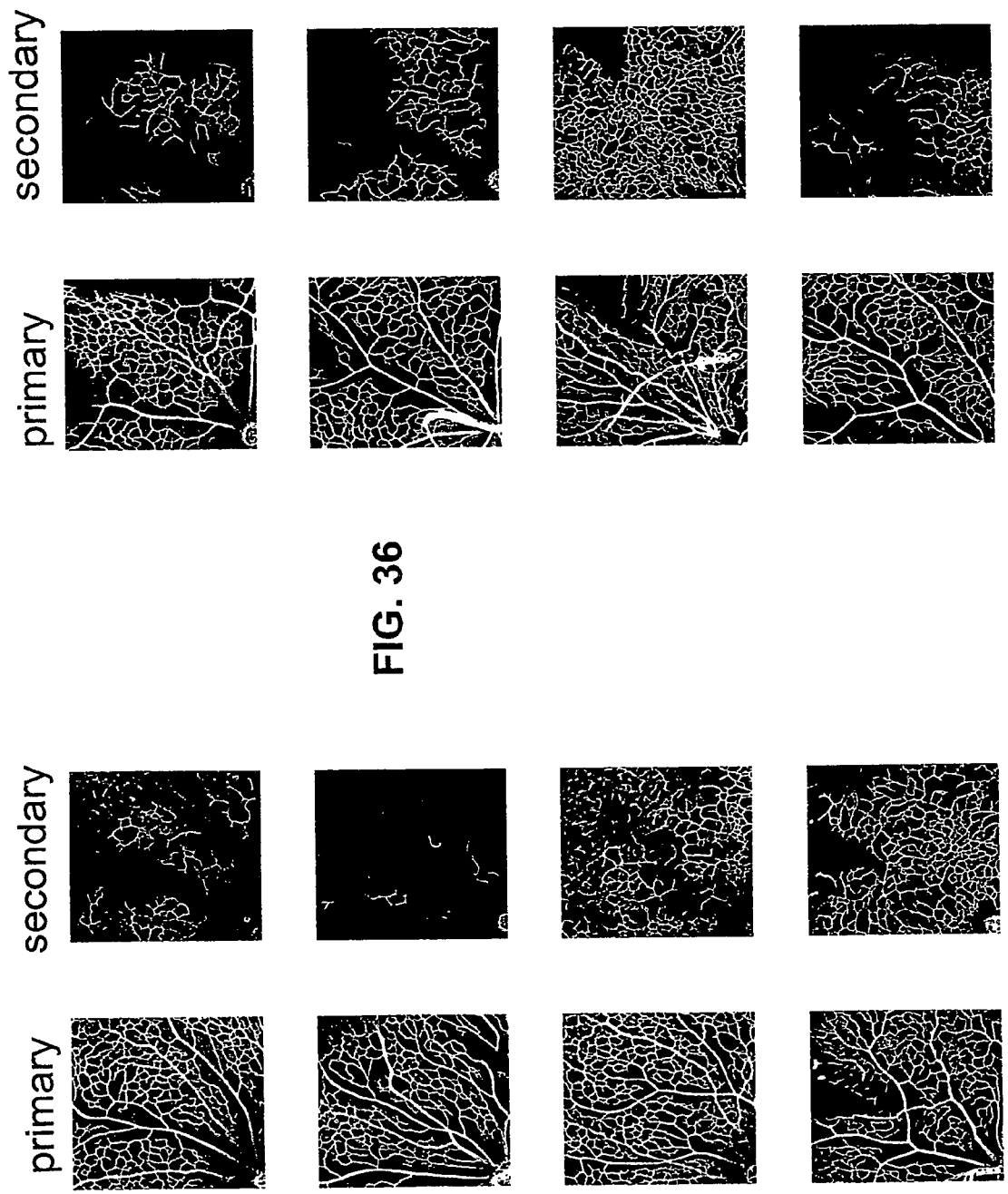
FIG. 36 depicts photomicrographs of primary and secondary vascular layers of retinas of mice from Example 9 intravitreally injected with a 1× concentration of peptidomimetic integrin signaling inhibitor Compound (1).
Figure 37:
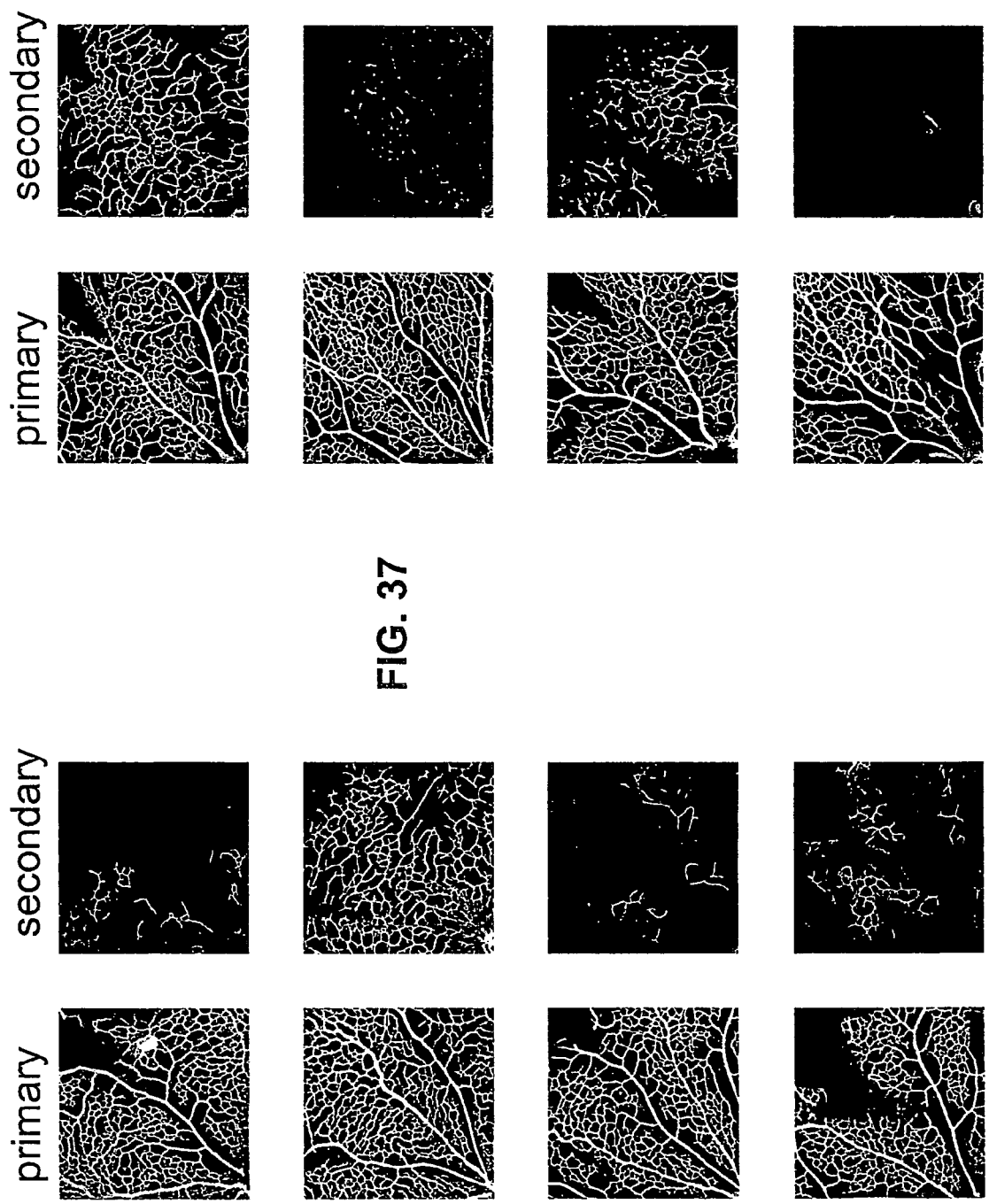
FIG. 37 depicts photomicrographs of primary and secondary vascular layers of retinas of mice from Example 9 intravitreally injected with a 1× concentration of VEGF aptamer Compound (2).
Figure 38:
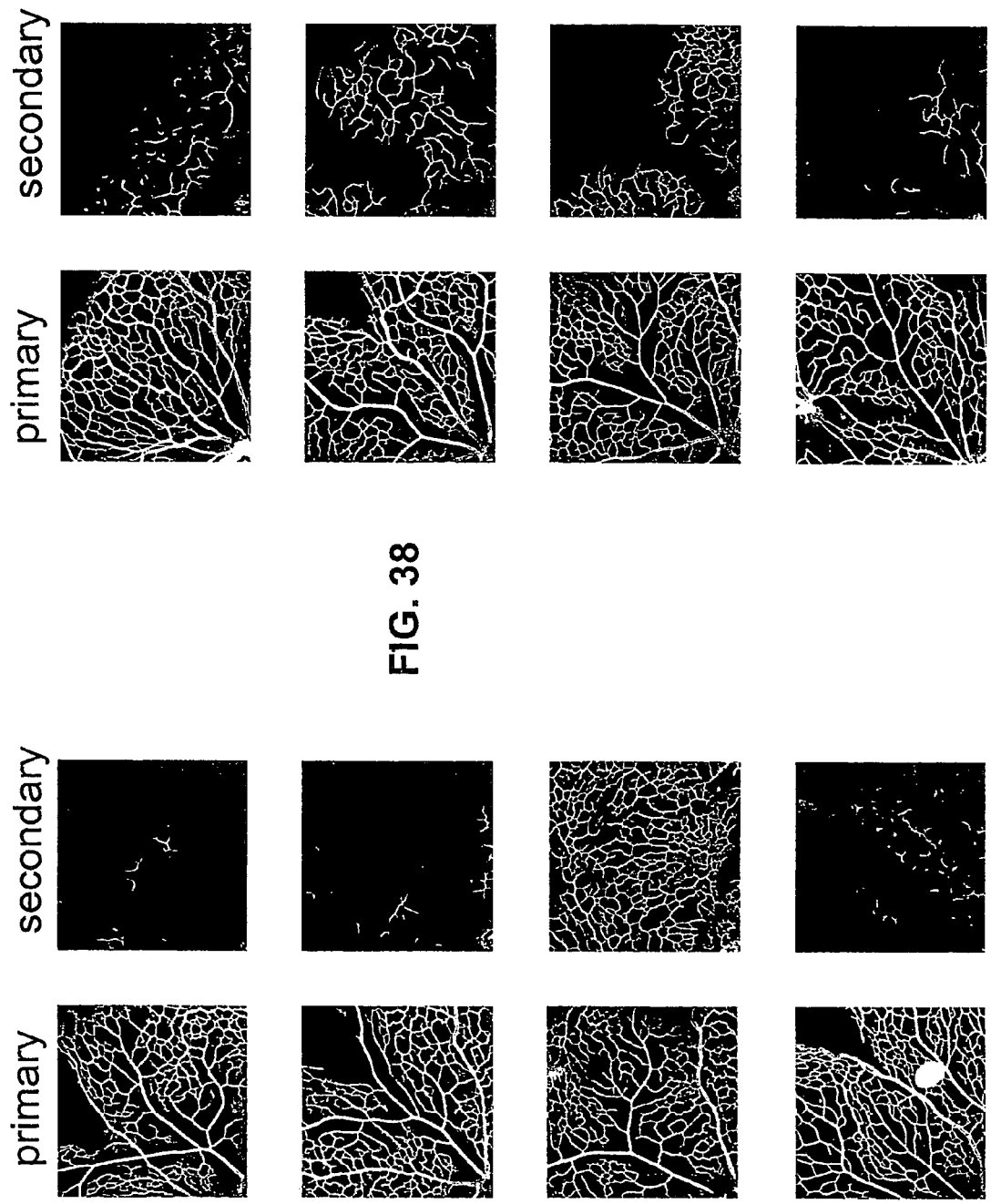
FIG. 38 depicts photomicrographs of primary and secondary vascular layers of retinas of mice from Example 9 intravitreally injected with a 1× concentration of T2-TrpRS.
Figure 39:
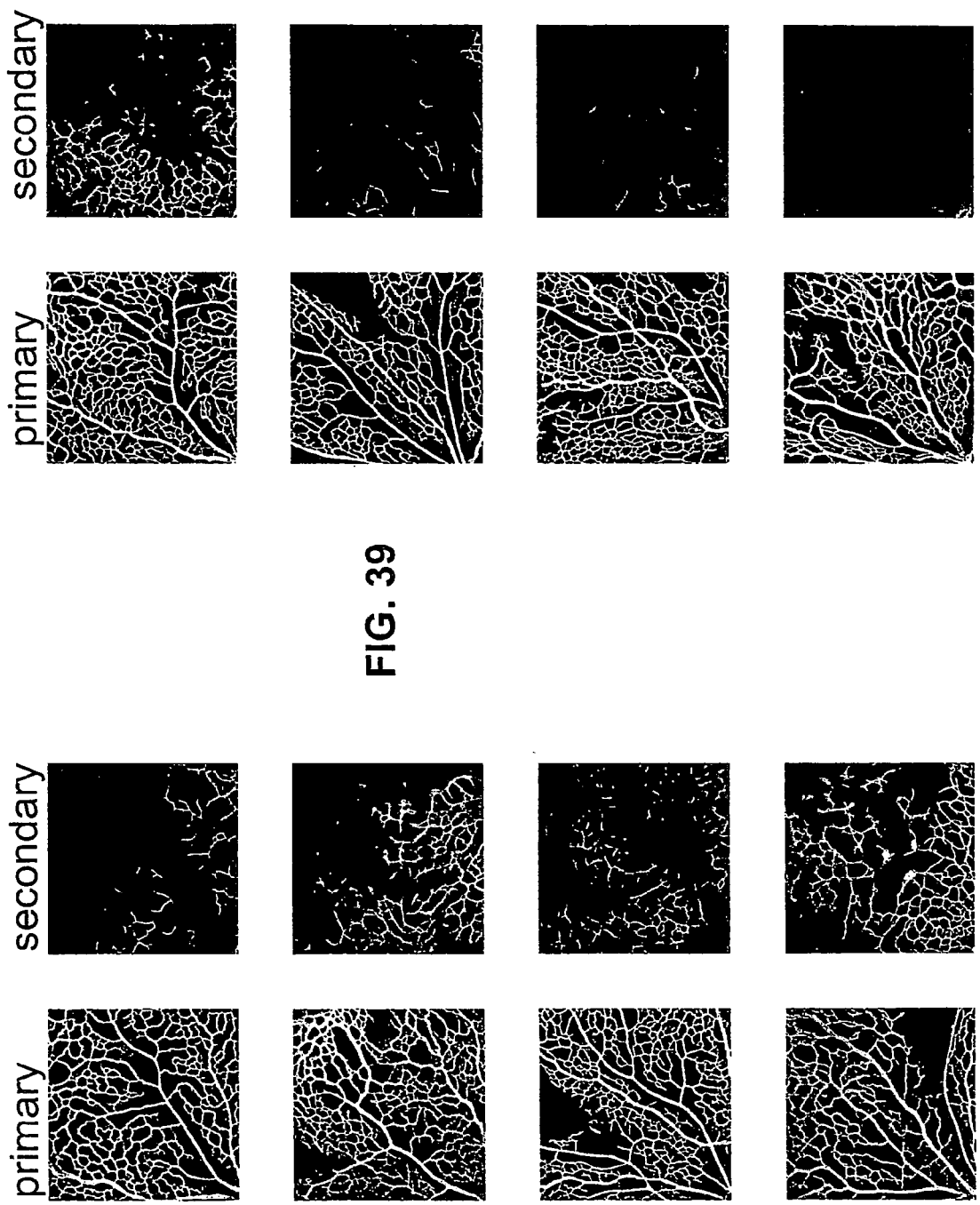
FIG. 39 depicts photomicrographs of primary and secondary vascular layers of retinas of mice from Example 9 intravitreally injected with a 1× concentration of each of T2-TrpRS and peptidomimetic integrin signaling inhibitor Compound (1).
Figure 40:
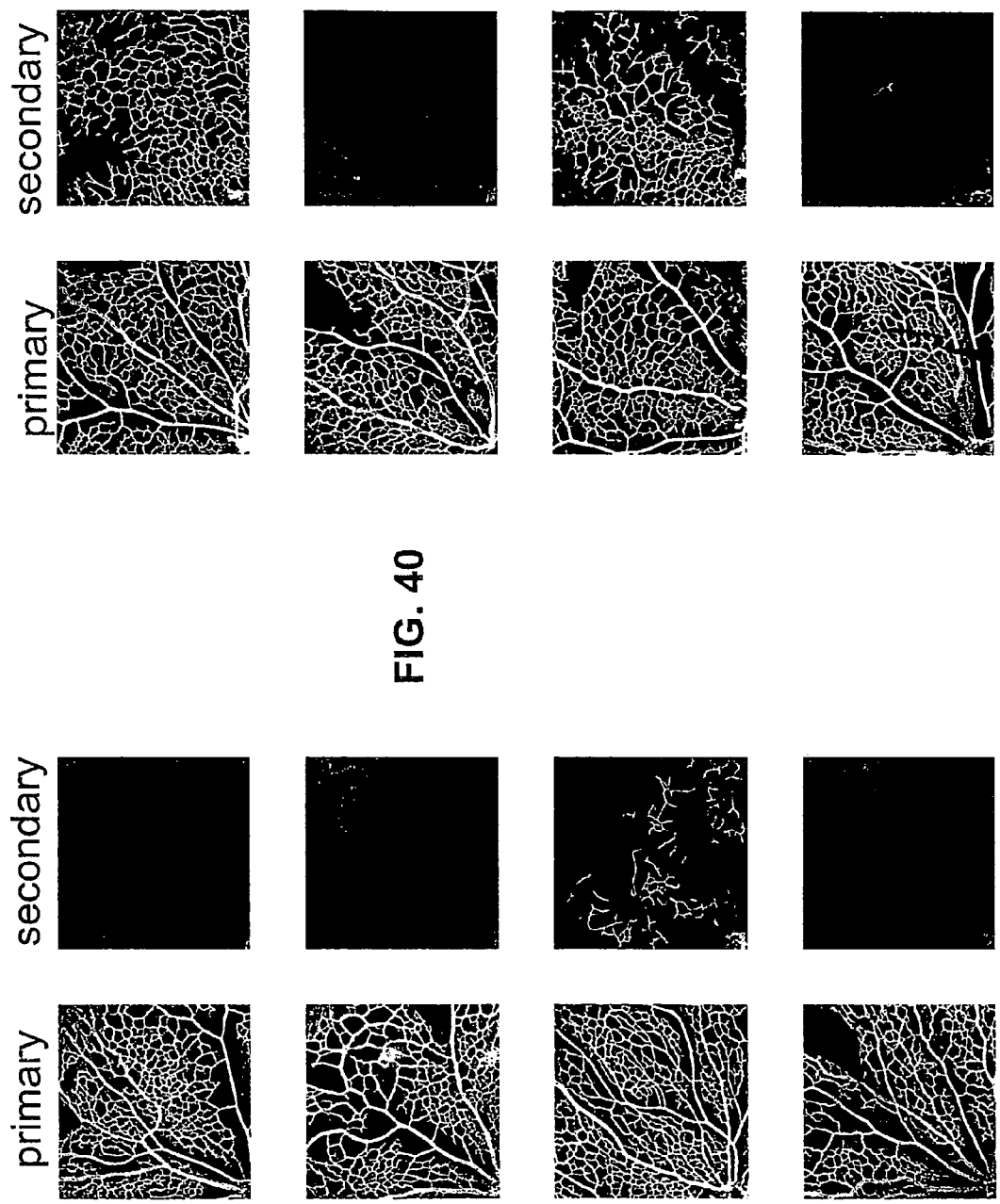
FIG. 40 depicts photomicrographs of primary and secondary vascular layers of retinas of mice from Example 9 intravitreally injected with a 1× concentration of each of peptidomimetic integrin signaling inhibitor Compound (1) and VEGF aptamer Compound (2).
Figure 41:
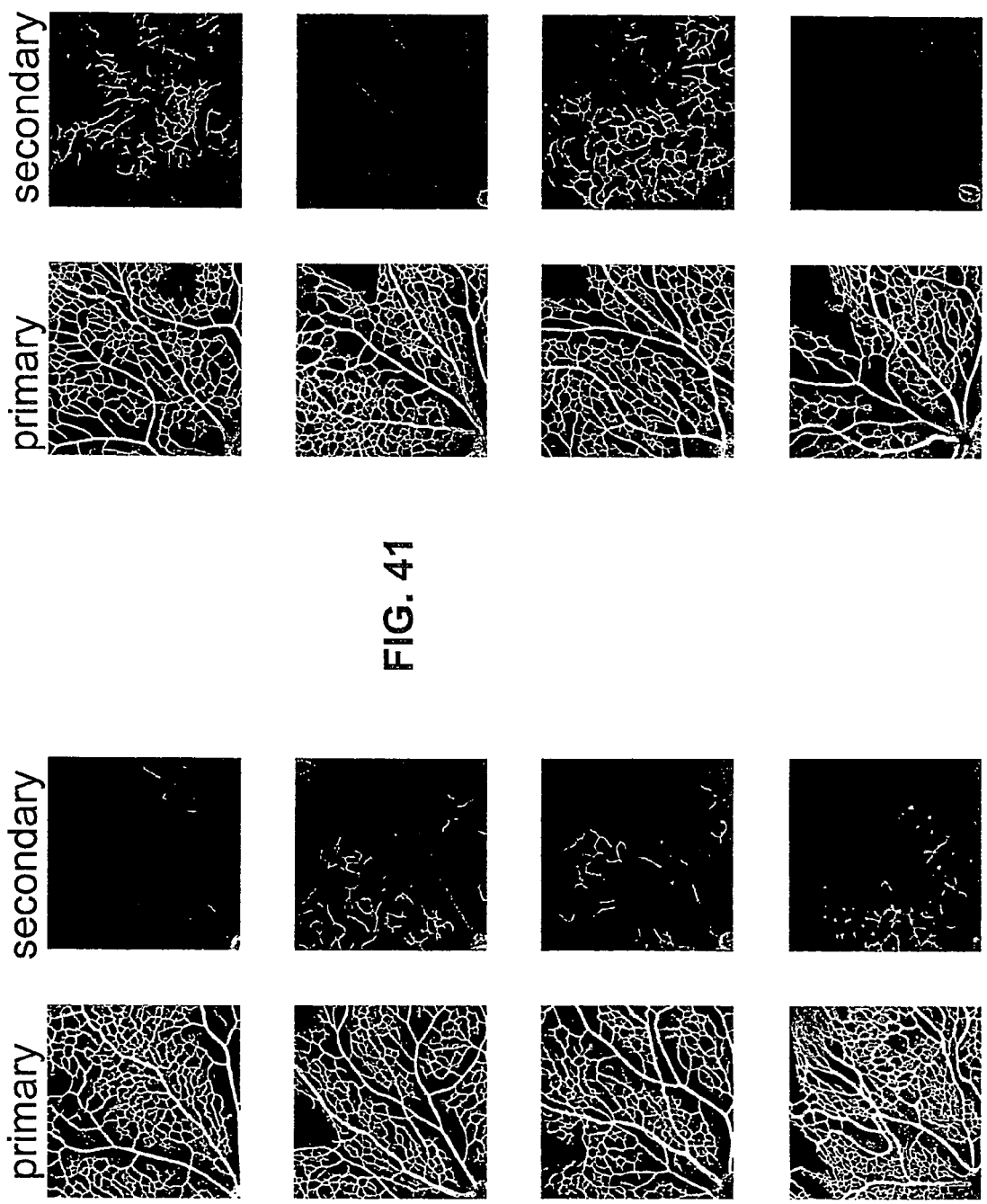
FIG. 41 depicts photomicrographs of primary and secondary vascular layers of retinas of mice from Example 9 intravitreally injected with a combination of a 1× concentration of each of T2-TrpRS and VEGF aptamer Compound (2).
Figure 42:
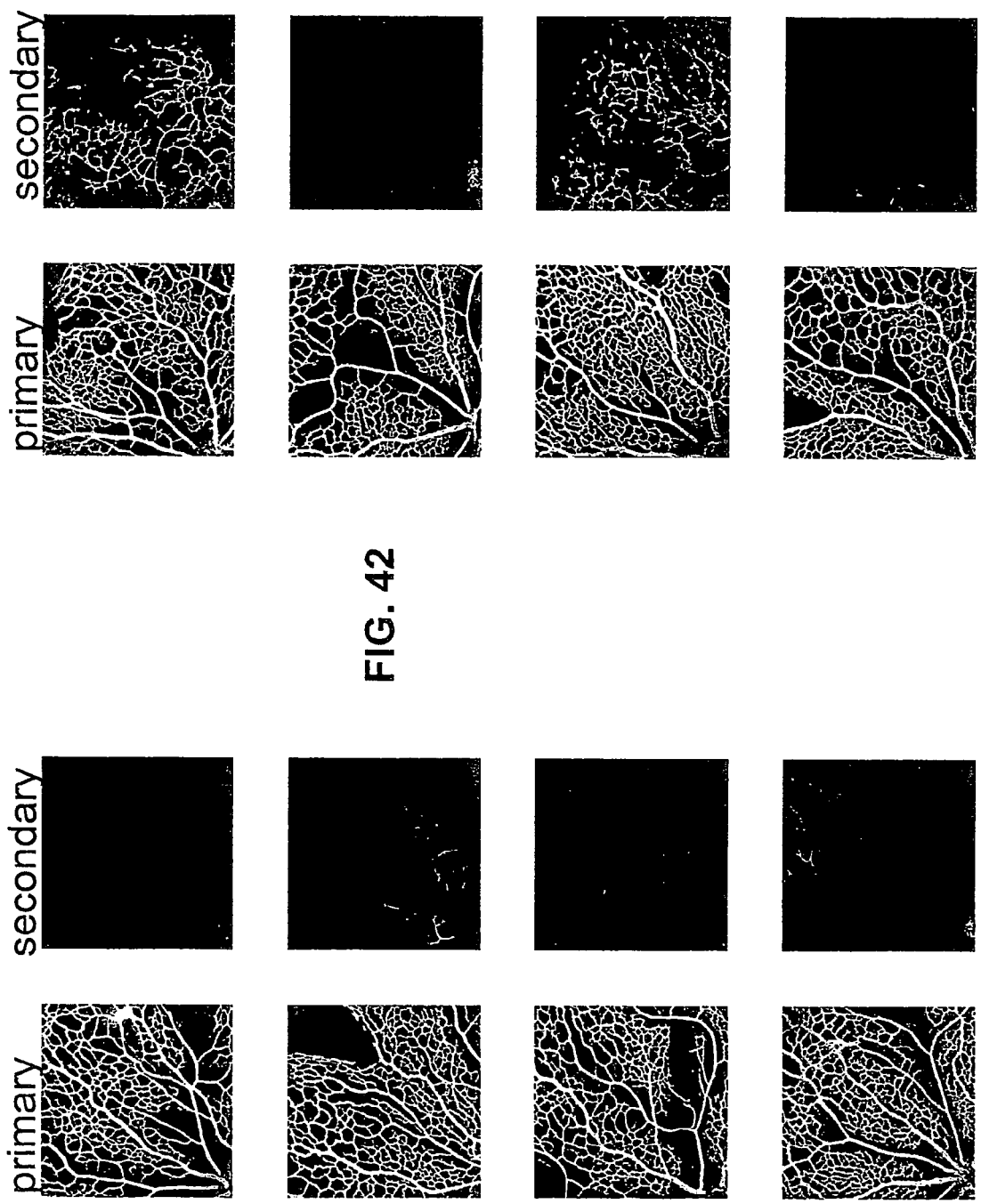
FIG. 42 depicts photomicrographs of primary and secondary vascular layers of retinas of mice from Example 9 intravitreally injected with a combination of a 1× concentration of each of the inhibitors T2-TrpRS, peptidomimetic integrin signaling inhibitor Compound (1), and VEGF aptamer Compound (2).

Treatment of Neonatal Mouse Eyes with a Combination of a Peptidomimetic Integrin Signaling Inhibitor and a VEGF Signaling Inhibitor Following the General Angiogenesis Assay Procedure ("General Procedure") described hereinabove, the eyes of neonatal Balb/C mice were intravitreally injected on postnatal day 8 (P8) with either a 0.25× concentration of integrin signaling inhibitor Compound (1) (five mice), a 0.5× concentration of VEGF aptamer Compound (2) (five mice), or a combination of a 0.25× concentration Compound (1) and a 0.5× concentration of Compound (2) (six mice). As a control, another group of six mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 1 and in FIGS. 4 and 5.

TABLE 1

|  | % inhibition: | | | | |
| --- | --- | --- | --- | --- | --- |
|  | 0-10% | 10-25% | 25-50% | 50-75% | 75-100% |
| PBS | 100 | 0 | 0 | 0 | 0 |
| 0.5× Compound (2) | 20 | 20 | 20 | 20 | 40 |
| 0.1× Compound (1) | 40 | 0.5 | 20 | 20 | 20 |
| Combination | 0 | 17 | 0 | 0 | 83 |

EXAMPLE 2

Treatment of Neonatal Mouse Eyes with a Combination of an Angiostatic Fragment of TrpRS and a VEGF Signaling Inhibitor Following the General Procedure, the eyes of neonatal Balb/C mice were intravitreally injected on P4 with either a 0.1× concentration of T2-TrpRS (eight mice), a 0.1× concentration of VEGF aptamer Compound (2) (eight mice), or a combination of a 0.1× concentration T2-TrpRS and a 0.1× concentration of Compound (2) (ten mice). As a control, another group of eight mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 2 and in FIGS. 6, 7, 8, and 9.

TABLE 2

|  | % inhibition: | | | | | | |
| --- | --- | --- | --- | --- | --- | --- | --- |
|  | 0-10% | 10-25% | 25-50% | 50-75% | 75-100% | >95% | 100% |
| PBS | 100.0 | 0 | 0 | 0 | 0 | 0 | 0 |
| 0.1× Comp. (2) | 87.5 | 12.5 | 0 | 0 | 0 | 0 | 0 |
| 0.1× T2-TrpRS | 50 | 37.5 | 12.5 | 0 | 0 | 0 | 0 |
| Combination | 10 | 30 | 20 | 20 | 20 | 0 | 0 |

EXAMPLE 3

Treatment of Neonatal Mouse Eyes with a Combination of an Angiostatic Fragment of TrpRS and a VEGF Signaling Inhibitor Following the General Procedure, the eyes of neonatal Balb/C mice were intravitreally injected on P4 with either a 1× concentration of T2-TrpRS (eight mice), a 1× concentration of VEGF aptamer Compound (2) (eight mice), or a combination of a 1× concentration T2-TrpRS and a 1× concentration of Compound (2) (ten mice). As a control, another group of six mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 3 and in FIGS. 10, 11, 12, and 13.

TABLE 3

|  | % inhibition: | | | | | | |
| --- | --- | --- | --- | --- | --- | --- | --- |
|  | 0-10% | 10-25% | 25-50% | 50-75% | 75-100% | >95% | 100% |
| PBS | 100 | 0 | 0 | 0 | 0 | 0 | 0 |
| 1× Comp. (2) | 37.5 | 12.5 | 12.5 | 12.5 | 25 | 0 | 0 |
| 1× T2-TrpRS | 12.5 | 12.5 | 0 | 12.5 | 62.5 | 12.5 | 12.5 |
| Combination | 0 | 0 | 10 | 10 | 80 | 40 | 20 |

EXAMPLE 4

Treatment of Neonatal Mouse Eyes with a Combination of an Angiostatic Fragment of TrpRS and a VEGF Signaling Inhibitor Following the General Procedure, the eyes of neonatal Balb/C mice were intravitreally injected on P4 with either a 1× concentration of T2-TrpRS (eight mice), a 0.5× concentration of VEGF aptamer Compound (2) (ten mice) or a combination of a 1× concentration T2-TrpRS and a 0.5× concentration of Compound (2) (ten mice). As a control, another group of six mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 4 and in FIGS. 14, 15, 16, and 17.

TABLE 4

| | % inhibition: | | | | | |
|---|---|---|---|---|---|---|
| | 0-10% | 10-25% | 25-50% | 50-75% | 75-100% | >95% | 100% |
| PBS | 66.6 | 16.7 | 16.7 | 0 | 0 | 0 | 0 |
| 0.5× Comp. (2) | 60 | 30 | 0 | 0 | 10 | 0 | 0 |
| 1× T2-TrpRS | 12.5 | 37.5 | 12.5 | 12.5 | 25 | 0 | 0 |
| Combination | 0 | 0 | 10 | 10 | 70 | 30 | 20 |

EXAMPLE 5

Treatment of Neonatal Mouse Eyes with a Combination of an Angiostatic Fragment of TrpRS and an Integrin Signaling Inhibitor Following the General Procedure, the eyes of neonatal Balb/C mice were intravitreally injected on P4 with either a 1× concentration of T2-TrpRS, a 0.5× concentration of integrin signaling inhibitor Compound (1) or a combination of a 1× concentration T2-TrpRS and a 0.5× concentration of Compound (1), in groups of six mice for each treatment regimen. As a control, another group of four mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 5 and in FIGS. 18, 19, 20, and 21.

TABLE 5

| | % inhibition: | | | | | |
|---|---|---|---|---|---|---|
| | 0-10% | 10-25% | 25-50% | 50-75% | 75-100% | >95% | 100% |
| PBS | 50 | 25 | 25 | 0 | 0 | 0 | 0 |
| 0.5× Comp. (1) | 50 | 33.3 | 16.7 | 0 | 0 | 0 | 0 |
| 1× T2-TrpRS | 33.3 | 16.7 | 33.3 | 0 | 16.7 | 16.7 | 0 |
| Combination | 0 | 33.3 | 16.7 | 0 | 50 | 16.7 | 0 |

EXAMPLE 6

Treatment of Neonatal Mouse Eyes with a Combination of an Angiostatic Fragment of TrpRS, a VEGF Signaling Inhibitor, and an Integrin Signaling Inhibitor Following the General Procedure, the eyes of neonatal Balb/C mice were intravitreally injected on P4 with either a 1× concentration of T2-TrpRS, a 0.5× concentration of integrin signaling inhibitor Compound (1), a 1× concentration of VEGF aptamer Compound (2), a combination of a 1× concentration T2-TrpRS and a 0.5× concentration of Compound (1), a combination of a 1× concentration T2-TrpRS and a 1× concentration of Compound (2), or a combination of a 1× concentration T2-TrpRS, a 0.5× concentration of Compound (1), and a 1× concentration of Compound (2), in groups of eight mice for each treatment regimen. As a control, another group of eight mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 6 and in FIGS. 22, 23, 24, 25, 26, 27, and 28.

TABLE 6

| | % Inhibition: | | | | | |
|---|---|---|---|---|---|---|
| | 0-10% | 10-25% | 25-50% | 50-75% | 75-100% | >95% | 100% |
| PBS | 100 | 0 | 0 | 0 | 0 | 0 | 0 |
| 0.5× Comp. (1) | 50 | 12.5 | 12.5 | 12.5 | 12.5 | 0 | 0 |
| 1× Comp. (2) | 37.5 | 25 | 12.5 | 25 | 0 | 0 | 0 |
| 1× T2-TrpRS | 50 | 25 | 12.5 | 12.5 | 0 | 0 | 0 |
| T2-TrpRS + Comp. (2) | 25 | 25 | 25 | 0 | 25 | 25 | 12.5 |
| T2-TrpRS + Comp. (1) | 50 | 0 | 0 | 0 | 50 | 37.5 | 25 |
| T2-TrpRS + (1) and (2) | 0 | 0 | 0 | 0 | 100 | 87.5 | 75 |

EXAMPLE 7

Treatment of Neonatal Mouse Eyes with a Combination of an Angiostatic Fragment of TrpRS, a VEGF Signaling Inhibitor, and an Integrin Signaling Inhibitor Following the General Procedure, the eyes of neonatal Balb/C mice were intravitreally injected on P4 with either a 1× concentration of T2-TrpRS, a 0.5× concentration of integrin signaling inhibitor Compound (1), a 1× concentration of VEGF aptamer Compound (2), a combination of a 0.5× concentration Compound (1) and a 1× concentration of Compound (2), or a combination of a 1× concentration T2-TrpRS, a 0.5× concentration of Compound (1), and a 1× concentration of Compound (2), in groups of eight mice for each treatment regimen. As a control, another group of six mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 7 and in FIGS. 29, 30, 31, 32, 33, and 34.

TABLE 7

| | % Inhibition: | | | | | | |
|---|---|---|---|---|---|---|---|
| | 0-10% | 10-25% | 25-50% | 50-75% | 75-100% | >95% | 100% |
| PBS | 100 | 0 | 0 | 0 | 0 | 0 | 0 |
| 0.5× Comp. (1) | 12.5 | 25 | 12.5 | 12.5 | 37.5 | 0 | 0 |
| 1× Comp. (2) | 25 | 25 | 0 | 12.5 | 37.5 | 0 | 0 |
| 1× T2-TrpRS | 25 | 12.5 | 12.5 | 0 | 50 | 12.5 | 0 |
| Comp. (1) + (2) | 0 | 12.5 | 12.5 | 25 | 50 | 25 | 25 |
| T2-TrpRS + (1) and (2) | 0 | 0 | 0 | 0 | 100 | 62.5 | 50 |

EXAMPLE 8

Treatment of Neonatal Mouse Eyes with a Combination of an Angiostatic Fragment of TrpRS and a VEGF Signaling Inhibitor Following the General Procedure, the eyes of neonatal Balb/C mice were intravitreally injected on P4 with either a 1× concentration of T2-TrpRS (ten mice), a 0.25× concentration of VEGF aptamer Compound (2) (eleven mice), or a combination of a 1× concentration T2-TrpRS and a 0.25× concentration of Compound (2) (eleven mice). As a control, another group of eight mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 8.

TABLE 8

| | % inhibition: | | | | | | |
|---|---|---|---|---|---|---|---|
| | 0-10% | 10-25% | 25-50% | 50-75% | 75-100% | >95% | 100% |
| PBS | 100 | 0 | 0 | 0 | 0 | 0 | 0 |
| 0.25× Comp. (2) | 54.5 | 36.4 | 0 | 0 | 9.1 | 0 | 0 |
| 1× T2-TrpRS | 30 | 30 | 20 | 10 | 10 | 0 | 0 |
| Combination | 18.2 | 18.2 | 9.1 | 18.2 | 27.3 | 0 | 0 |

EXAMPLE 9

Treatment of Neonatal Mouse Eyes with a Combination of an Angiostatic Fragment of TrpRS, a VEGF Signaling Inhibitor, and an Integrin Signaling Inhibitor Following the General Procedure, the eyes of neonatal Balb/C mice (in groups of eight mice each) were intravitreally injected on P4 with either a 1× concentration of T2-TrpRS, a 1× concentration of integrin signaling inhibitor Compound (1), a 1× concentration of VEGF aptamer Compound (2), a combination of a 1× concentration T2-TrpRS and a 1× concentration of Compound (1), a combination of a 1× concentration Compound (1) and a 1× concentration of Compound (2), or a combination of a 1× concentration T2-TrpRS, a 1× concentration of Compound (2), and a 1× concentration of Compound (2). As a control, another group of eight mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 9 and FIGS. 35-42.

TABLE 9

| | % Inhibition: | | | | | | |
|---|---|---|---|---|---|---|---|
| | 0-10% | 10-25% | 25-50% | 50-75% | 75-100% | >95% | 100% |
| PBS | 75 | 25 | 0 | 0 | 0 | 0 | 0 |
| 1× Comp. (1) | 25 | 12.5 | 12.5 | 37.5 | 12.5 | 0 | 0 |
| 1× Comp. (2) | 25 | 0 | 12.5 | 12.5 | 50 | 25 | 12.5 |
| 1× T2-TrpRS | 12.5 | 0 | 25 | 12.5 | 50 | 12.5 | 0 |
| Comp. (1) + T2-TrpRS | 0 | 12.5 | 12.5 | 25 | 50 | 25 | 12.5 |
| Comp. (1) + (2) | 12.5 | 12.5 | 0 | 12.5 | 62.5 | 62.5 | 50 |
| T2-TrpRS + Comp. (2) | 0 | 12.5 | 12.5 | 12.5 | 62.5 | 37.5 | 25 |
| T2-TrpRS + (1) + (2) | 0 | 25 | 0 | 0 | 75 | 75 | 62.5 |

EXAMPLE 10

Treatment of Neonatal Mouse Eyes with Varying Doses of an Angiostatic Fragment of TrpRS Following the General Procedure, the eyes of neonatal Balb/C mice (in groups of eight to twelve mice each) were intravitreally injected on P4 with T2-TrpRS, at concentrations of 0.1× (8 mice), 0.3× (12 mice), 1× (12 mice), 2× (12 mice), and 3× (12 mice). As a control, another group of 10 mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 10.

TABLE 10

| | % Inhibition: | | | | |
|---|---|---|---|---|---|
| | 0-10% | 10-25% | 25-50% | 50-75% | 75-100% |
| PBS | 100 | 0 | 0 | 0 | 0 |
| 0.1× T2-TrpRS | 75 | 25 | 0 | 0 | 0 |
| 0.3× T2-TrpRS | 33.3 | 16.7 | 8.3 | 16.7 | 25 |
| 1× T2-TrpRS | 8.3 | 16.7 | 25 | 8.7 | 41.7 |
| 2× T2-TrpRS | 8.3 | 25 | 0 | 16.7 | 41.7 |
| 3× T2-TrpRS | 66.7 | 25 | 8.7 | 0 | 0 |

EXAMPLE 11

Treatment of Neonatal Mouse Eyes with Varying Doses of an Angiostatic Fragment of TrpRS Following the General Procedure, the eyes of neonatal Balb/C mice (in groups of six to fourteen mice each) were intravitreally injected on P4 with T2-TrpRS, at concentrations of 0.3× (6 mice), 1× (14 mice), 2× (8 mice), 3× (7 mice), and 5× (6 mice). As a control, another group of 10 mice received only an intravitreal injection of PBS. At P12, the mice were euthanized and the retinas were removed from the injected eyes, stained, mounted and microscopically evaluated as described in the General Procedure. The vascularity of the secondary (outer retinal vascular) layer was evaluated based on the percentage of vascularization compared to the control eyes. The results are shown in Table 11.

TABLE 11

| | % Inhibition: | | | | |
|---|---|---|---|---|---|
| | 0-10% | 10-25% | 25-50% | 50-75% | 75-100% |
| PBS | 60 | 40 | 0 | 0 | 0 |
| 0.3× T2-TrpRS | 33.3 | 16.7 | 0 | 0 | 50 |
| 1× T2-TrpRS | 14.3 | 14.3 | 7.1 | 14.3 | 50 |
| 2× T2-TrpRS | 12.5 | 12.5 | 12.5 | 12.5 | 50 |
| 3× T2-TrpRS | 14.3 | 14.3 | 14.3 | 28.5 | 28.5 |
| 5× T2-TrpRS | 16.6 | 33.3 | 33.3 | 16.6 | 0 |

The data for mice exhibiting >95% and 100% inhibition in the foregoing Examples demonstrates that even compositions comprising at least two materials selected from the group consisting of an angiostatic fragment of TrpRS, a VEGF signaling inhibitor, and an integrin signaling inhibitor afford unexpectedly greater efficacy for inhibition of neovascularization in the neonatal mouse eye model than the expected levels of inhibition from the simple additive effects of the combination of individual components. This is also evident when the results of the various examples are combined as in Table 12, which compiles the results from the Examples at concentrations of 1× to 2× of integrin inhibitor Compound (1), 0.5× to 1× of VEGF aptamer Compound (2), and 1× of T2-TrpRS, as well as compositions of the present invention (inhibition values in bold type in Table 12) comprising combinations of at least two of Compound (1), Compound (2) and T2-TrpRS. The number of mice in each group is indicated in parenthesis for each grouping. The data in Table 12 clearly shows an unexpectedly higher level of inhibition of blood vessel formation in the deep vascular layer for mouse eyes treated with the compositions of the present invention compared to the inhibition levels of the treatments with the individual inhibitors by themselves or the numerical sum thereof.

TABLE 12

Composite Data from the Examples..

| | % Inhibition: | | | | | | |
|---|---|---|---|---|---|---|---|
| | 0-10% | 10-25% | 25-50% | 50-75% | 75-100% | >95% | 100% |
| PBS (38 mice) | 84.2 | 10.5 | 5.3 | 0 | 0 | 0 | 0 |
| 1×-2× Comp. (1) (30 mice) | 33.3 | 20 | 13.3 | 16.7 | 16.7 | 0 | 0 |
| 1× Comp. (2) (30 mice) | 39.1 | 20 | 7.6 | 11.9 | 21.4 | 4.7 | 2.4 |
| 1× T2-TrpRS (46 mice) | 23.9 | 17.4 | 15.2 | 8.7 | 34.8 | 8.7 | 2.2 |
| Comp. (1) + T2-TrpRS (22 mice) | 18.2 | 13.6 | 9.1 | 9.1 | 50 | 27.3 | 13.6 |
| Comp. (1) + (2) (16 mice) | 6.3 | 12.5 | 6.3 | 18.8 | 56.3 | 43.7 | 37.5 |
| T2-TrpRS + Comp. (2) (36 mice) | 5.6 | 11.1 | 13.9 | 8.3 | 61.1 | 33.3 | 19.4 |
| T2-TrpRS + (1) + (2) (24 mice) | 0 | 8.3 | 0 | 0 | 91.7 | 79.2 | 62.5 |

The results from Examples 10 and 11 (Tables 10 and 11) show that the efficacy of T2-TrpRS reached a maximum at about 1× to 2× concentration and did not provide any more than 50% of mice having 75-100% inhibition in the deep vascular layer. The efficacy began to fall off at 2× and greater concentration. Thus even with increasing dosages, T2 did not provide greater than about 50% efficacy at the 95-100% inhibition level.

EXAMPLE 12

Synergistic Effects of the Administration of T2-TrpRS Angiostatic Fragment, VEGF Aptamer and Peptidominetic $\alpha_v\beta_3$ and $\alpha_v\beta_5$ Integrin Signaling Inhibitor To study the effect of combining different angiostatic molecules, three angiostatic compounds known to target critical, but separate, angiogenic pathways were utilized: a small molecule integrin $\alpha_v\beta_3$ and $\alpha_v\beta_5$ antagonist (Compound (1); "EMD 472523" obtained from Merck KGaA, Darmstadt, Germany), a $VEGF_{165}$ antagonist (Compound (2); pegaptanib sodium), and a truncated form of Tryptophan tRNA synthetase (T2-TrpRS, obtained from Angiosyn Inc., La Jolla, Calif.). Although the exact mechanism of action for T2-TrpRS has not been fully elucidated, its mechanism of action is not directly linked to VEGF or integrin antagonism.

Figure 48:
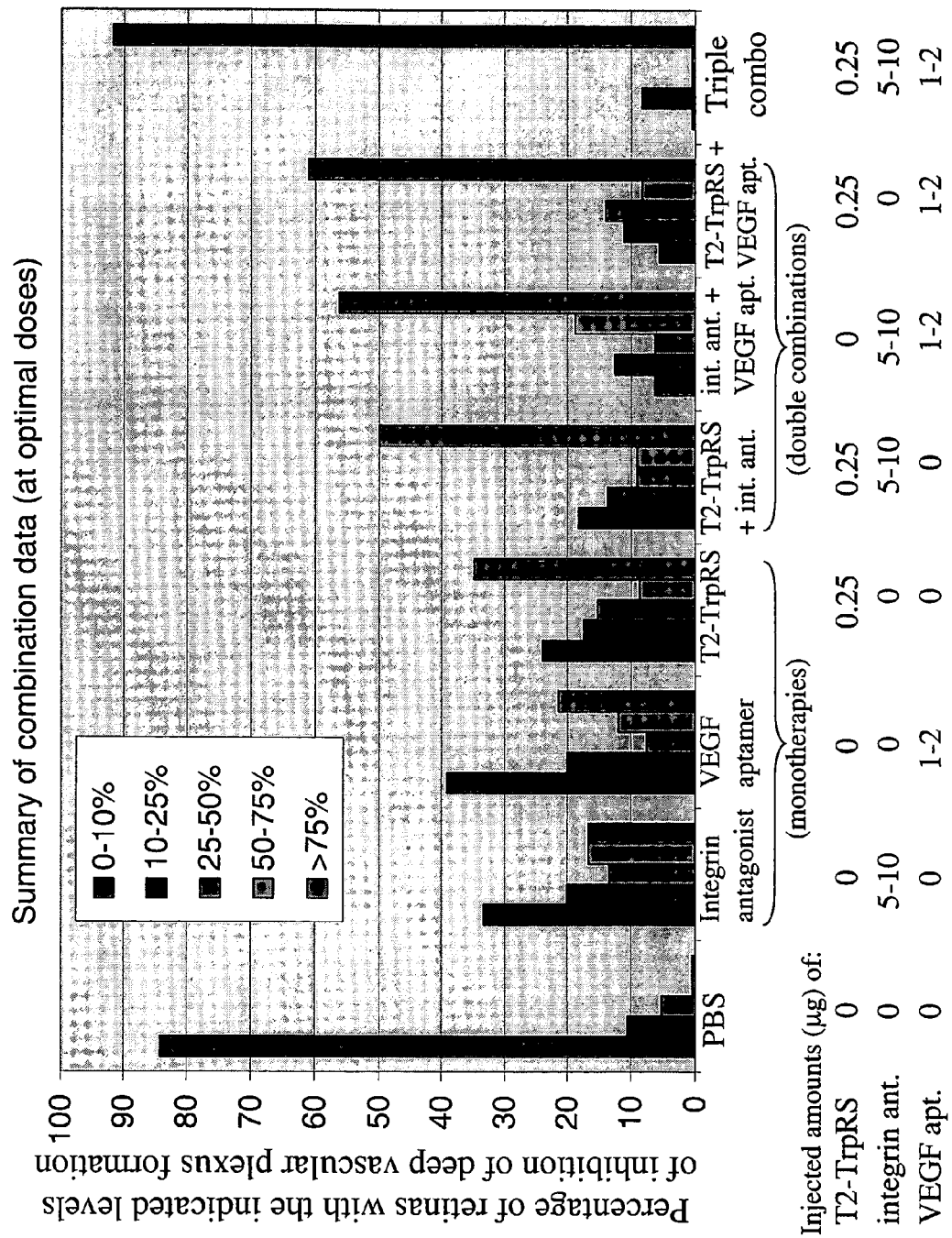
FIG. 48 is a graphical summary of data showing inhibition of deep vascular plexus formation at various combinations of therapies.
Figure 49:
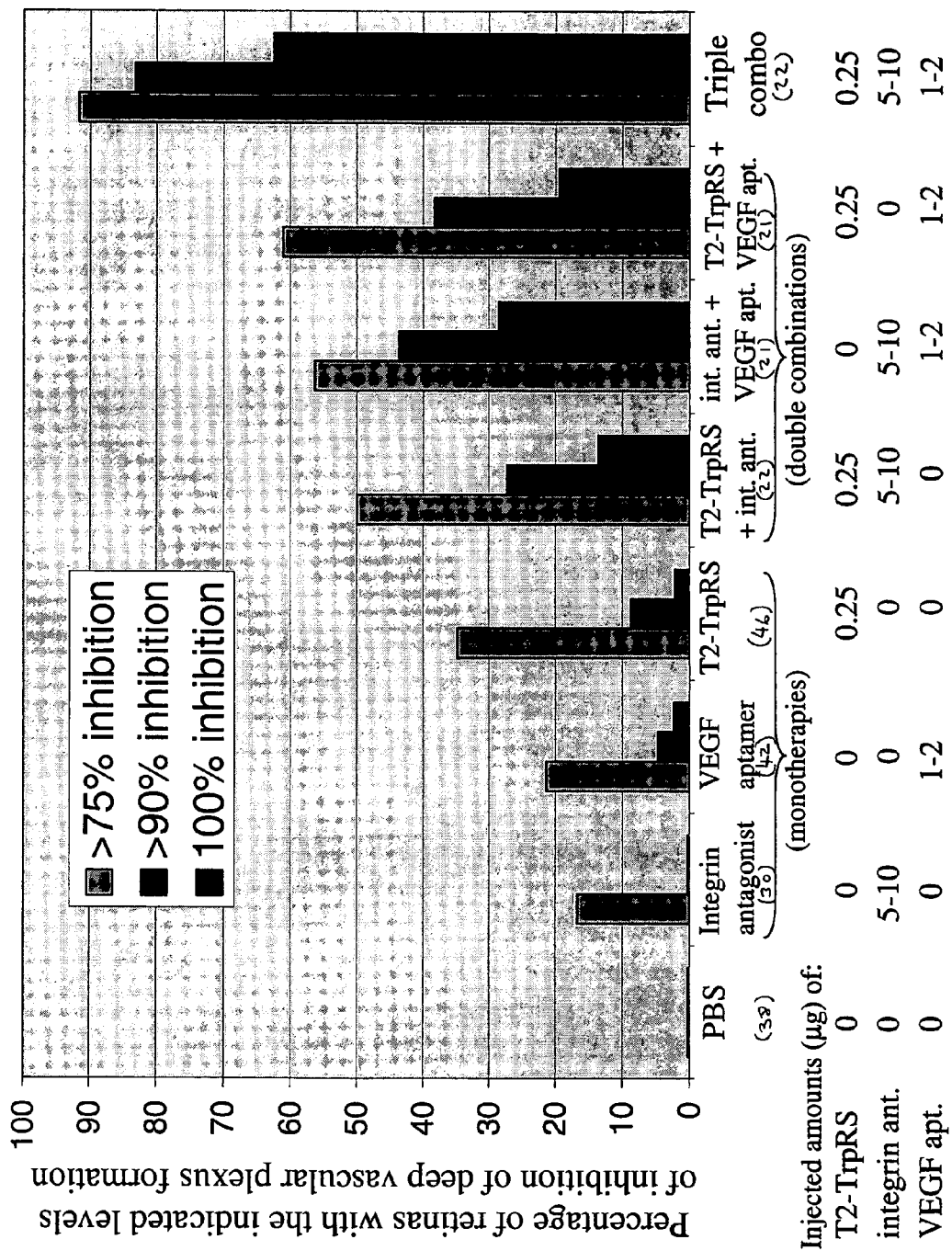
FIG. 49 is a graphical representation of data showing degree of inhibition of deep vascular plexus formation at various combinations of therapies.

The neonatal mouse retinal angiogenesis model was used to test the efficacy of each monotherapy, and various combinations of these individual compounds. As stated hereinabove, mice are born without a retinal vasculature. During the first three weeks after birth an adult-like vasculature develops. The retinal vasculature forms three distinct planar plexuses with the superficial vascular plexus developing during the first post-natal week. At post-natal day 8 (P8), the vessels of the superficial plexus branch and migrate toward the deep plexus at the outer edge of the inner nuclear layer. To test the angiostatic properties of each monotherapy or combination solution, intravitreal injections were performed at P7, when the formation of the superficial network is nearing completion, but before the formation of the deep plexuses has begun. The effects on formation of the deep vascular plexus were then analyzed five days later (P12). The degree of inhibition for each injected retina was scored as 0-10%, 10-25%, 25-50%, 50-75%, or 75-100% (FIG. 48) with the 75-100% inhibition group further separated into >90% and 100% inhibition levels (FIG. 49). The appearance of the previously formed primary vascular plexus, as well as the overall retinal morphology, were evaluated for signs of toxicity.

Sample preparation. The $\alpha_v\beta_3$ and $\alpha_v\beta_5$ integrin antagonist (Compound (1)) was stored as lyophilized powder in a desiccator at room temperature (I.A.) or −20° C. (V.A.), and solubilized in sterile, RNAse-free 1×PBS immediately before use. The VEGF aptamer (Compound (1)) was synthesized as a 40 kDa PEG conjugated compound (Transgenomic Inc, Boulder, Colo.) based on published information, Bridonneau, et al., *J. Chromatogr. B. Diomed. Sci. App.* 726: 237-47 (1999). The compound was determined to be pure by reverse phase liquid chromatography. Concentrations reported herein refer to the final concentration of the active VEGF aptamer rather than the total concentration of the PEG conjugated compound and were determined by spectrophotometric analysis at 260/280 nm. T2-TrpRS peptide was made as a recombinant compound as described in Otani, et al., *Proc. Nat'l. Acad. Sci., USA* 99: 178-183 (2002) and U.S. Provisional Application for Patent Ser. No. 60/598,019 filed Aug. 2, 2004, which are incorporated herein by reference in their entireties. Purified product was stored in 50% glycerol at −20° C., and dialyzed into sterile 1×PBS immediately before use. Combination solutions were prepared by initially creating 3× stock solutions of each individual compound. The compounds were then mixed together, and with PBS where appropriate, to make a final solution containing each desired compound at a concentration equivalent to each corresponding monotherapy concentration.

Intravitreal injections. All animal work adhered to strict protocol guidelines for the humane care and use of animals. Intravitreal injections were performed, the retinas were dissected, and the vasculature was visualized. OIR was induced according to the protocol described by Smith, et al., *Invest. Ophthalmol. Vis. Sci.,* 35: 101-111 (1994), by exposing postnatal day 7 (P7) pups and their mothers to an environment of 75% oxygen (hyperoxia) for 5 days, followed by a return to room air (normoxia). Intravitreal injections were performed at P12, immediately following return to normoxia and the retinas were analyzed at P17. Blood vessels were stained using isolectin GS—$IB_4$ from *Griffonia simplicifolia* (lectin GS), conjugated to Alexa Fluor 594 (Molecular Probes, 1:150 dilution in PBS). Confocal images were taken using a 4× objective lens, carefully focusing just above the inner limiting membrane of the retina, making the pre-laminar neovascular tufts prominent. Four overlapping images were acquired from each retina and each individual image was converted to a 2×2 inch size with 300 pixels per inch. The neovascular tuft areas were quantified by masked individuals using retinal whole mounts. Tufts were specifically selected, based on their characteristic appearance and the higher intensity of isolectin staining, using the magic wand tool in Adobe PHOTOSHOP® software. The total area in pixels was then determined. The areas of neovascular tuft formation were normalized to PBS-injected control OIR retinas.

Figure 43:
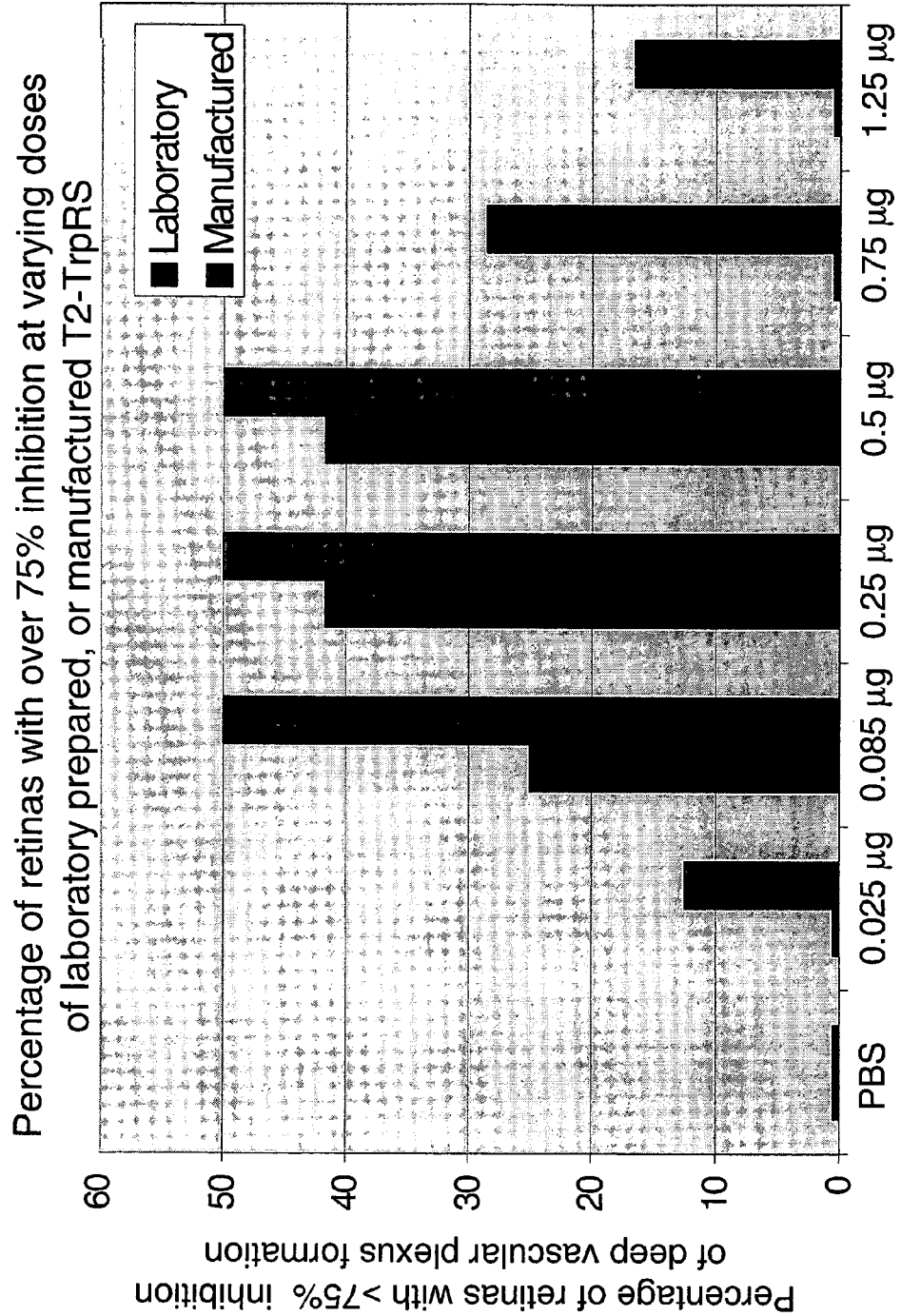
FIG. 43 is a graphical representation of data from a T2-TrpRS dosing experiment.
Figure 44:
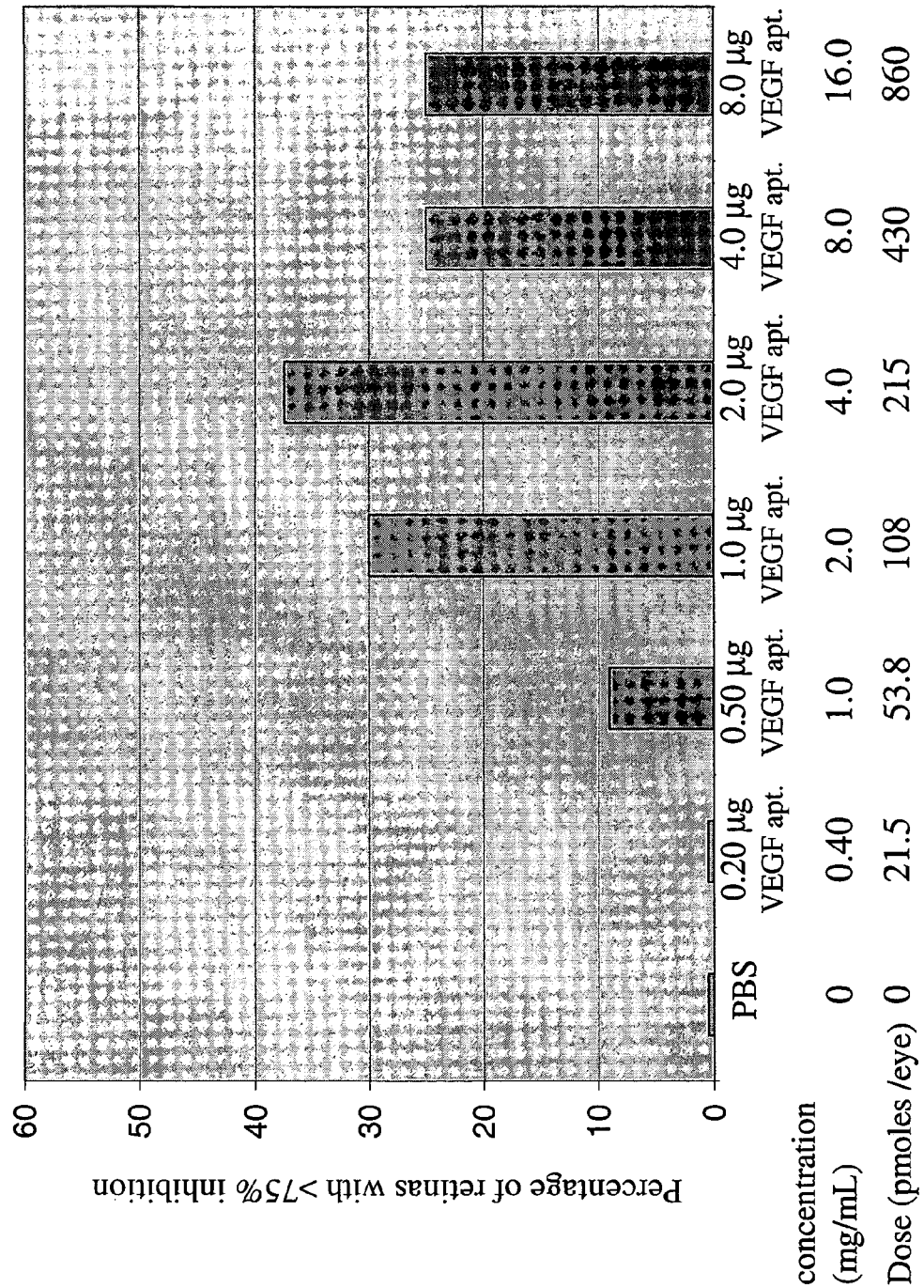
FIG. 44 is a graphical representation of data from a VEGF-aptamer dosing experiment.
Figure 45:
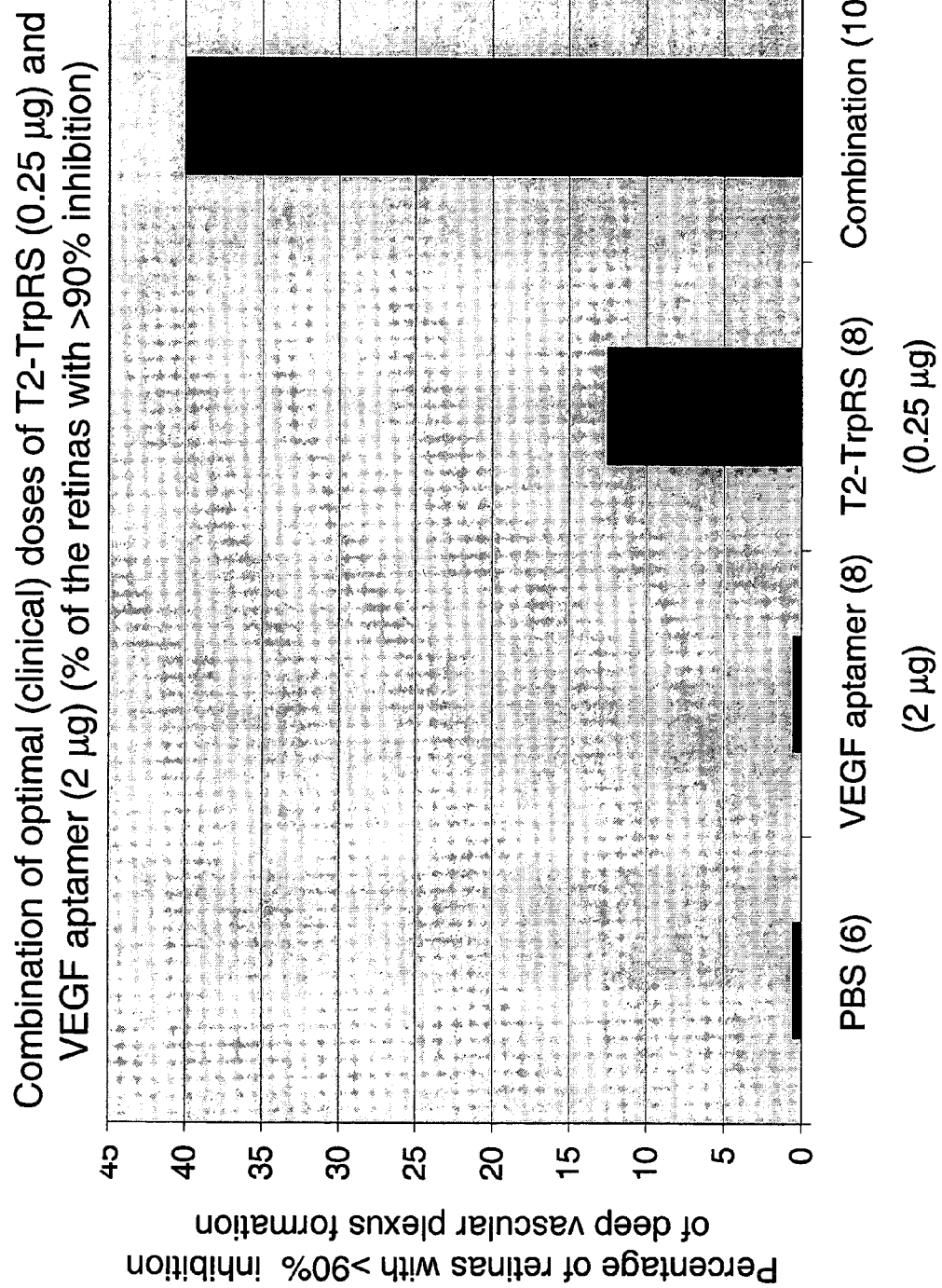
FIG. 45 is a graphical representation of data showing inhibition of deep vascular plexus formation as a function of administered optimal concentration of VEGF aptamer and T2-TrpRS compound, alone and in combination.
Figure 46:
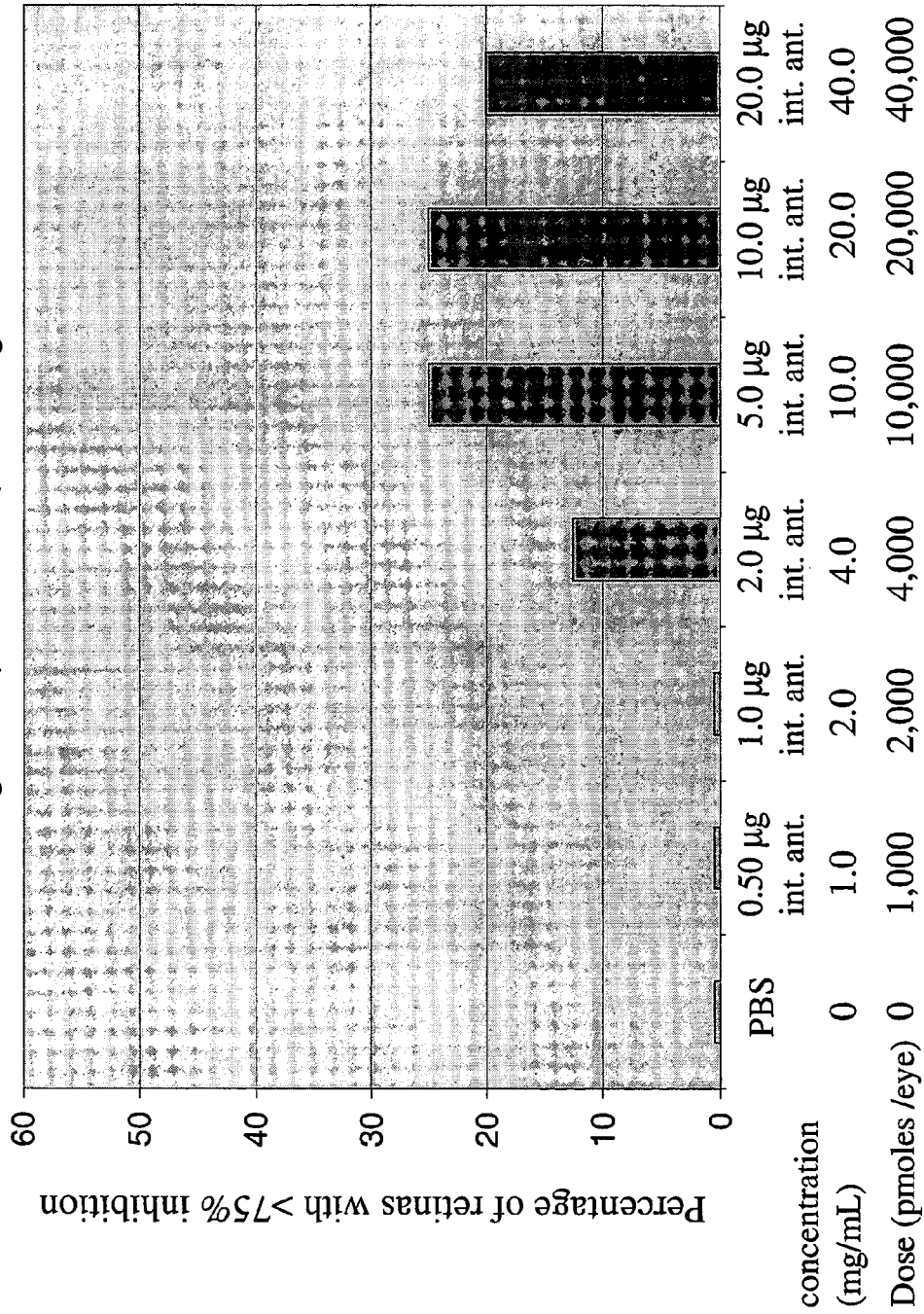
FIG. 46 is a graphical representation of data from $\alpha_v\beta_3$ and $\alpha_v\beta_5$ integrin antagonist dosing experiment.
Figure 47:
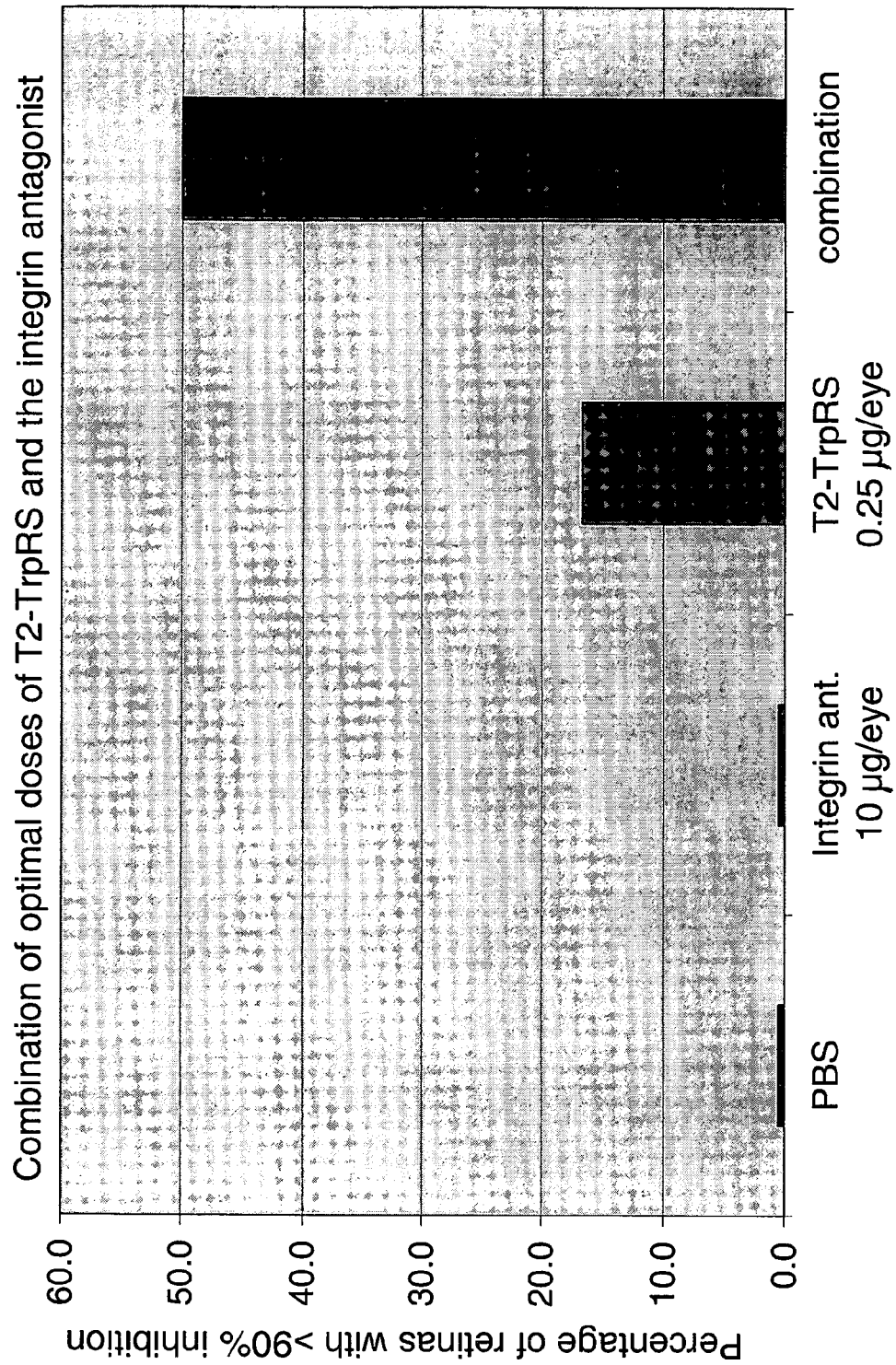
FIG. 47 is a graphical representation of data showing inhibition of deep vascular plexus formation as a function of administered optimal concentration of a small molecule $\alpha_v\beta_3$ and $\alpha_v\beta_5$ integrin antagonist and T2-TrpRS, alone and in combination.

Dosing. Dosing experiments were first performed to determine the maximum efficacy dose for each individual compound. Each compound was found to have a bell-shaped efficacy curve with optimal effective doses of 5-10 μg (10-20 nmoles) per eye for the integrin antagonist (FIG. 46), 1.0-2.0 μg (108-215 pmoles) per eye for the VEGF aptamer (FIG. 44), and 0.25-0.5 μg (5.2-10.4 pmoles) per eye for T2-TrpRS (FIG. 43). Single injections of each monotherapy at the optimal dose, and solutions containing appropriate combinations of each compound at equivalent doses were then performed to compare the angiostatic activities. At the maximum individual doses, around 35% of the retinas were unaffected by injection of either the integrin antagonist or the VEGF aptamer. The other 67% of the retinas basically fell evenly within the 10-25%, 25-50%, 50-75%, or 75%-100% range (Table 13A below). Inhibition of the deep vascular network with T2-TrpRS peptide was slightly better. 24% of the T2-TrpRS peptide injected retinas developed a normal, complete deep vascular plexus while 35% of the T2-TrpRS peptide injected retinas exhibited over 75% inhibition compared to 17% and 21% for the integrin antagonist and the VEGF aptamer respectively (Table 13A below). When the angiostatic compounds were injected in combination, the angiostatic effects on neovascularization were striking. Each dual combination, integrin antagonist+T2-TrpRS, integrin antagonist+VEGF aptamer, and T2-TrpRS+VEGF aptamer, demonstrated significant improvement of angiostatic activity over the monotherapies. Significantly fewer retinas were resistant to angiostatic treatment using the combination therapies. Neovascularization was inhibited by over 75% in a majority of the retinas treated with any of the dual combinations (Table 13 A below).

Figure 50:
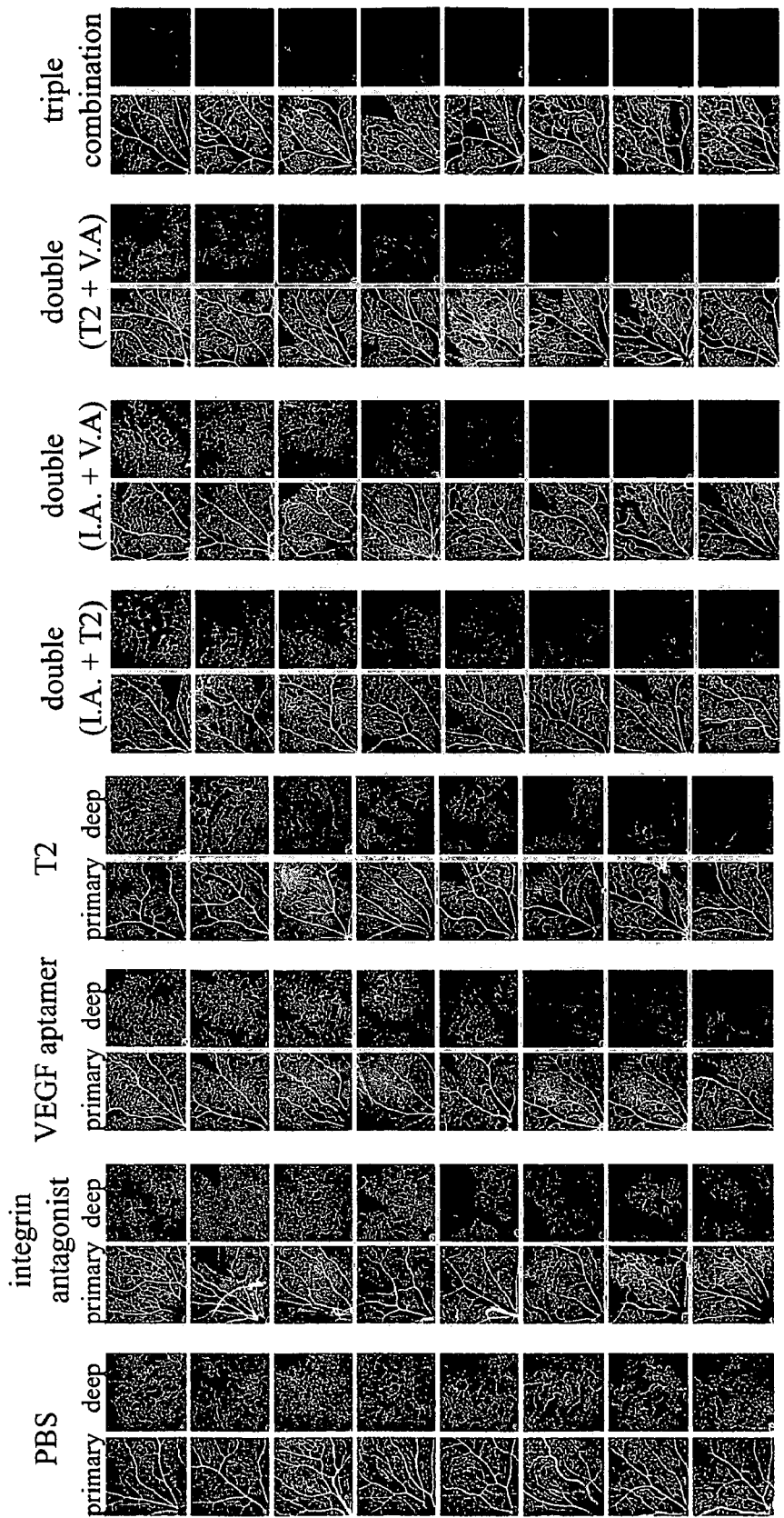
FIG. 50 is a series of photomicrographs of primary and deep (secondary) vascular layers at various therapies and combinations thereof at dosing levels shown in FIG. 49.
Figure 51:
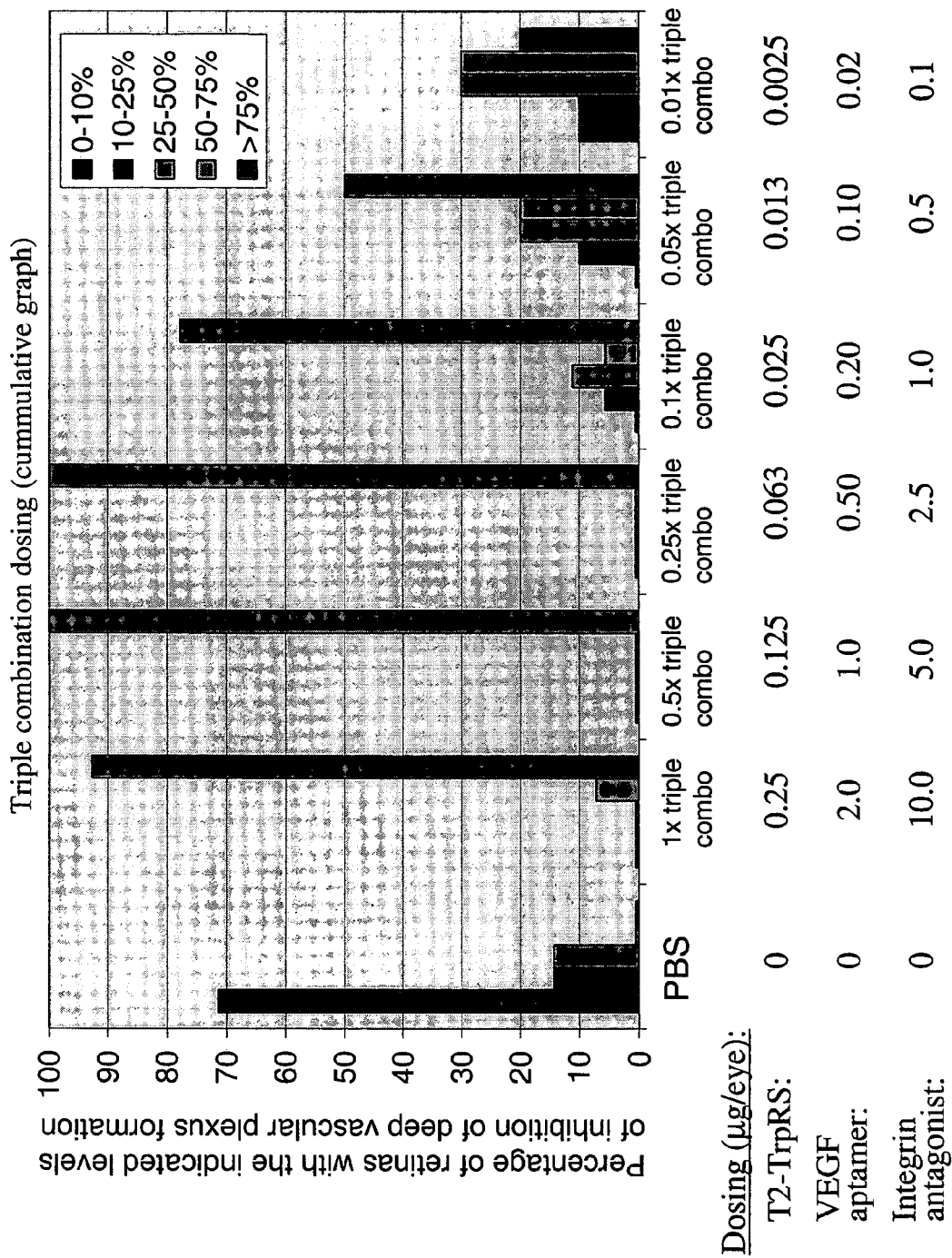
FIG. 51 is a graphical representation of levels of inhibition of vascular plexus formation with triple combination therapy at various dosage levels.

When all three compounds were injected together at the same optimal doses as the corresponding monotherapy injections (1x triple combination), over 90% of the retinas had >75% inhibition. Unlike the monotherapy or double combination-treated retinas, all retinas treated with the triple combination exhibited some degree of neovascular inhibition. In addition, only 8% of the injected retinas still had any significant levels of neovascularization at all. Nearly complete inhibition of angiogenesis was observed in the other 92% of the retinas injected with the triple combination compound (Table 13A below; FIG. 48). The differences in angistatic efficacy became even more pronounced when the >75% inhibition category was subcategorized into >90% inhibition and 100% inhibition levels (FIG. 49). Over 80% of the retinas injected with the triple combination had greater than 90% inhibition of deep vascular plexus formation and 63% had 100% inhibition of neovascularization where not even a single neovascular sprout could be observed. This is a substantial improvement over both the monotherapies which demonstrated 100% inhibition in <5% of the treated retinas and the dual combination therapies. In addition, the superficial vascular plexus of many of the triple combination-treated retinas resembled that of a normal P7 retina rather than P12 retinas, indicating that further vascular growth within the superficial plexus had also been prevented by the triple combination immediately following injection. Inhibition of superficial plexus growth was not observed in any mono- or dual-therapy treated retina. The more central vessels of the superficial vascular plexus that had already formed prior to injection remained normal, indicating negligible levels of toxicity to pre-existent vasculature. In addition, no signs of neuronal toxicity were observed, and the retinal morphology was unaltered, indicating that no observable negative side effects had occurred by injection of the triple combination solution. Images of the superficial and deep vascular plexuses from one complete representative experiment are shown in FIG. 50.

Figure 52:
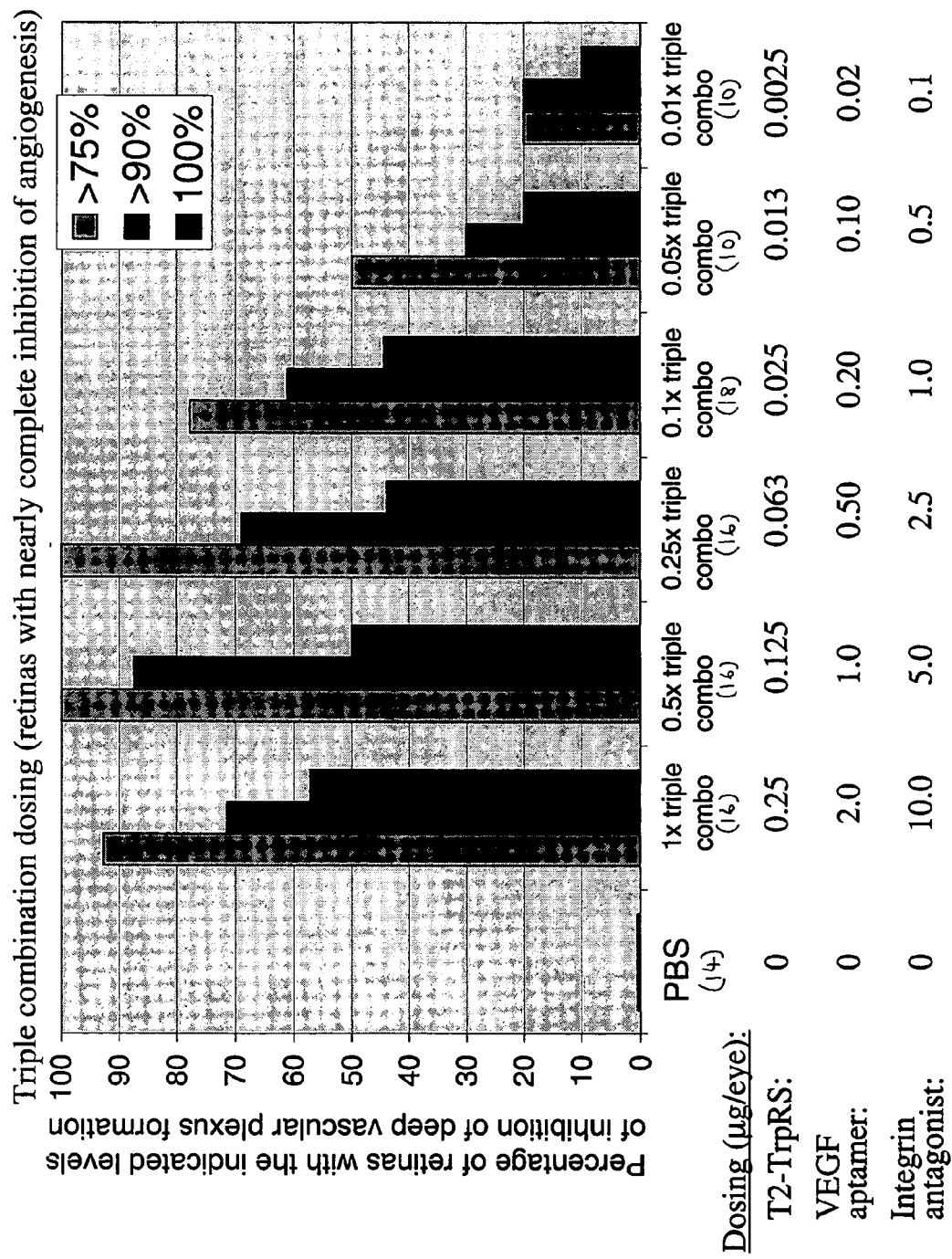
FIG. 52 is a graphical representation similar to FIG. 51 but showing inhibition of >75%, >90% and 100%.
Figure 53:
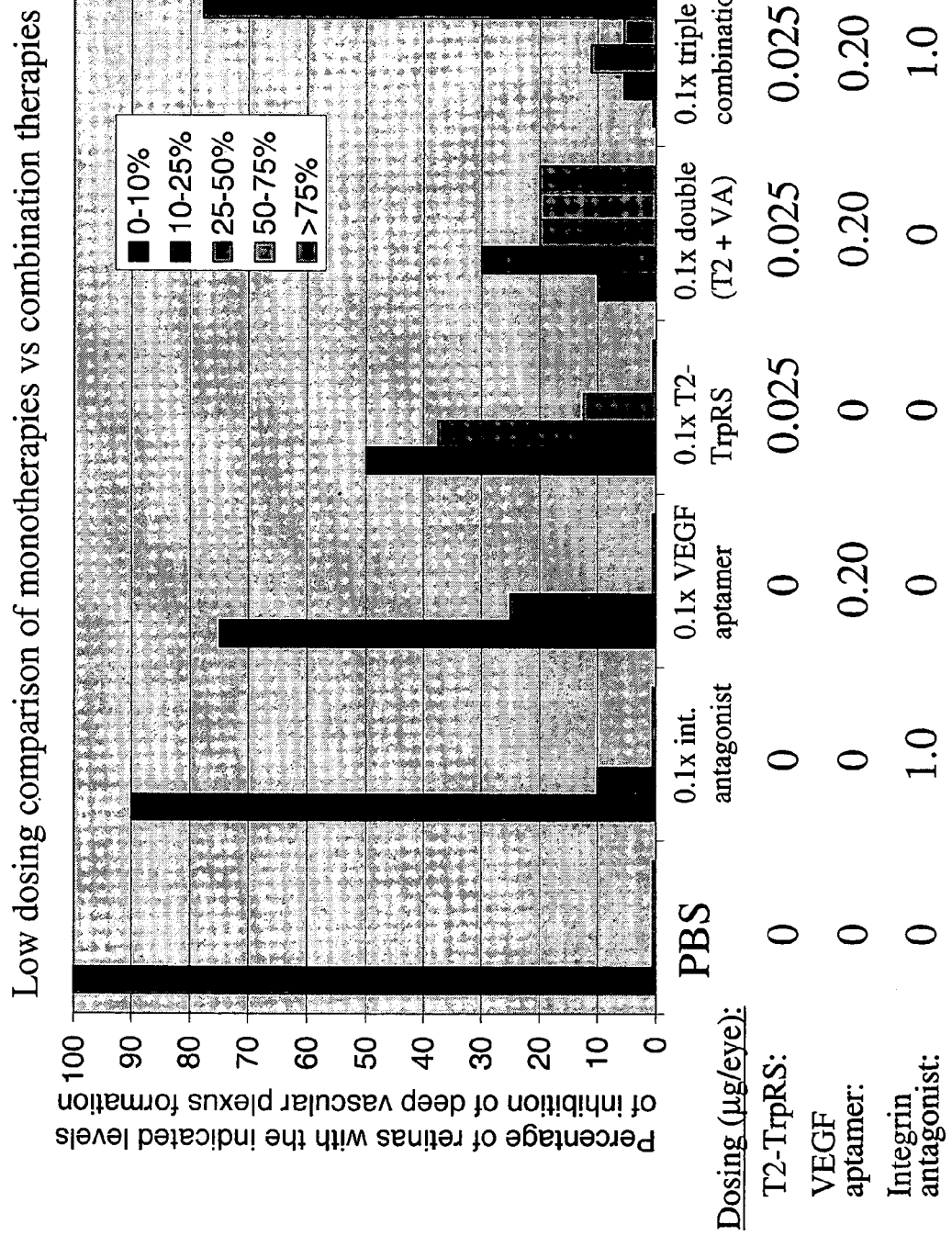
FIG. 53 is a graphical representation of levels of inhibition of vascular plexus formation comparing monotherapies versus combination therapies at various dosage levels.
Figure 54:
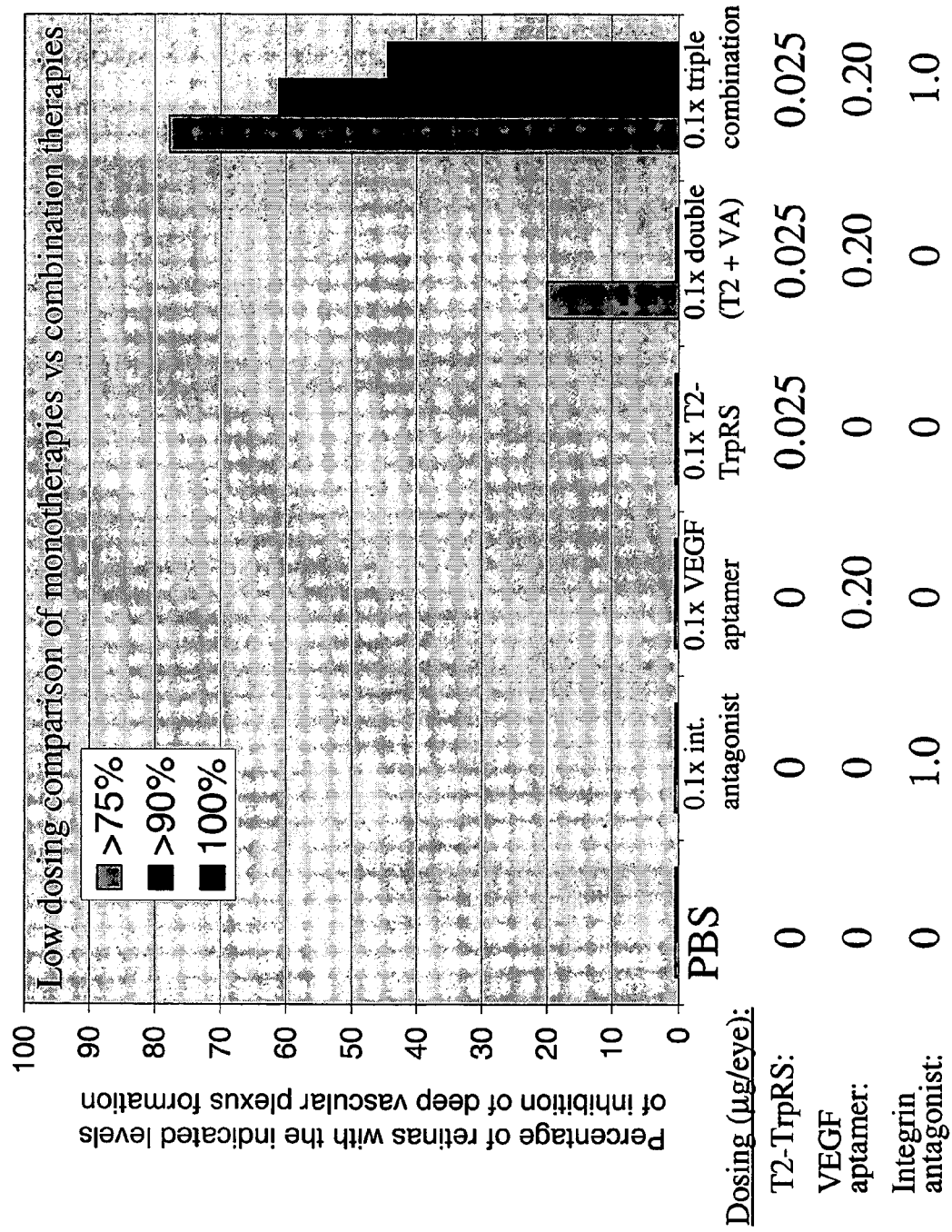
FIG. 54 is a graphical representation of >75%, >90% and 100% levels of inhibition of vascular plexus formation comparing monotherapies versus combination therapies at various dosage levels.
Figure 55:
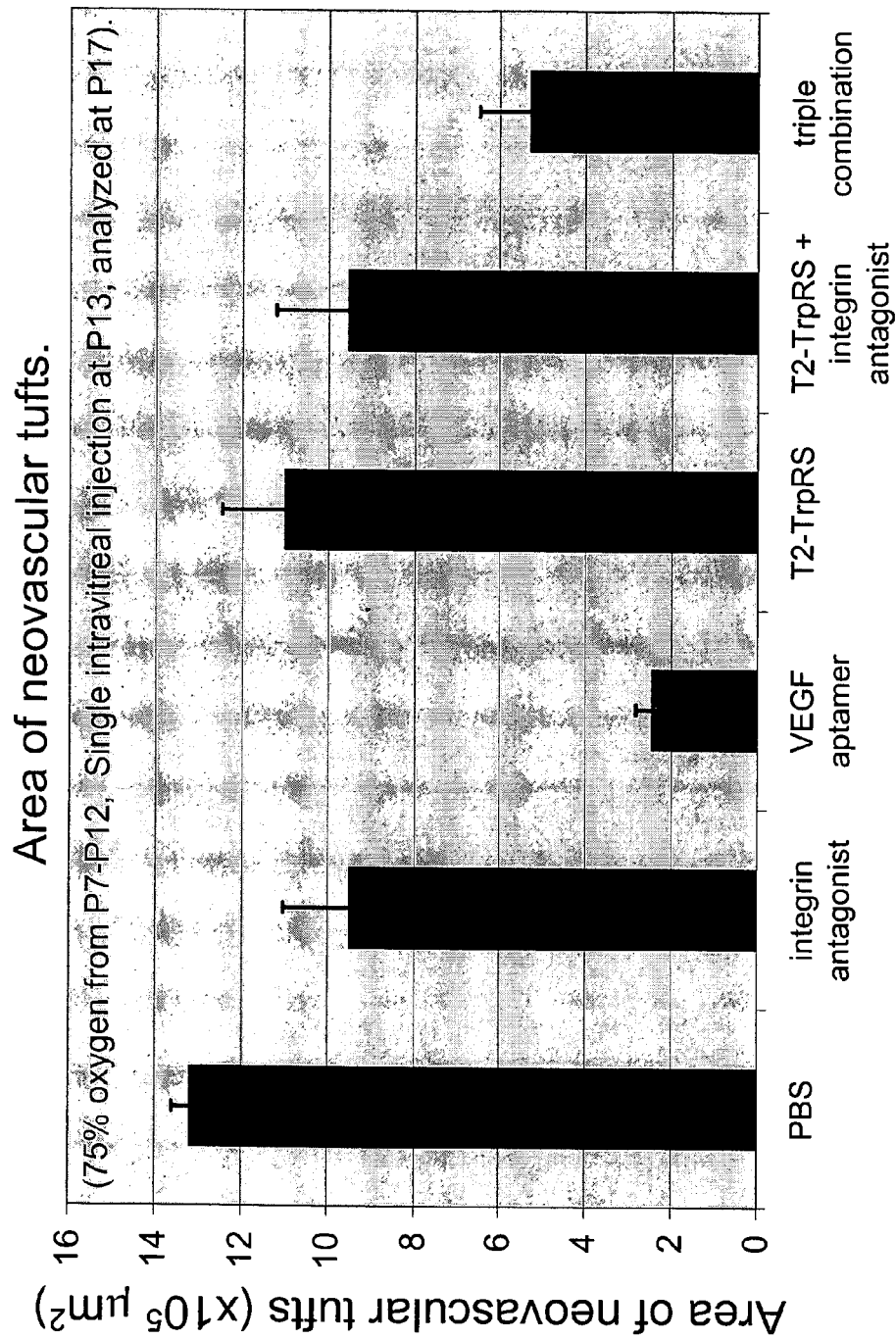
FIG. 55 is a graphical representation of data showing an area of neovascular tufts as a function of various monotherapies as well as a triple combination therapy utilizing a single injection of a therapeutic agent or agents.
Figure 56:
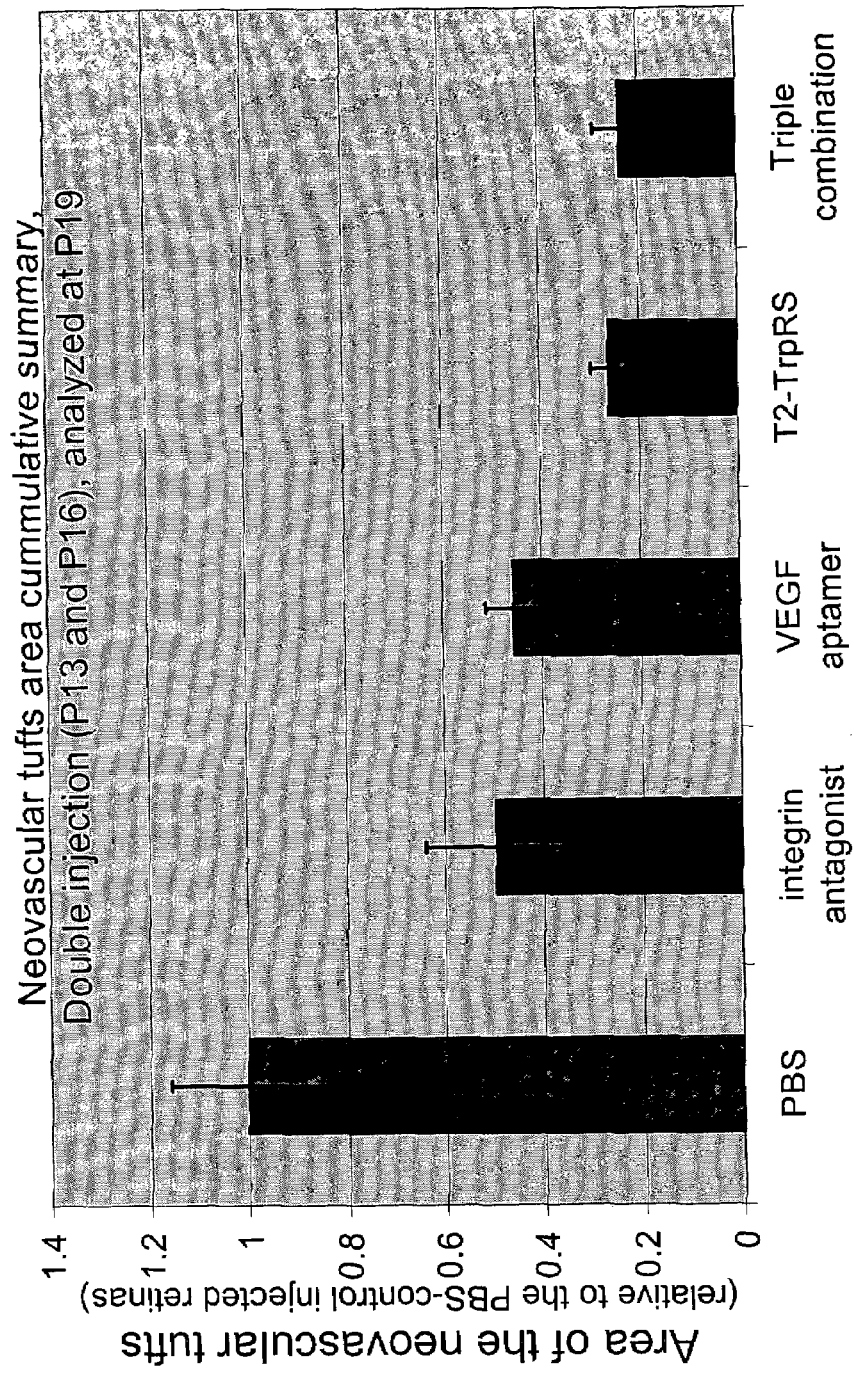
FIG. 56 is similar to FIG. 55, but shows data from a dual injection of a therapeutic agent or agents.

To analyze synergism, and to test if potent angiostatic activity could be maintained using lower doses of the triple combination, serial dilutions were tested. The triple combination was still highly effective at inhibiting angiogenesis when diluted up to 100-fold (0.01× triple combination) (Table 13B below; FIGS. 52 and 53). When the triple combination was made by combining the individual compounds at one-tenth their optimal dose, nearly 80% of the treated retinas still exhibited >75% inhibition, and 50% of the retinas exhibited complete (100%) inhibition of neovascularization. At the 0.1× concentrations (1 μg/eye integrin antagonist, 0.2 μg/eye VEGF aptamer, and 0.025 μg/eye T2-TrpRS), inhibition of neovascularization by the individual angiostatic compounds was negligible (Table 13C below; FIG. 54). Some efficacy was observed after injection of the double 0.1× T2-TrpRS and 0.1× VEGF aptamer combination. However, despite the fact that this combination was the most effective angiostatic of all the double combinations tested, the angiostatic activity was still minimal compared to the inhibition levels observed by injection of the 0.1× triple combination.

TABLE 13

| | N | 0-10% | 10-25% | 25-50% | 50-75% | >75% | >90% | 100% |
|---|---|---|---|---|---|---|---|---|
| A. Neonatal mouse angiogenesis model combination experiment Percentage of retinas with the indicated levels of neovascular inhibition ||||||||||
| Injection ||||||||||
| PBS | 38 | 84.2 | 10.5 | 5.3 | 0.0 | 0.0 | 0.0 | 0.0 |
| 5-10 μg integrin antagonist | 30 | 33.3 | 20.0 | 13.3 | 16.7 | 16.7 | 0.0 | 0.0 |
| 1-2 μg VEGF aptamer | 42 | 39.1 | 20.0 | 7.6 | 11.9 | 21.4 | 4.7 | 2.4 |
| 0.25 μg T2-TrpRS | 46 | 23.9 | 17.4 | 15.2 | 8.7 | 34.8 | 8.7 | 2.2 |
| T2-TrpRS + integrin ant. | 22 | 18.2 | 13.6 | 9.1 | 9.1 | 50.0 | 27.3 | 13.6 |
| Integrin ant. + VEGF apt. | 21 | 6.3 | 12.5 | 6.3 | 18.8 | 56.3 | 43.7 | 28.5 |
| T2-TrpRS + VEFG apt. | 36 | 5.6 | 11.1 | 13.9 | 8.3 | 61.1 | 38.3 | 19.4 |
| Triple combination | 24 | 0 | 8.3 | 0 | 0 | 91.7 | 83.2 | 62.6 |
| B. Triple combination serial dilution experiment ||||||||||
| Injection ||||||||||
| PBS | 14 | 71.4 | 14.3 | 14.3 | 0.0 | 0.0 | 0.0 | 0.0 |
| 1x Triple Combination | 16 | 0.0 | 0.0 | 0.0 | 7.1 | 92.8 | 71.4 | 57.1 |
| 0.5x Triple Combination | 16 | 0.0 | 0.0 | 0.0 | 0.5 | 100.0 | 87.5 | 50.0 |
| 0.25x Triple Combination | 16 | 0.0 | 0.0 | 0.0 | 0.5 | 100.0 | 68.8 | 43.8 |
| 0.1x Triple Combination. | 18 | 0.0 | 5.5 | 11.1 | 5.5 | 77.8 | 61.1 | 44.4 |
| 0.05x Triple Combination | 10 | 0.0 | 10.0 | 20.0 | 20.0 | 50.0 | 30.0 | 20.0 |
| 0.01x Triple Combination | 10 | 10.0 | 10.0 | 30.0 | 30.0 | 20.0 | 20.0 | 10.0 |
| C. Low dosing monotherapy vs. combination experiment ||||||||||
| Inhibition Levels: ||||||||||
| PBS | 8 | 100 | 0 | 0 | 0 | 0 | 0 | 0 |
| 0.1x integrin ant. (1.0 μg) | 10 | 90 | 10 | 0 | 0 | 0 | 0 | 0 |
| 0.1x VEGF apt. (0.20 μg) | 8 | 75 | 25 | 0 | 0 | 0 | 0 | 0 |
| 0.1x T2-TrpRS (0.025 μg) | 10 | 50 | 37.5 | 12.5 | 0 | 0 | 0 | 0 |
| 0.1x T2-TrpRS + VEFG apt. | 10 | 10 | 30 | 20.0 | 20 | 20 | 0 | 0 |
| 0.1x Triple Combination | 18 | 0 | 5.5 | 11.1 | 5.5 | 77.8 | 61.1 | 44.4 |

EXAMPLE 13

Synergistic Effects of a "Triple Therapy"

Figure 57:
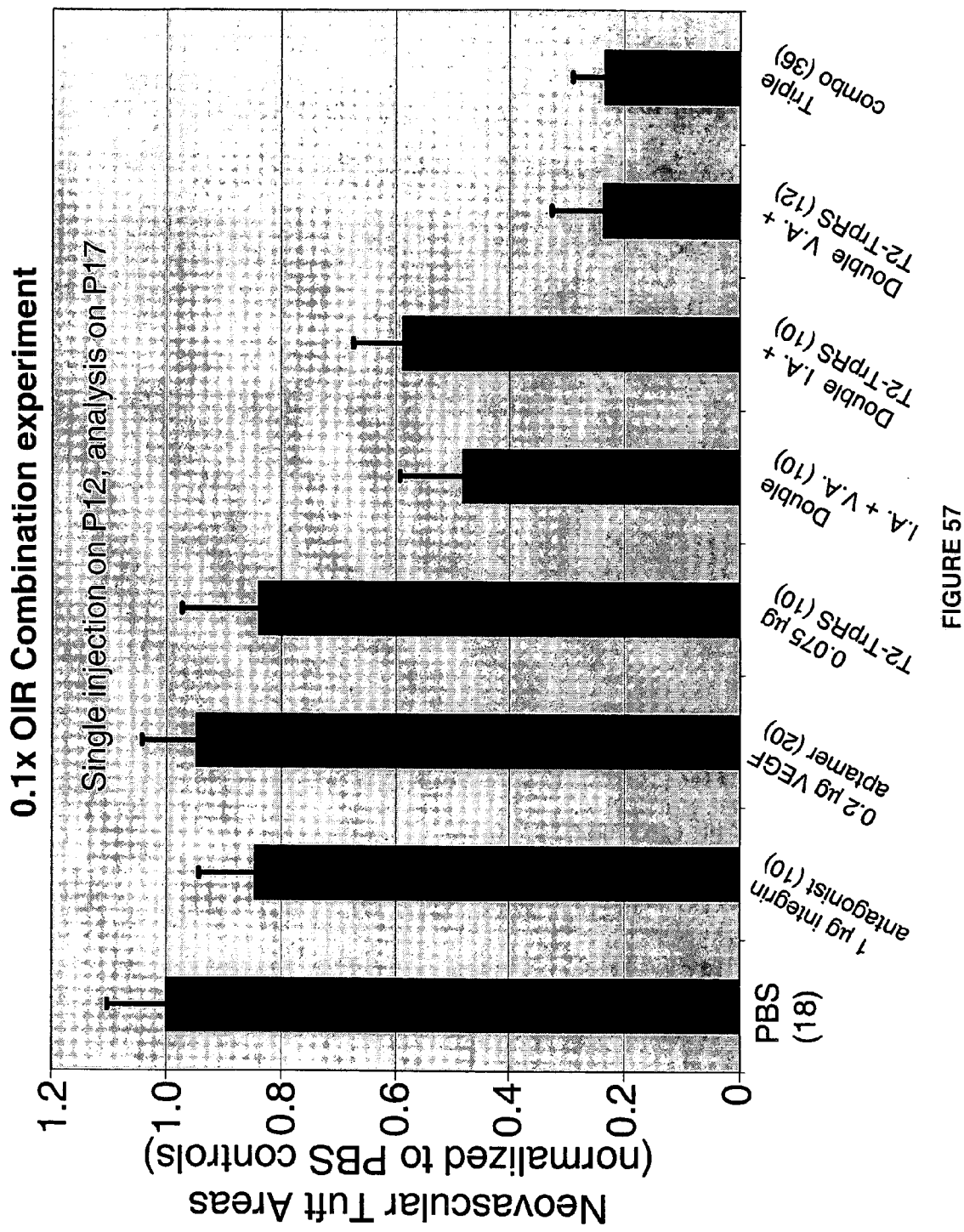
FIG. 57 is a graphical representation of data showing areas of neovascular tufts as a function of various monotherapies, dual therapies and a triple therapy.
Figure 58:
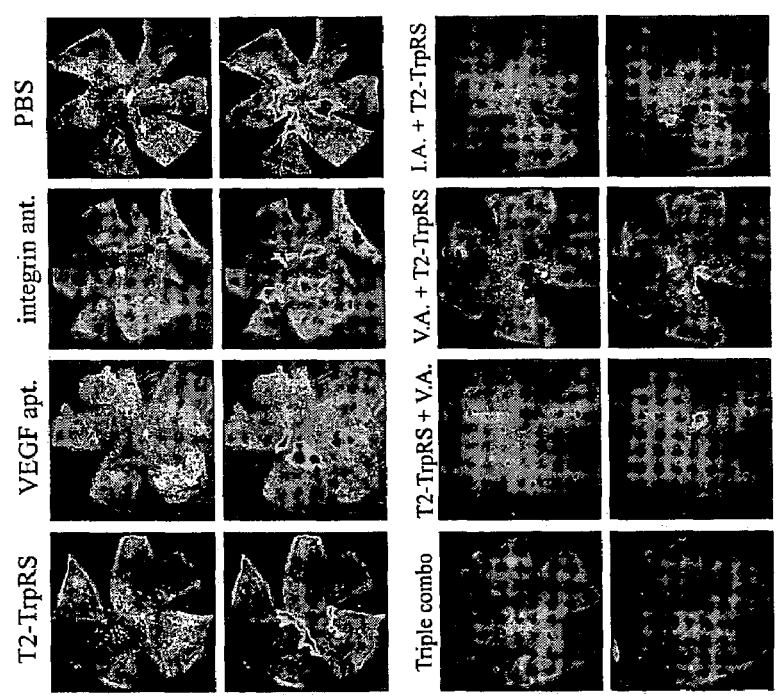
FIG. 58 is a series of photomicrographs showing mouse retinas treated with angiostatic compounds singly and in combination.

The mouse model of oxygen-induced retinopathy (OIR) described hereinabove is a well-accepted model of hypoxia-induced neovascularization in the retina. The associated vascular changes are consistent, reproducible and quantifiable. In recent years the use of this model has been extended to the general study of disease-related ischemic vasculopathies and related anti-angiogenic interventions. To study the synergistic properties of these angiostatic compounds in a more pathological model of angiogenesis, the effects of monotherapies and combination therapies on the formation of pathological neovascularization were tested in the mouse OIR model. For initial experiments, the optimal doses obtained from the neonatal angiogenesis model were used. In each case, combination therapies demonstrated improved angiostatic activities compared to the monotherapies. However, due to the angiostatic activities of each monotherapy, it was difficult to determine if the results of combining the various compounds were synergistic or simply additive. Thus, based on the results observed using the neonatal mouse retinal angiogenesis model which demonstrated equivalent efficacies of the combination therapies at relatively low doses, each monotherapy and the various combination therapies were tested at one-tenth of the optimal doses. Again, the concentration of each compound in the combination solutions was equivalent to the corresponding monotherapy concentration. At the lower concentrations, no significant inhibition of pathological neovascular tuft formation was observed following monotherapy treatments. However, significant reductions in neovascular tuft formations were observed using each double combination (FIG. 57). When the integrin antagonist was combined with T2-TrpRS peptide, pathological tuft formation was reduced by >50%. Combining the integrin antagonist with the VEFG aptamer reduced tuft formation by >40%. When T2-TrpRS peptide was combined with the VEGF aptamer, pathological neovascularization was reduced by nearly 80% compared to control-treated retinas. Many of the retinas treated with the double T2-TrpRS/VEGF aptamer combination looked nearly normal with virtually no pathological neovascularization evident (FIG. 58).

A dramatic increase in angiostatic activity by combining multiple angiostatic compounds that target distinct angiogenesis pathways has been demonstrated. Strong angiostatic activities were observed in both a developmental and a pathological model of angiogenesis even after combining the compounds at doses which have no monotherapeutic activity. This suggests a synergistic effect rather than simply an additive effect. This data also suggests that targeting multiple pathways may be required for effective clinical anti-angiogenic therapy and may provide a new paradigm for the treatment of neovascular diseases. Preferably, at least two anti-angiogenic therapies are combined (e.g., a combination of VEGF signaling inhibitor, such as a VEGF aptamer, combined with an angiostatic fragment of TrpRS, such as the T2 fragment of TrpRS, and optionally and integrin antagonist.

By targeting and inhibiting three separate angiogenic pathways, nearly complete inhibition of angiogenesis was obtained in two separate models of angiogenesis. The complete inhibition of neovascularization may be important for the effective treatment of angiogenesis-related diseases using angiostatic therapies. In our models, even the best results from monotherapy injections generally only blocked 50-75% of new vessel growth. This means that in most cases, a significant amount of neovascularization still developed. In contrast, two-thirds of the neonatal mouse retinas injected with the triple combination therapy had complete 100% inhibition of neovascular formation (Table 13). Similarly, in the OIR model of pathological angiogenesis, a large portion of the treated mice demonstrated little or no pathological neovascular tuft formation (FIG. 58). During cancer treatment, high levels of angiogenesis inhibition may be required to cause the complete starvation of tumor cells and prevent further tumor growth. Monotherapies that only inhibit 50% of neovascular growth are only likely to reduce, rather than eliminate, the oxygen and nutrients available to the rapidly growing tumor cells. Although this may initially slow growth, it may not be sufficient to prevent further tumor growth. In these instances, combination therapies that can achieve complete inhibition of neovascularization would greatly improve the results of anti-angiogenic therapies during cancer treatments. In addition, by using relatively low doses while maintaining strong angiostatic potential, the possibility of adverse side effects generated by angiostatic treatments can be minimized. Together, the foregoing data demonstrate the beneficial utility of combining different angiostatic molecules for the treatment of neovascularization associated with disease.

The compositions of the present invention, comprising an angiostatic fragment of tryptophanyl-tRNA synthetase (TrpRS), a vascular endothelial growth factor (VEGF) signaling inhibitor, and an integrin signaling inhibitor, and the methods of use thereof, provide a new and surprisingly efficacious treatment regimen for neovascular diseases, particularly for neovascular diseases of the eye.

EXAMPLE 14

Treatment of a Tumor

Glioblastoma multiform is an incurable malignant brain tumor, usually fatal within one year of diagnosis. The 9L rat gliosarcoma cell line is used as a model for malignant gliomas. In both forms of glioma, the tumor is highly vascularized and infiltrates into normal brain tissue. Untreated animal receiving a bolus of 9 L cells intracerebrally have a survival tie of approximately 3 weeks, once the tumor cells have been implanted. At day 0, intracerebral 9 L tumors were established by stereotactic inoculation of about 50,000 cells in about 2 μL of Delbecco's Modified Eagles's Medium (DMEM; Life Technologies, Gaithersburg, Md.) into the right frontal lobe of CD 344 Fisher rats that had previously been anesthetized with ketamine and xylazine.

At day 6, a 10 μl bolus of a composition of the invention (4.5 mg/l of T2-TrpRS, 30 mg/l of Compound (1), and 6 mg/l of Compound (2); pegaptanib sodium) was injected stereotactically over the course of about 2 minutes into the same region of the brain as the 9L cells were implanted. Follwing injection of the bolus, a pump was inserted into a subcutaneous pocket between the scapulae. A catheter connected via tubing to the pump was inserted into the same burr hole made for intorduction of the 9 L cells, and was fixed in place. Each pump had a flow rate of about 8 μl per hour. An additional quantity of the composition of the invention was continuously pumped into the brain of each animal for about 24 hours. The continuous pumping distributed the composition throughout the entire hemisphere of the brain in which the tumor cells had been implanted. Nine rats received the composition of the invention and nine rats received straight PBS as a control group.

Figure 60:
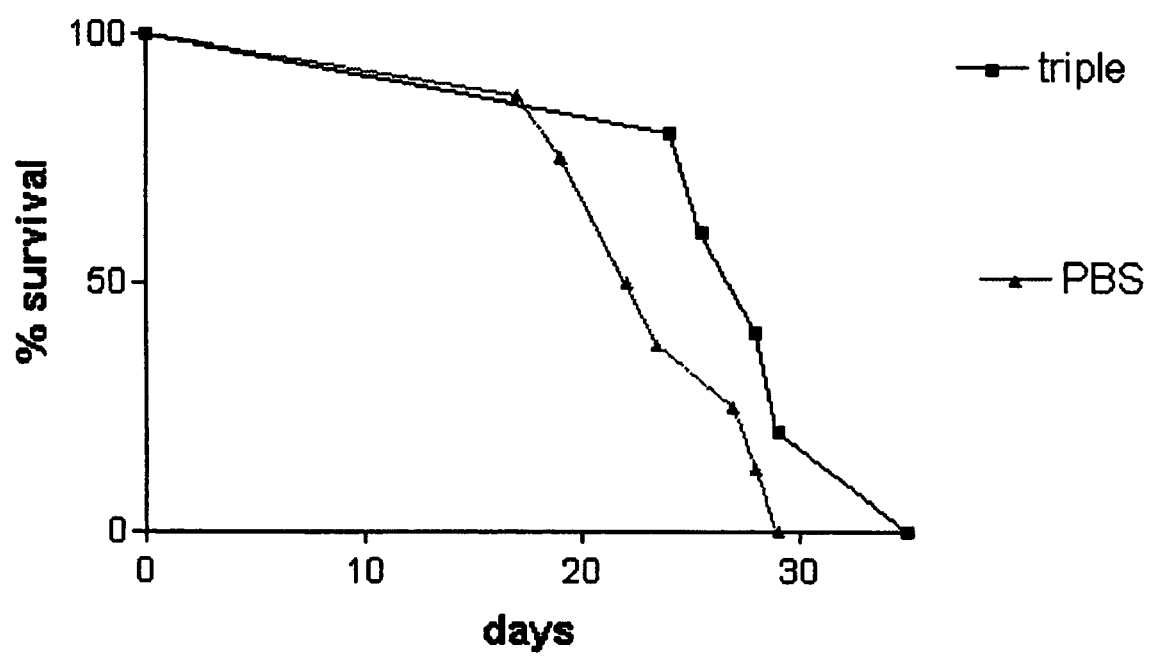
FIG. 60 shows a graph of survival for tumor bearing rats treated with a composition of the invention (squares) versus control rats treated only with PBS (triangles).

At day 13, an incision was made between the scapulae, and the pump was removed and replaced with an fresh pump. Treatment with the composition of the invention or PBS was resumed for an additional 24 hours with the new pump at the same pumping flow rates. There was a 21 percent increase in survival for rats treated with the composition of the invention compared to the PBS treated control group (See FIG. 60).

Numerous variations and modifications of the embodiments described above may be effected without departing from the spirit and scope of the novel features of the invention. No limitations with respect to the specific embodiments illustrated herein are intended or should be inferred.

We claim:

1. A composition suitable for treating a neovascular disease, which comprises a peptide consisting of SEQ ID NO: 1, pegaptanib sodium, and a compound having the formula of Compound (1):

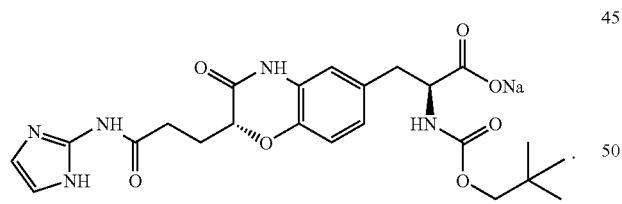

* * * * *

SEQUENCE LISTING

<160> NUMBER OF SEQ ID NOS: 5

<210> SEQ ID NO 1
<211> LENGTH: 379
<212> TYPE: PRT
<213> ORGANISM: homo sapiens

<400> SEQUENCE: 1

Met Ser Ala Lys Gly Ile Asp Tyr Asp Lys Leu Ile Val Arg Phe Gly
1               5                   10                  15

Ser Ser Lys Ile Asp Lys Glu Leu Ile Asn Arg Ile Glu Arg Ala Thr
            20                  25                  30

Gly Gln Arg Pro His His Phe Leu Arg Arg Gly Ile Phe Phe Ser His
        35                  40                  45

Arg Asp Met Asn Gln Val Leu Asp Ala Tyr Glu Asn Lys Lys Pro Phe
    50                  55                  60

Tyr Leu Tyr Thr Gly Arg Gly Pro Ser Ser Glu Ala Met His Val Gly
65                  70                  75                  80

His Leu Ile Pro Phe Ile Phe Thr Lys Trp Leu Gln Asp Val Phe Asn
                85                  90                  95

Val Pro Leu Val Ile Gln Met Thr Asp Asp Glu Lys Tyr Leu Trp Lys
            100                 105                 110

Asp Leu Thr Leu Asp Gln Ala Tyr Ser Tyr Ala Val Glu Asn Ala Lys
        115                 120                 125

Asp Ile Ile Ala Cys Gly Phe Asp Ile Asn Lys Thr Phe Ile Phe Ser
    130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
    210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
    290                 295                 300

Asp Val Ser Phe Met Tyr Leu Thr Phe Phe Leu Glu Asp Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350

His Gln Ala Arg Arg Lys Glu Val Thr Asp Glu Ile Val Lys Glu Phe

```
            355                 360                 365
Met Thr Pro Arg Lys Leu Ser Phe Asp Phe Gln
    370                 375

<210> SEQ ID NO 2
<211> LENGTH: 379
<212> TYPE: PRT
<213> ORGANISM: homo sapiens

<400> SEQUENCE: 2

Met Ser Ala Lys Gly Ile Asp Tyr Asp Lys Leu Ile Val Arg Phe Gly
  1               5                  10                  15

Ser Ser Lys Ile Asp Lys Glu Leu Ile Asn Arg Ile Glu Arg Ala Thr
                 20                  25                  30

Gly Gln Arg Pro His His Phe Leu Arg Arg Gly Ile Phe Phe Ser His
             35                  40                  45

Arg Asp Met Asn Gln Val Leu Asp Ala Tyr Glu Asn Lys Lys Pro Phe
         50                  55                  60

Tyr Leu Tyr Thr Gly Arg Gly Pro Ser Ser Glu Ala Met His Val Gly
 65                  70                  75                  80

His Leu Ile Pro Phe Ile Phe Thr Lys Trp Leu Gln Asp Val Phe Asn
                 85                  90                  95

Val Pro Leu Val Ile Gln Met Thr Asp Asp Glu Lys Tyr Leu Trp Lys
                100                 105                 110

Asp Leu Thr Leu Asp Gln Ala Tyr Gly Asp Ala Val Glu Asn Ala Lys
            115                 120                 125

Asp Ile Ile Ala Cys Gly Phe Asp Ile Asn Lys Thr Phe Ile Phe Ser
        130                 135                 140

Asp Leu Asp Tyr Met Gly Met Ser Ser Gly Phe Tyr Lys Asn Val Val
145                 150                 155                 160

Lys Ile Gln Lys His Val Thr Phe Asn Gln Val Lys Gly Ile Phe Gly
                165                 170                 175

Phe Thr Asp Ser Asp Cys Ile Gly Lys Ile Ser Phe Pro Ala Ile Gln
            180                 185                 190

Ala Ala Pro Ser Phe Ser Asn Ser Phe Pro Gln Ile Phe Arg Asp Arg
        195                 200                 205

Thr Asp Ile Gln Cys Leu Ile Pro Cys Ala Ile Asp Gln Asp Pro Tyr
    210                 215                 220

Phe Arg Met Thr Arg Asp Val Ala Pro Arg Ile Gly Tyr Pro Lys Pro
225                 230                 235                 240

Ala Leu Leu His Ser Thr Phe Phe Pro Ala Leu Gln Gly Ala Gln Thr
                245                 250                 255

Lys Met Ser Ala Ser Asp Pro Asn Ser Ser Ile Phe Leu Thr Asp Thr
            260                 265                 270

Ala Lys Gln Ile Lys Thr Lys Val Asn Lys His Ala Phe Ser Gly Gly
        275                 280                 285

Arg Asp Thr Ile Glu Glu His Arg Gln Phe Gly Gly Asn Cys Asp Val
    290                 295                 300

Asp Val Ser Phe Met Tyr Leu Thr Phe Phe Leu Glu Asp Asp Lys
305                 310                 315                 320

Leu Glu Gln Ile Arg Lys Asp Tyr Thr Ser Gly Ala Met Leu Thr Gly
                325                 330                 335

Glu Leu Lys Lys Ala Leu Ile Glu Val Leu Gln Pro Leu Ile Ala Glu
            340                 345                 350
```

-continued

His Gln Ala Arg Arg Lys Glu Val Thr Asp Glu Ile Val Lys Glu Phe
            355                 360                 365

Met Thr Pro Arg Lys Leu Ser Phe Asp Phe Gln
    370                 375

<210> SEQ ID NO 3
<211> LENGTH: 424
<212> TYPE: PRT
<213> ORGANISM: homo sapiens

<400> SEQUENCE: 3

Met Ser Tyr Lys Ala Ala Gly Glu Asp Tyr Lys Ala Asp Cys Pro
  1               5                  10                 15

Pro Gly Asn Pro Ala Pro Thr Ser Asn His Gly Pro Asp Ala Thr Glu
                20                  25                  30

Ala Glu Glu Asp Phe Val Asp Pro Trp Thr Val Gln Thr Ser Ser Ala
            35                  40                  45

Lys Gly Ile Asp Tyr Asp Lys Leu Ile Val Arg Phe Gly Ser Ser Lys
    50                  55                  60

Ile Asp Lys Glu Leu Ile Asn Arg Ile Glu Arg Ala Thr Gly Gln Arg
65                  70                  75                  80

Pro His His Phe Leu Arg Arg Gly Ile Phe Phe Ser His Arg Asp Met
                85                  90                  95

Asn Gln Val Leu Asp Ala Tyr Glu Asn Lys Lys Pro Phe Tyr Leu Tyr
                100                 105                 110

Thr Gly Arg Gly Pro Ser Ser Glu Ala Met His Val Gly His Leu Ile
            115                 120                 125

Pro Phe Ile Phe Thr Lys Trp Leu Gln Asp Val Phe Asn Val Pro Leu
    130                 135                 140

Val Ile Gln Met Thr Asp Asp Glu Lys Tyr Leu Trp Lys Asp Leu Thr
145                 150                 155                 160

Leu Asp Gln Ala Tyr Ser Tyr Ala Val Glu Asn Ala Lys Asp Ile Ile
                165                 170                 175

Ala Cys Gly Phe Asp Ile Asn Lys Thr Phe Ile Phe Ser Asp Leu Asp
            180                 185                 190

Tyr Met Gly Met Ser Ser Gly Phe Tyr Lys Asn Val Val Lys Ile Gln
    195                 200                 205

Lys His Val Thr Phe Asn Gln Val Lys Gly Ile Phe Gly Phe Thr Asp
    210                 215                 220

Ser Asp Cys Ile Gly Lys Ile Ser Phe Pro Ala Ile Gln Ala Ala Pro
225                 230                 235                 240

Ser Phe Ser Asn Ser Phe Pro Gln Ile Phe Arg Asp Arg Thr Asp Ile
                245                 250                 255

Gln Cys Leu Ile Pro Cys Ala Ile Asp Gln Asp Pro Tyr Phe Arg Met
            260                 265                 270

Thr Arg Asp Val Ala Pro Arg Ile Gly Tyr Pro Lys Pro Ala Leu Leu
    275                 280                 285

His Ser Thr Phe Phe Pro Ala Leu Gln Gly Ala Gln Thr Lys Met Ser
    290                 295                 300

Ala Ser Asp Pro Asn Ser Ser Ile Phe Leu Thr Asp Thr Ala Lys Gln
305                 310                 315                 320

Ile Lys Thr Lys Val Asn Lys His Ala Phe Ser Gly Gly Arg Asp Thr
                325                 330                 335

Ile Glu Glu His Arg Gln Phe Gly Gly Asn Cys Asp Val Asp Val Ser
            340                 345                 350

```
Phe Met Tyr Leu Thr Phe Phe Leu Glu Asp Asp Lys Leu Glu Gln
        355                 360                 365

Ile Arg Lys Asp Tyr Thr Ser Gly Ala Met Leu Thr Gly Glu Leu Lys
        370                 375                 380

Lys Ala Leu Ile Glu Val Leu Gln Pro Leu Ile Ala Glu His Gln Ala
385                 390                 395                 400

Arg Arg Lys Glu Val Thr Asp Glu Ile Val Lys Glu Phe Met Thr Pro
                405                 410                 415

Arg Lys Leu Ser Phe Asp Phe Gln
            420

<210> SEQ ID NO 4
<211> LENGTH: 401
<212> TYPE: PRT
<213> ORGANISM: homo sapiens

<400> SEQUENCE: 4

Ser Asn His Gly Pro Asp Ala Thr Glu Ala Glu Asp Phe Val Asp
 1               5                  10                  15

Pro Trp Thr Val Gln Thr Ser Ser Ala Lys Gly Ile Asp Tyr Asp Lys
                20                  25                  30

Leu Ile Val Arg Phe Gly Ser Ser Lys Ile Asp Lys Glu Leu Ile Asn
            35                  40                  45

Arg Ile Glu Arg Ala Thr Gly Gln Arg Pro His His Phe Leu Arg Arg
        50                  55                  60

Gly Ile Phe Phe Ser His Arg Asp Met Asn Gln Val Leu Asp Ala Tyr
65                  70                  75                  80

Glu Asn Lys Lys Pro Phe Tyr Leu Tyr Thr Gly Arg Gly Pro Ser Ser
                85                  90                  95

Glu Ala Met His Val Gly His Leu Ile Pro Phe Ile Phe Thr Lys Trp
            100                 105                 110

Leu Gln Asp Val Phe Asn Val Pro Leu Val Ile Gln Met Thr Asp Asp
        115                 120                 125

Glu Lys Tyr Leu Trp Lys Asp Leu Thr Leu Asp Gln Ala Tyr Ser Tyr
    130                 135                 140

Ala Val Glu Asn Ala Lys Asp Ile Ile Ala Cys Gly Phe Asp Ile Asn
145                 150                 155                 160

Lys Thr Phe Ile Phe Ser Asp Leu Asp Tyr Met Gly Met Ser Ser Gly
                165                 170                 175

Phe Tyr Lys Asn Val Val Lys Ile Gln Lys His Val Thr Phe Asn Gln
            180                 185                 190

Val Lys Gly Ile Phe Gly Phe Thr Asp Ser Asp Cys Ile Gly Lys Ile
        195                 200                 205

Ser Phe Pro Ala Ile Gln Ala Ala Pro Ser Phe Ser Asn Ser Phe Pro
    210                 215                 220

Gln Ile Phe Arg Asp Arg Thr Asp Ile Gln Cys Leu Ile Pro Cys Ala
225                 230                 235                 240

Ile Asp Gln Asp Pro Tyr Phe Arg Met Thr Arg Asp Val Ala Pro Arg
                245                 250                 255

Ile Gly Tyr Pro Lys Pro Ala Leu Leu His Ser Thr Phe Phe Pro Ala
            260                 265                 270

Leu Gln Gly Ala Gln Thr Lys Met Ser Ala Ser Asp Pro Asn Ser Ser
        275                 280                 285

Ile Phe Leu Thr Asp Thr Ala Lys Gln Ile Lys Thr Lys Val Asn Lys
```

```
                    290                 295                 300
His Ala Phe Ser Gly Gly Arg Asp Thr Ile Glu Glu His Arg Gln Phe
305                 310                 315                 320

Gly Gly Asn Cys Asp Val Asp Val Ser Phe Met Tyr Leu Thr Phe Phe
                325                 330                 335

Leu Glu Asp Asp Asp Lys Leu Glu Gln Ile Arg Lys Asp Tyr Thr Ser
                340                 345                 350

Gly Ala Met Leu Thr Gly Glu Leu Lys Lys Ala Leu Ile Glu Val Leu
                355                 360                 365

Gln Pro Leu Ile Ala Glu His Gln Ala Arg Arg Lys Glu Val Thr Asp
                370                 375                 380

Glu Ile Val Lys Glu Phe Met Thr Pro Arg Lys Leu Ser Phe Asp Phe
385                 390                 395                 400

Gln

<210> SEQ ID NO 5
<211> LENGTH: 471
<212> TYPE: PRT
<213> ORGANISM: homo sapiens

<400> SEQUENCE: 5

Met Pro Asn Ser Glu Pro Ala Ser Leu Leu Glu Leu Phe Asn Ser Ile
1               5                   10                  15

Ala Thr Gln Gly Glu Leu Val Arg Ser Leu Lys Ala Gly Asn Ala Ser
                20                  25                  30

Lys Asp Glu Ile Asp Ser Ala Val Lys Met Leu Val Ser Leu Lys Met
            35                  40                  45

Ser Tyr Lys Ala Ala Ala Gly Glu Asp Tyr Lys Ala Asp Cys Pro Pro
50                  55                  60

Gly Asn Pro Ala Pro Thr Ser Asn His Gly Pro Asp Ala Thr Glu Ala
65                  70                  75                  80

Glu Glu Asp Phe Val Asp Pro Trp Thr Val Gln Thr Ser Ser Ala Lys
                85                  90                  95

Gly Ile Asp Tyr Asp Lys Leu Ile Val Arg Phe Gly Ser Ser Lys Ile
                100                 105                 110

Asp Lys Glu Leu Ile Asn Arg Ile Glu Arg Ala Thr Gly Gln Arg Pro
            115                 120                 125

His His Phe Leu Arg Arg Gly Ile Phe Phe Ser His Arg Asp Met Asn
130                 135                 140

Gln Val Leu Asp Ala Tyr Glu Asn Lys Lys Pro Phe Tyr Leu Tyr Thr
145                 150                 155                 160

Gly Arg Gly Pro Ser Ser Glu Ala Met His Val Gly His Leu Ile Pro
                165                 170                 175

Phe Ile Phe Thr Lys Trp Leu Gln Asp Val Phe Asn Val Pro Leu Val
            180                 185                 190

Ile Gln Met Thr Asp Asp Glu Lys Tyr Leu Trp Lys Asp Leu Thr Leu
            195                 200                 205

Asp Gln Ala Tyr Ser Tyr Ala Val Glu Asn Ala Lys Asp Ile Ile Ala
210                 215                 220

Cys Gly Phe Asp Ile Asn Lys Thr Phe Ile Phe Ser Asp Leu Asp Tyr
225                 230                 235                 240

Met Gly Met Ser Ser Gly Phe Tyr Lys Asn Val Val Lys Ile Gln Lys
                245                 250                 255

His Val Thr Phe Asn Gln Val Lys Gly Ile Phe Gly Phe Thr Asp Ser
```

```
                        260                 265                 270
Asp Cys Ile Gly Lys Ile Ser Phe Pro Ala Ile Gln Ala Ala Pro Ser
            275                 280                 285

Phe Ser Asn Ser Phe Pro Gln Ile Phe Arg Asp Arg Thr Asp Ile Gln
        290                 295                 300

Cys Leu Ile Pro Cys Ala Ile Asp Gln Asp Pro Tyr Phe Arg Met Thr
305                 310                 315                 320

Arg Asp Val Ala Pro Arg Ile Gly Tyr Pro Lys Pro Ala Leu Leu His
                325                 330                 335

Ser Thr Phe Phe Pro Ala Leu Gln Gly Ala Gln Thr Lys Met Ser Ala
            340                 345                 350

Ser Asp Pro Asn Ser Ser Ile Phe Leu Thr Asp Thr Ala Lys Gln Ile
        355                 360                 365

Lys Thr Lys Val Asn Lys His Ala Phe Ser Gly Gly Arg Asp Thr Ile
    370                 375                 380

Glu Glu His Arg Gln Phe Gly Gly Asn Cys Asp Val Asp Val Ser Phe
385                 390                 395                 400

Met Tyr Leu Thr Phe Phe Leu Glu Asp Asp Asp Lys Leu Glu Gln Ile
                405                 410                 415

Arg Lys Asp Tyr Thr Ser Gly Ala Met Leu Thr Gly Glu Leu Lys Lys
            420                 425                 430

Ala Leu Ile Glu Val Leu Gln Pro Leu Ile Ala Glu His Gln Ala Arg
        435                 440                 445

Arg Lys Glu Val Thr Asp Glu Ile Val Lys Glu Phe Met Thr Pro Arg
    450                 455                 460

Lys Leu Ser Phe Asp Phe Gln
465                 470
```